United States Patent [19]

Cain et al.

[11] Patent Number: 5,739,163
[45] Date of Patent: Apr. 14, 1998

[54] AROMATIC COMPOUNDS CONTAINING BASIC AND ACIDIC TERMINI USEFUL AS FIBRINOGEN RECEPTOR ANTAGONISTS

[75] Inventors: Gary Avonn Cain; Charles Joseph Eyermann; Richard Eric Olson, all of Wilmington, Del.

[73] Assignee: The DuPont Merck Pharmaceutical Company, Wilmington, Del.

[21] Appl. No.: 612,597

[22] Filed: Mar. 8, 1996

Related U.S. Application Data

[62] Division of Ser. No. 157,860, Nov. 24, 1993, Pat. No. 5,523,302.

[51] Int. Cl.$^6$ .................. A61K 31/498; C02C 229/38
[52] U.S. Cl. .................. 514/539; 514/561; 514/562; 514/567; 560/16; 560/21; 562/430; 562/451
[58] Field of Search .................. 560/16, 21; 562/451, 562/430; 514/539, 561, 562, 567

[56] References Cited

U.S. PATENT DOCUMENTS 5,039,805  8/1991  Alig et al. .................. 546/224

FOREIGN PATENT DOCUMENTS

| | | |
|---|---|---|
| 2008311 | 7/1990 | Canada . |
| 2061661 | 9/1992 | Canada . |
| 2074685 | 1/1993 | Canada . |
| 2093770 | 10/1993 | Canada . |
| 525629 | of 0000 | European Pat. Off. . |
| 381033 | 8/1990 | European Pat. Off. . |
| 445796 | 9/1991 | European Pat. Off. . |
| 478328 | 4/1992 | European Pat. Off. . |
| 478362 | 4/1992 | European Pat. Off. . |
| 478363 | 4/1992 | European Pat. Off. . |
| 0512831 | 11/1992 | European Pat. Off. . |
| 512829 | 11/1992 | European Pat. Off. . |
| 9307867 | of 0000 | WIPO . |

OTHER PUBLICATIONS

Phillips et al. *Cell* (1991) 65, 359–362.

Hartman et al. *J Med Chem* (1992) 35 4640–4642.

Alig et al. *J Med Chem* (1992) 35 4393–4407.

*Primary Examiner*—Robert Gerstl

[57] ABSTRACT

This invention relates to novel compounds containing basic and acidic termini, pharmaceutical compositions containing such compounds, processes for preparing such compounds, and to methods of using these compounds, alone or in combination with other therapeutic agents, for the inhibition of platelet aggregation, as thrombolytics, and/or for the treatment of thromboembolic disorders.

17 Claims, No Drawings

AROMATIC COMPOUNDS CONTAINING BASIC AND ACIDIC TERMINI USEFUL AS FIBRINOGEN RECEPTOR ANTAGONISTS

This is a division of application Ser. No. 08/157,860, filed Nov. 24, 1993, now U.S. Pat. No. 5,523,302.

FIELD OF THE INVENTION

This invention relates to novel compounds containing basic and acidic termini, pharmaceutical compositions containing such compounds, processes for preparing such compounds, and to methods of using these compounds, alone or in combination with other therapeutic agents, for the inhibition of platelet aggregation, as thrombolytics, and/or for the treatment of thromboembolic disorders.

BACKGROUND OF THE INVENTION

Hemostasis is the normal physiological process in which bleeding from an injured blood vessel is arrested. It is a dynamic and complex process in which platelets play a key role. Within seconds of vessel injury, resting platelets become activated and are bound to the exposed matrix of the injured area by a phenomenon called platelet adhesion. Activated platelets also bind to each other in a process called platelet aggregation to form a platelet plug. This platelet plug can stop bleeding quickly, but it must be reinforced by fibrin for long-term effectiveness, until the vessel injury can be permanently repaired.

Thrombosis may be regarded as the pathological condition wherein improper activity of the hemostatic mechanism results in intravascular thrombus formation. Activation of platelets and the resulting platelet aggregation and platelet factor secretion has been associated with different pathophysiological conditions including cardiovascular and cerebrovascular thromboembolic disorders, for example, the thromboembolic disorders associated with unstable angina, myocardial infarction, transient ischemic attack, stroke, atherosclerosis, and diabetes. The contribution of platelets to these disease processes stems from their ability to form aggregates, or platelet thrombi, especially in the arterial wall following injury.

Platelets are known to play an essential role in the maintenance of hemostasis and in the pathogenesis of arterial thrombosis. Platelet activation has been shown to be enhanced during coronary thrombolysis. This can lead to delayed reperfusion and reocclusion. Clinical studies with aspirin, ticlopidine, and a monoclonal antibody for platelet glycoprotein IIb/IIIa provide biochemical evidence for platelet involvement in unstable angina, early stage acute myocardial infarction, transient ischemic attack, cerebral ischemia, and stroke.

Platelets are activated by a wide variety of agonists resulting in platelet shape change, secretion of granular contents and aggregation. Aggregation of platelets serves to further focus clot formation by concentrating activated clotting factors in one site. Several endogenous agonists, including adenosine diphosphate (ADP), serotonin, arachidonic acid, thrombin, and collagen, have been identified. Because of the involvement of several endogenous agonists in activating platelet function and aggregation, an inhibitor which acts against all agonists would represent a more efficacious antiplatelet agent than currently available antiplatelet drugs, which are agonist-specific.

Current antiplatelet drugs are effective against only one type of agonist; these include aspirin, which acts against arachidonic acid; ticlopidine, which acts against ADP; thromboxane $A_2$ synthetase inhibitors or receptor antagonists, which act against thromboxane $A_2$; and hirudin, which acts against thrombin.

Recently, a common pathway for all known agonists has been identified, namely the platelet glycoprotein IIb/IIIa complex (GPIIb/IIIa or IIb/IIIa), which is the membrane protein mediating platelet aggregation. A recent review of GPIIb/IIIa is provided by Phillips et al. (1991) Cell 65: 359–362. The development of a GPIIb/IIIa antagonist represents a promising new approach for antiplatelet therapy. Recent studies in man with a monoclonal antibody for GPIIb/IIIa indicate the antithrombotic benefit of a GPIIb/IIIa antagonist.

There is presently a need for a GPIIb/IIIa-specific antiplatelet agent which inhibits the activation and aggregation of platelets in response to any agonist. Such an agent should represent a more efficacious antiplatelet therapy than the currently available agonist-specific platelet inhibitors.

GPIIb/IIIa on unstimulated platelets does not bind soluble proteins, but GPIIb/IIIa in activated platelets is known to bind four soluble adhesive proteins, namely fibrinogen, von Willebrand factor, fibronectin, and vitronectin. The binding of fibrinogen and von Willebrand factor to GPIIb/IIIa causes platelets to aggregate. The binding of fibrinogen is mediated in part by the Arg-Gly-Asp (RGD) recognition sequence which is common to the adhesive proteins that bind GPIIb/IIIa.

Several RGD-peptidomimetic compounds have been reported which block fibrinogen binding and prevent the formation of platelet thrombi.

For example, Canadian Patent Application 2,008,311 (Alig et al.) describes carboxamides and sulphonamides of the following formula:

$$R^1—A—(W)_a—X—(CH_2)_b—(Y)_c—B—Z—COOR$$

wherein:

A is selected from a radical including phenyl-$R^3$, pyridyl-$R^3$, or thiophenyl-$R^3$;

B is selected from a radical including phenyl-$R^4$, pyridyl-$R^4$, or thiophenyl-$R^4$;

W is selected from —$CH_2$—, —$CH_2CH_2$—, —CH=CH—, —CH=CH—$CH_2$—, —$(CH_2)_3$—, —$CH_2CH(CH_3)$—, —$COCH_2$—, —$CH(OH)CH_2$—, or —$CH_2COCH_2$—;

X is selected from —$CONR^2$—, —$NR^2CO$—, —$SO_2NR^2$—, or —$NR^2SO_2$—;

Y is selected from —$CH_2CH_2$—, —$CH_2CH_2O$—, —$OCH_2$—, —$CH(CH_3)CH_2$—, —CH=CH—, etc.;

Z is selected from —$OCH_2$—, —$NR^6CH_2$—, —$CH_2CH_2$—, —$CH(CH_3)CH_2$—, —$CH_2$—, —CH=CH—, or —$C(CH_3)$=CH—;

R is selected from H, lower alkyl, phenyl or phenyl-lower alkyl;

$R^1$ is selected from amidino or guanidino;

$R^2$ is selected from H, lower alkyl, phenyl-lower-alkyl, etc.;

$R^3$ is selected from H, lower alkyl, lower alkoxy, halogen, lower carbalkoxy, amino, lower alkylamino, di-lower-alkylamino or amidino;

$R^4$ is selected from H, lower alkyl, lower alkoxy, halogen, lower carbalkoxy, amino, lower alkylamino, di-lower-alkylamino or a radical —Z—COOR or —CH=CH—$(CH_2)_n$COOR;

$R^6$ is selected from H, lower alkyl or benzyl;

n is selected from an integer of 0–4;

a and c denote an integer of 0 or 1;

b is selected from an integer of 0–2, where a and b are 0 when c is 1, and c is 0 when a or b is different from zero.

These compounds are claimed as medicines for the treatment of thrombosis, apoplexy, myocardial infarction, inflammations, arteriosclerosis, and tumors.

European Patent Application Publication Number 0,478, 363,A2 (Laswell et al.) describes sulfonamide fibrinogen IIb/IIIa receptor antagonists of formula:

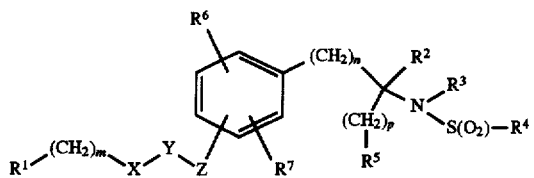

wherein:

$R^1$ is selected from a 4 to 8 membered heterocyclic ring containing 1–4 heteroatoms; amine, amidine, guanidine, quinuclidine, or isoquinuclidine, all of which may be further substituted;

$R^2$ and $R^3$ denote H, aryl, $C_1$ to $C_{10}$ alkyl or cycloalkyl, which may be further substituted;

$R^4$ is selected from aryl, $C_1$ to $C_{10}$ alkyl, cycloalkyl, aralkyl, alkaryl, alkanoyl, alkylamino, alkoxyalkyl, or carboxyalkyl;

$R^5$ is selected from a 4 to 8 membered heterocyclic ring with 1–4 heteroatoms, carboxylic acids, esters, or aminoacid linked carboxamides, and prodrugs thereof;

X, Y, Z are optional substituents selected from N, O, $S(O)_{0-2}$, C=O, C=S, CH—OH, CH=CH, C≡C, a 4 to 8 membered ring with 0–4 heteroatoms, aryl, amide, or sulfonamide;

m, n are selected from an integer from 0 to 10; and p is selected from an integer from 0 to 3.

European Patent Application Publication Number 0,478, 328 A1 (Egbertson et al.) discloses related fibrinogen receptor antagonists wherein the $SO_2R^4$ group of the compounds in EP 0,478,363,A2 is replaced by the $R^4$ substituent,

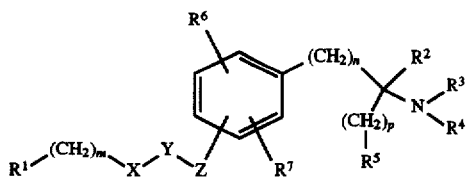

wherein $R^4$ is selected from H, aryl, amino acid with amide linkage, $C_1$ to $C_{10}$ alkyl, cycloalkyl, aralkyl, alkaryl, alkanoyl, alkylamino, alkoxyalkyl, and carboxyalkyl.

None of the above-cited references disclose or suggest the novel compounds of the present invention.

Compounds of the present invention represent novel structures which bind to the glycoprotein IIb/IIIa receptor, thereby preventing fibrinogen from binding at its platelet receptor site, leading to efficacy in the prevention of blood platelet aggregation and subsequent clotting disorders.

SUMMARY OF THE INVENTION

This invention provides novel aromatic compounds containing basic and acidic termini of Formula I (described below) which are useful as antagonists of the platelet glycoprotein IIb/IIIa complex. The compounds of the present invention inhibit the binding of fibrinogen to platelet glycoprotein IIb/IIIa complex and inhibit the aggregation of platelets. The present invention also includes pharmaceutical compositions containing such compounds of Formula I, and methods of using such compounds for the inhibition of platelet aggregation, as thrombolytics, and/or for the treatment of thromboembolic disorders.

The present invention also includes methods of treating thromboembolic disorders by administering a compound of Formula I in combination with one or more second therapeutic agents selected from: anti-coagulants such as warfarin or heparin; anti-platelet agents such as aspirin, piroxicam or ticlopidine; thrombin inhibitors such as boropeptides, hirudin or argatroban; or thrombolytic agents such as tissue plasminogen activator, anistreplase, urokinase or streptokinase; or combinations thereof.

Also included in the present invention are pharmaceutical kits comprising one or more containers containing pharmaceutical dosage units comprising a compound of Formula I, for the treatment of thromboembolic disorders.

DETAILED DESCRIPTION OF THE INVENTION

This invention provides novel aromatic compounds containing basic and acidic termini of Formula I (described below) which are useful as antagonists of the platelet glycoprotein IIb/IIIa complex. The compounds of the present invention inhibit the binding of fibrinogen to the platelet glycoprotein IIb/IIIa complex and inhibit the aggregation of platelets. The present invention also includes pharmaceutical compositions containing such compounds of Formula I, and methods of using such compounds for the inhibition of platelet aggregation, as thrombolytics, and/or for the treatment of thromboembolic disorders.

The present invention provides compounds of the Formula I:

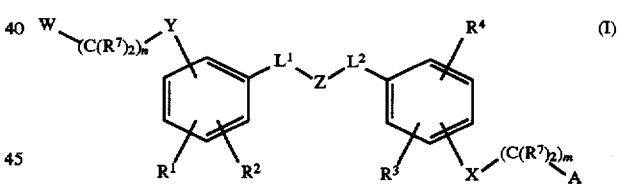

or pharmaceutically acceptable salt or prodrug forms thereof wherein:

W is selected from —$NR^6R^{6a}$, —$C(=NR^6)NHR^{6a}$, —$NR^6$—$C(=NR^{6a})NHR^8$, piperazinyl, or piperidinyl;

Y is selected from —$C(R^7)_2$—, —$C(=O)$—, —$S(O)_p$—, —O—, —$N(R^6)$—, —$NR^6C(=O)$—, —$C(=O)N(R^6)$— or a single bond;

with the proviso that when n=0, then the bond between W and Y is not a heteroatom to heteroatom bond;

with the proviso that when n=0 and W is $NH_2$, then Y is not —C(=O)— or —$C(=O)N(R^6)$—;

with the proviso that when n=1 and W is —$NR^6R^{6a}$, then Y is not —$S(O)_p$—, —O—, —$N(R^6)$—, or —$NR^6C(=O)$—;

$L^1$ and $L^2$ are independently selected from:
 a single bond,
 —($C_1$ to $C_4$ alkyl)—, substituted with 0–8 $R^{5b}$,
 —($C_2$ to $C_4$ alkenyl)—, substituted with 0–6 $R^{5b}$,
 —($C_2$ to $C_4$ alkynyl)—, substituted with 0–4 $R^{5b}$,
 —(cyclopropyl)—, substituted with 0–1 $R^{5b}$, with the proviso that at least one of $L^1$ or $L^2$, but not both of $L^1$ or $L^2$, are a bond;

alternatively, $L^1$ is taken together with $R^2$ to form a benzo-fused ring, said benzo-fused ring being substituted with 0–1 $R^5$;

alternatively, $L^2$ is taken together with $R^3$ to form a benzo-fused ring, said benzo-fused ring being substituted with 0–1$R^5$;

Z is selected from —C(=O)— or —S(O)$_p$—;

X is selected from —C(=O)—, —S(O)$_p$—, O, —N($R^6$)—, —$NR^6$C(=O)—, —C(=O)N($R^6$)—, or a single bond;

A is selected from $CO_2R^9$, $SO_3H$, tetrazolyl, or $PO_3H$;

$R^1$, $R^2$, $R^3$, $R^4$, and $R^7$ are independently selected from:
H,
$C_1$ to $C_8$ alkyl substituted with 0–5 $R^5$,
$C_2$ to $C_8$ alkenyl substituted with 0–5 $R^5$
$C_3$ to $C_8$ alkynyl substituted with 0–5 $R^5$,
$C_3$ to $C_8$ cycloalkyl substituted with 0–5 $R^5$,
$C_4$ to $C_8$ cycloalkylalkyl substituted with 0–5 $R^5$,
$C_7$ to $C_{11}$ arylalkyl substituted with 0–5 $R^5$,
$C_1$ to $C_4$ alkoxy substituted with 0–5 $R^5$,
aryl substituted with 0–5 $R^5$;
a 5–10-membered heterocyclic ring system containing 1–4 heteroatoms independently selected from N, S, and O, said heterocyclic ring being substituted with 0–4 $R^5$;
F, Cl, Br, I, CF3, CN, CHO, $CO_2R^{5a}$, C(=O)$R^{5a}$, CONHR$^{5a}$, CON($R^{5a}$)$_2$, OC(=O)$R^{5a}$, OC(=O) OR$^{5a}$, OR$^{5a}$, OC(=O)N($R^{5a}$)$_2$, OCH$_2$CO$_2R^{5a}$, CO$_2$CH$_2$CO$_2R^{5a}$, N($R^{5a}$)$_2$, NO$_2$, NR$^{5a}$C(=O)$R^{5a}$, NR$^{5a}$C(=O) OR$^{5a}$, NR$^{5a}$C(=O)N($R^{5a}$)$_2$, NR$^{5a}$SO$_2$N($R^{5a}$)$_2$, NR$^{5a}$SO$_2R^{5a}$, S(O)$_pR^{5a}$, or SO$_2$N($R^{5a}$)$_2$;

alternatively, when m or n are 2–6, $R^7$ can be taken together with $R^7$ bonded to an adjacent carbon atom to form a direct bond, thereby to form a double or triple bond between the adjacent carbon atoms;

$R^5$ is selected independently from H, F, Cl, Br, I, CF$_3$, CN, CHO, $CO_2R^{5a}$, C(=O) $R^{5a}$, CONHR$^{5a}$, CON ($R^{5a}$)$_2$, OC(=O) $R^{5a}$, OC(=O) OR$^{5a}$, OR$^{5a}$, OC(=O)N($R^{5a}$)$_2$, OCH$_2$CO$_2R^{5a}$, CO$_2$CH$_2$CO$_2R^{5a}$, N($R^{5a}$)$_2$, NO$_2$, NR$^{5a}$C(=O)$R^{5a}$, NR$^{5a}$C(=O)OR$^{5a}$, NR$^{5a}$C(=O)N($R^{5a}$)$_2$, NR$^{5a}$SO$_2$N($R^{5a}$)$_2$, NR$^{5a}$SO$_2R^{5a}$, S(O)$_pR^{5a}$, or SO$_2$N($R^{5a}$)$_2$, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl;

$R^{5b}$ is selected independently from H, F, Cl, Br, I, CF$_3$, CN, CHO, $CO_2R^{5a}$, C(=O)$R^{5a}$, CONHR$^{5a}$, CON ($R^{5a}$)$_2$, OC(=O)$R^{5a}$, OC(=O) OR$^{5a}$, OR$^{5a}$, OC(=O) N($R^{5a}$)$_2$, OCH$_2$CO$_2R^{5a}$, CO$_2$CH$_2$CO$_2R^{5a}$, N($R^{5a}$)$_2$, NO$_2$, NR$^{5a}$C(=O)$R^{5a}$, NR$^{5a}$C(=O)OR$^{5a}$, NR$^{5a}$C (=O)N($R^{5a}$)$_2$, NR$^{5a}$SO$_2$N($R^{5a}$)$_2$, NR$^{5a}$SO$_2R^{5a}$, S(O)$_p$ $R^{5a}$, or SO$_2$N($R^{5a}$)$_2$, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl;

alternatively, two $R^{5b}$ groups when attached to adjacent carbon atoms may be taken together to form —CH$_2$—, thereby to form a cyclopropylene group;

$R^{5a}$ is selected from: H, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl;

$R^6$, $R^{6a}$, and $R^8$ are independently selected from: H, $C_1$ to $C_4$ alkyl, $C_3$ to $C_{11}$ cycloalkyl, $C_6$ to $C_{10}$ aryl, $C_7$ to $C_{11}$ arylalkyl, $C_2$ to $C_7$ alkylcarbonyl, $C_7$ to $C_{11}$ arylcarbonyl, $C_2$ to $C_{10}$ alkoxycarbonyl, $C_4$ to $C_{11}$ cycloalkoxycarbonyl, $C_7$ to $C_{11}$ bicycloalkoxycarbonyl, or $C_7$ to $C_{11}$ aryloxycarbonyl;

$R^9$ is selected from H, $C_1$ to $C_8$ alkyl, $C_3$ to $C_{11}$ cycloalkyl, $C_6$ to $C_{10}$ aryl, $C_7$ to $C_{11}$ aralkyl, $C_3$ to $C_{10}$ alkylcarbonyloxyalkyl, $C_3$ to $C_{10}$ alkoxycarbonyloxyalkyl, $C_2$ to $C_{10}$ alkoxycarbonyl, $C_5$ to $C_{10}$ cycloalkylcarbonyloxyalkyl, $C_5$ to $C_{10}$ cycloalkoxycarbonyloxyalkyl, $C_5$ to $C_{10}$ cycloalkoxycarbonyl, $C_7$ to $C_{11}$ aryloxycarbonyl, $C_8$ to $C_{12}$ aryloxycarbonyloxyalkyl, $C_8$ to $C_{12}$ arylcarbonyloxyalkyl, $C_5$ to $C_{10}$ alkoxyalkylcarbonyloxyalkyl, $C_5$ to $C_{10}$ (5-alkyl-1,3-dioxa-cyclopenten-2-one-yl)methyl, or $C_{10}$ to $C_{14}$ (5-aryl-1,3-dioxa-cyclopenten-2-one-yl)methyl;

m is an integer from 1–6, with the proviso that m plus n cannon be greater than 6;

n is an integer from an integer from 0 to 6;

p is an integer from 0 to 2.

The present invention also provides compounds of the Formula Ia:

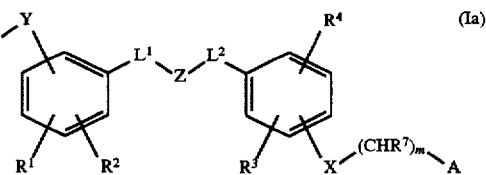

or pharmaceutically acceptable salt or prodrug forms thereof wherein:

W is selected from —NR$^6R^{6a}$, —C(=NR$^6$)NHR$^{6a}$, —NR$^6$—C(=NR$^{6a}$)NHR$^8$, piperazinyl, or piperidinyl;

Y is selected from —CH$_2$—, —C(=O)—, —S(O)$_p$—, —O—, —N($R^6$)—, —NR$^6$C(=O)—, —C(=O)N ($R^6$)— or a single bond;

with the proviso that when n=0, then the bond between W and Y is not a heteroatom to heteroatom bond;

with the proviso that when n=0 and W is NH$_2$, then Y is not —C(=O)— or —C(=O)N($R^6$)—;

with the proviso that when n=1 and W is —NR$^6R^{6a}$, then Y is not —S(O)$_p$—, —O—, —N($R^6$)—, or —NR$^6$C (=O)—;

$L^1$ and $L^2$ are independently selected from:
a single bond,
—($C_1$ to $C_4$ alkyl)— substituted with 0–4 $R^{5b}$,
—($C_2$ to $C_4$ alkenyl)— substituted with 0–4 $R^{5b}$,
—($C_2$ to $C_4$ alkynyl)— substituted with 0–3 $R^{5b}$,
—(cyclopropyl)—, substituted with 0–1$R^{5b}$,
with the proviso that at least one of $L^1$ or $L^2$, but not both of $L^1$ or $L^2$, are a bond;

alternatively, $L^1$ is taken together with $R^2$ to form a benzo-fused ring, said benzo-fused ring being substituted with 0–1$R^5$;

alternatively, $L^2$ is taken together with $R^3$ to form a benzo-fused ring, said benzo-fused ring being substituted with 0–1 $R^5$;

Z is selected from —C(=O)— or —S(O)$_p$—;

X is selected from —C(=O)—, —S(O)$_p$—, O, —N($R^6$)—, —NR$^6$C(=O)—, —C(=O)N($R^6$)—, or a single bond;

A is selected from $CO_2R^9$, $SO_3H$, tetrazolyl, or $PO_3H$;

$R^1$, $R^2$, $R^3$, $R^4$, and $R^7$ are independently selected from:

H,
$C_1$ to $C_8$ alkyl substituted with 0–4 $R^5$,
$C_2$ to $C_8$ alkenyl substituted with 0–4 $R^5$
$C_3$ to $C_8$ alkynyl substituted with 0–4 $R^5$,
$C_3$ to $C_8$ cycloalkyl substituted with 0–4 $R^5$,
$C_4$ to $C_8$ cycloalkylalkyl substituted with 0–4 $R^5$,
$C_6$ to $C_{10}$ aryl substituted with 0–2 $R^5$,
$C_7$ to $C_{11}$ arylalkyl substituted with 0–2 $R^5$,
$C_1$ to $C_4$ haloalkoxy, F, Cl, Br, I, $CF_3$, CN, CHO, $CO_2R^{5a}$, $C(=O)$ $R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O)R^{5a}$, $NR^{5a}C(=O)OR^{5a}$, $NR^{5a}C(=O)N(R^{5a})_2$, $NR^{5a}SO_2N(R^{5a})_2$, $NR^{5a}SO_2R^{5a}$, $S(O)_pR^{5a}$, or $SO_2N(R^{5a})_2$;

$R^5$ is selected independently from H, F, Cl, Br, I, $CF_3$, CN, CHO, $CO_2R^{5a}$, $C(=O)R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O)R^{5a}$, $NR^{5a}C(=O)OR^{5a}$, $NR^{5a}C(=O)N(R^{5a})_2$, $NR^{5a}SO_2N(R^{5a})_2$, $NR^{5a}SO_2R^{5a}$, $S(O)_pR^{5a}$, or $SO_2N(R^{5a})_2$, $C_1$ to $C_8$ alkyl, $C_2$ to $C_6$ alkenyl, $C_3$ to $C_8$ cycloalkyl, $C_4$ to $C_8$ cycloalkylmethyl, $C_6$ to $C_{10}$ aryl, or $C_7$ to $C_{11}$ arylalkyl;

$R^{5b}$ is selected independently from H, F, Cl, Br, I, $CF_3$, CN, CHO, $CO_2R^{5a}$, $C(=O)R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O)R^{5a}$, $NR^{5a}C(=O)OR^{5a}$, $NR^{5a}C(=O)N(R^{5a})_2$, $NR^{5a}SO_2N(R^{5a})_2$, $NR^{5a}SO_2R^{5a}$, $S(O)_pR^{5a}$, or $SO_2N(R^{5a})_2$, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl;

alternatively, two $R^{5b}$ groups when attached to adjacent carbon atoms may be taken together to form —$CH_2$—, thereby to form a cyclopropylene group;

$R^{5a}$ is selected from: H, $C_1$ to $C_8$ alkyl, $C_2$ to $C_6$ alkenyl, $C_3$ to $C_8$ cycloalkyl, $C_4$ to $C_8$ cycloalkylmethyl, $C_6$ to $C_{10}$ aryl, or $C_7$ to $C_{11}$ arylalkyl;

$R^6$, $R^{6a}$, and $R^8$ are independently selected from: H, $C_1$ to $C_4$ alkyl, $C_3$ to $C_{10}$ cycloalkyl, $C_6$ to $C_{10}$ bicycloalkyl, $C_6$ to $C_{10}$ aryl, $C_7$ to $C_{11}$ arylalkyl $C_2$ to $C_7$ alkylcarbonyl, $C_7$ to $C_{11}$ arylcarbonyl, $C_2$ to $C_{10}$ alkoxycarbonyl, $C_4$ to $C_{11}$ cycloalkoxycarbonyl, $C_7$ to $C_{11}$ bicycloalkoxycarbonyl, or $C_7$ to $C_{11}$ aryloxycarbonyl;

$R^9$ is selected from H, $C_1$ to $C_8$ alkyl, $C_3$ to $C_{10}$ cycloalkyl, $C_6$ to $C_{10}$ aryl, $C_7$ to $C_{11}$ aralkyl, $C_3$ to $C_{10}$ alkylcarbonyloxyalkyl, $C_3$ to $C_{10}$ alkoxycarbonyloxyalkyl, $C_2$ to $C_{10}$ alkoxycarbonyl, $C_5$ to $C_{10}$ cycloalkylcarbonyloxyalkyl, $C_5$ to $C_{10}$ cycloalkoxycarbonyloxyalkyl, $C_5$ to $C_{10}$ cycloalkoxycarbonyl, $C_7$ to $C_{11}$ aryloxycarbonyl, $C_8$ to $C_{12}$ aryloxycarbonyloxyalkyl, $C_8$ to $C_{12}$ arylcarbonyloxyalkyl, $C_5$ to $C_{10}$ alkoxyalkylcarbonyloxyalkyl, $C_5$ to $C_{10}$ (5-alkyl-1,3-dioxa-cyclopenten-2-one-yl)methyl, or $C_{10}$ to $C_{14}$ (5-aryl-1,3-dioxa-cyclopenten-2-one-yl)methyl;

m is an integer from 1–6, with the proviso that m plus n cannot be greater than 6;
n is an integer from an integer from 0 to 6;
p is an integer from 0 to 2.

Preferred are the above compounds of Formula I wherein $L^1$ is a bond.

Preferred compounds of the present invention are compounds of the Formula Ib:

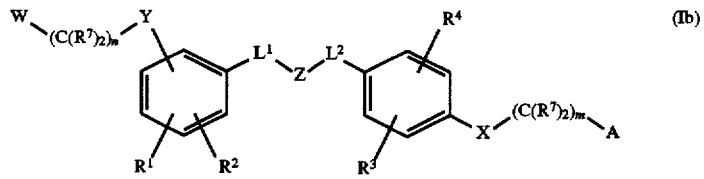
(Ib)

or pharmaceutically acceptable salt or prodrug forms thereof wherein:

W is selected form —$NR^6R^{6a}$, —$C(=NR^6)NHR^{6a}$, —$NR^6$—$C(=NR^{6a})NHR^8$, piperazinyl, or piperidinyl;

Y is selected from —$CH_2$—, —$C(=O)$—, —$S(O)_p$—, —O—, —$N(R^6)$—, —$NR^6C(=O)$—, —$C(=O)N(R^6)$— or a single bond;

with the proviso that when n=0, then the bond between W and Y is not a heteroatom to heteroatom bond;

with the proviso that when n=0 and W is $NH_2$, then Y is not —$C(=O)$— or —$C(=O)N(R^6)$—;

with the proviso that when n=1 and W is —$NR^6R^{6a}$, then Y is not —$S(O)_p$—, —O—, —$N(R^6)$—, or —$NR^6C(=O)$—;

$L^1$ and $L^2$ are independently selected from:
a single bond,
—($C_1$ to $C_4$ alkyl)— substituted with 0–4 $R^{5b}$,
—($C_2$ to $C_4$ alkenyl)— substituted with 0–4 $R^{5b}$,
—($C_2$ to $C_4$ alkynyl)— substituted with 0–3 $R^{5b}$,
—(cyclopropyl)—, substituted with 0–1$R^{5b}$,
with the proviso that at least one of $L^1$ or $L^2$, but not both of $L^1$ or $L^2$, are a bond;

alternatively, $L^1$ is taken together with $R^2$ to form a benzo-fused ring, said benzo-fused ring being substituted with 0–1$R^5$;

alternatively, $L^2$ is taken together with $R^3$ to form a benzo-fused ring, said benzo-fused ring being substituted with 0–1$R^5$;

Z is selected from —$C(=O)$— or —$S(O)_p$—;

X is selected from —$C(=O)$—, —$S(O)_p$—, O, —$N(R^6)$—, —$NR^6C(=O)$—, —$C(=O)N(R^6)$—, or a single bond;

A is selected from $CO_2R^9$, $SO_3H$, tetrazolyl, or $PO_3H$;

$R^1$, $R^2$, $R^3$, $R^4$, and $R^7$ are independently selected from: H,
$C_1$ to $C_8$ alkyl substituted with 0–4 $R^5$,
$C_2$ to $C_8$ alkenyl substituted with 0–4 $R^5$
$C_3$ to $C_8$ alkynyl substituted with 0–4 $R^5$,
$C_3$ to $C_8$ cycloalkyl substituted with 0–4 $R^5$,
$C_4$ to $C_8$ cycloalkylalkyl substituted with 0–4 $R^5$,
$C_6$ to $C_{10}$ aryl substituted with 0–2 $R^5$,
$C_7$ to $C_{11}$ arylalkyl substituted with 0–2 $R^5$,
$C_1$ to $C_4$ haloalkoxy,
F, Cl, Br, I, $CF_3$, CN, CHO, $CO_2R^{5a}$, $C(=O)R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O)R^{5a}$, $NR^{5a}C(=O)OR^{5a}$, $NR^{5a}C(=O)N(R^{5a})_2$, $NR^{5a}SO_2N(R^{5a})_2$, $NR^{5a}SO_2R^{5a}$, $S(O)_pR^{5a}$, or $SO_2N(R^{5a})_2$;

$R^5$ is selected independently from H, F, Cl, Br, I, $CF_3$, CN, CHO, $CO_2R^{5a}$, $C(=O)R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O)R^{5a}$, $NR^{5a}C(=O)OR^{5a}$, $NR^{5a}C(=O)N(R^{5a})_2$, $NR^{5a}SO_2N(R^{5a})_2$, $NR^{5a}SO_2R^{5a}$, $S(O)_pR^{5a}$, or $SO_2N(R^{5a})_2$, $C_1$ to $C_8$ alkyl, $C_2$ to $C_6$ alkenyl, $C_3$ to $C_8$ cycloalkyl, $C_4$ to $C_8$ cycloalkylmethyl, $C_6$ to $C_{10}$ aryl, or $C_7$ to $C_{11}$ arylalkyl;

$R^{5b}$ is selected independently from H, F, Cl, Br, I, $CF_3$, CN, CHO, $CO_2R^{5a}$, $C(=O)R^{5a}$ $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O)R^{5a}$, $NR^{5a}C(=O)^{OR5a}$, $NR^{5a}C(=O)N(R^{5a})_2$, $NR^{5a}SO_2N(R^{5a})_2$, $NR^{5a}SO_2R^{5a}$, $S(O)_pR^{5a}$, or $SO_2N(R^{5a})_2$, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl;

alternatively, two $R^{5b}$ groups when attached to adjacent carbon atoms may be taken together to form —$CH_2$—, thereby to form a cyclopropylene group;

$R^{5a}$ is selected from: H, $C_1$ to $C_8$ alkyl, $C_2$ to $C_6$ alkenyl, $C_3$ to $C_8$ cycloalkyl, $C_4$ to $C_8$ cycloalkylmethyl, $C_6$ to $C_{10}$ aryl, or $C_7$ to $C_{11}$ arylalkyl;

$R^6$, $R^{6a}$, and $R^8$ are independently selected from: H, $C_1$ to $C_4$ alkyl, $C_3$ to $C_{10}$ cycloalkyl, $C_6$ to $C_{10}$ bicycloalkyl, $C_6$ to $C_{10}$ aryl, $C_7$ to $C_{11}$ arylalkyl, $C_2$ to $C_7$ alkylcarbonyl, $C_7$ to $C_{11}$ arylcarbonyl, $C_2$ to $C_{10}$ alkoxycarbonyl, $C_4$ to $C_{11}$ cycloalkoxycarbonyl, $C_7$ to $C_{11}$ bicycloalkoxycarbonyl, or $C_7$ to $C_{11}$ aryloxycarbonyl;

$R^9$ is selected from H, $C_1$ to $C_8$ alkyl, $C_3$ to $C_{10}$ cycloalkyl, $C_6$ to $C_{10}$ aryl, $C_7$ to $C_{11}$ aralkyl, $C_3$ to $C_{10}$ alkylcarbonyloxyalkyl, $C_3$ to $C_{10}$ alkoxycarbonyloxyalkyl, $C_2$ to $C_{10}$ alkoxycarbonyl, $C_5$ to $C_{10}$ cycloalkylcarbonyloxyalkyl, $C_5$ to $C_{10}$ cycloalkoxycarbonyloxyalkyl, $C_5$ to $C_{10}$ cycloalkoxycarbonyl, $C_7$ to $C_{11}$ aryloxycarbonyl, $C_8$ to $C_{12}$ aryloxycarbonyloxyalkyl, $C_8$ to $C_{12}$ arylcarbonyloxyalkyl, $C_5$ to $C_{10}$ alkoxyalkylcarbonyloxyalkyl, $C_5$ to $C_{10}$ (5-alkyl-1,3-dioxa-cyclopenten-2-one-yl)methyl, or $C_{10}$ to $C_{14}$ (5-aryl-1,3-dioxa-cyclopenten-2-one-yl)methyl;

m is an integer from 1–6, with the proviso than m plus n cannot be greater than 6;

n is an integer from an integer from 0 to 6;

p is an integer from 0 to 2.

Preferred compounds of the present invention are compounds of Formula I, Ia, or Ib wherein:

W is selected form —$NR^6R^{6a}$, —$C(=NR^6)NHR^{6a}$, —$NR^6$—$C(=NR^{6a})NHR^8$, piperazinyl;

Y is selected from O, $CH_2$, S or a single bond;

$L^1$ and $L^2$ are independently selected from:
 a single bond,
 —$CH_2CH_2$— substituted with 0–2 $R^{5b}$, or
 —$CH=CH$— substituted with 0–2 $R^{5b}$;
 —(cyclopropyl)— substituted with 0–1 $R^{5b}$;
 with the proviso that at least one of $L^1$ or $L^2$, but not both of $L^1$ or $L^2$, are a bond;

alternatively, $L^1$ is taken together with $R^2$ to form a benzo-fused ring, said benzo-fused ring being substituted with 0–1$R^5$;

alternatively, $L^2$ is taken together with $R^3$ to form a benzo-fused ring, said benzo-fused ring being substituted with 0–1 $R^5$;

Z is selected from —$C(=O)$— or —$S(O)_p$—;

X is selected from —O— or a single bond;

A is selected from $CO_2R^9$, $SO_3H$, tetrazolyl, or $PO_3H$;

$R^1$ and $R^2$ are independently selected from:
 H,
 $C_1$ to $C_8$ alkyl substituted with 0–2 $R^5$,
 $C_2$ to $C_8$ alkenyl substituted with 0–2 $R^5$,
 $C_3$ to $C_8$ cycloalkyl substituted with 0–2 $R^5$,
 $C_4$ to $C_8$ cycloalkylmethyl substituted with 0–2 $R^5$,
 $OR^{5a}$;

$R^3$, $R^4$, and $R^7$ are independently selected from:
 H,
 $C_1$ to $C_8$ alkyl substituted with 0–2 $R^5$,
 $C_2$ to $C_8$ alkenyl substituted with 0–2 $R^5$,
 $C_3$ to $C_8$ cycloalkyl substituted with 0–2 $R^5$,
 $C_4$ to $C_8$ cycloalkylmethyl substituted with 0–2 $R^5$,
 $C_7$ to $C_{11}$ arylalkyl substituted with 0–2 $R^5$, aryl substituted with 0–2 $R^5$,
 F, Cl, Br, I, $CO_2R^{5a}$, $OR^{5a}$, $OCH_2CO_2R^{5a}$, $CO_2CH_2CO_2R^{5a}$, or $NO_2$; $R^5$ is selected independently from H, F, Cl, Br, I, $CF_3$, CN, CHO, $CO_2R^{5a}$, $C(=O)R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O)R^{5a}$, $NR^{5a}C(=O)OR^{5a}$, $NR^{5a}C(=O)N(R^{5a})_2$, $NR^{5a}SO_2N(R^{5a})_2$, $NR^{5a}SO_2R^{5a}$, $S(O)_pR^{5a}$, $SO_2N(R^{5a})_2$, $C_1$ to $C_8$ alkyl, $C_2$ to $C_6$ alkenyl, $C_3$ to $C_8$ cycloalkyl, $C_4$ to $C_8$ cycloalkylmethyl, $C_6$ to $C_{10}$ aryl, or $C_7$ to $C_{11}$ arylalkyl;

$R^{5b}$ is selected independently from H, $CF_3$, CN, CHO, $CO_2R^{5a}$, $CONHR^{5a}$, $CON(R^{5a})_2$, $OR^{5a}$, $N(R^{5a})_2$, $C_1$ to $C_6$ alkyl, $C_2$ to $C_6$ alkenyl, $C_3$ to $C_{11}$ cycloalkyl, $C_4$ to $C_7$ cycloalkylmethyl, $C_6$ to $C_{10}$ aryl, or $C_7$ to $C_{11}$ arylalkyl;

alternatively, two $R^{5b}$ groups when attached to adjacent carbon atoms may be taken together to form —$CH_2$—, thereby to form a cyclopropylene group;

$R^{5a}$ are selected independently from: H, $C_1$ to $C_6$ alkyl, $C_2$ to $C_6$ alkenyl, $C_4$ to $C_8$ cycloalkylmethyl, $C_6$ to $C_{10}$ aryl, or $C_7$ to $C_{11}$ arylalkyl;

$R^6$, $R^{6a}$, and $R^8$ are independently selected from H, $C_1$ to $C_4$ alkyl, $C_2$ to $C_7$ alkylcarbonyl, $C_7$ to $C_{11}$ arylcarbonyl, $C_2$ to $C_{10}$ alkoxycarbonyl, $C_4$ to $C_{11}$ cycloalkoxycarbonyl, $C_7$ to $C_{11}$ bicycloalkoxycarbonyl, or $C_7$ to $C_{11}$ aryloxycarbonyl;

$R^9$ is selected from H, $C_1$ to $C_4$ alkyl, $C_3$ to $C_{10}$ alkylcarbonyloxyalkyl, $C_3$ to $C_{10}$ alkoxycarbonyloxyalkyl, $C_2$ to $C_{10}$ alkoxycarbonyl, $C_5$ to $C_{10}$ cycloalkylcarbonyloxyalkyl, $C_5$ to $C_{10}$ cycloalkoxycarbonyloxyalkyl, $C_5$ to $C_{10}$ cycloalkoxycarbonyl, $C_7$ to $C_{11}$ aryloxycarbonyl, $C_8$ to $C_{12}$ aryloxycarbonyloxyalkyl, $C_8$ to $C_{12}$ arylcarbonyloxyalkyl, $C_5$ to $C_{10}$ alkoxyalkylcarbonyloxyalkyl, $C_5$ to $C_{10}$ (5alkyl-1,3-dioxa-cyclopenten-2-one-yl)methyl, or $C_{10}$ to $C_{14}$ (5-aryl-1,3-dioxa-cyclopenten-2-one-yl)methyl;

m is an integer from 1 or 2;

n is an integer from 1 to 3;

p is an integer from 0 to 2;

or pharmaceutically acceptable salt or prodrug forms thereof.

More preferred compounds are those compounds of Formula I wherein:

W is selected form —$NR^6R^{6a}$, —$NR^6$—$C(=NR^{6a})$ $NHR^8$, piperazinyl;

Y is selected from O, S, or a single bond;

$L^1$ and $L^2$ are selected from:
a bond;
—CH=CH— substituted with 0–2 $R^{5b}$; or
—(cyclopropyl)— substituted with 0–1$R^{5b}$;
with the proviso that at least one of $L^1$ or $L^2$, but not both of $L^1$ or $L^2$, are a bond;

alternatively, $L^2$ is taken together with $R^3$ to form a benzo-fused ring, said benzo-fused ring being substituted with 0–1 $R^5$;

Z is selected from —C(=O)— or $S(O)_p$;

X is selected from O or a single bond;

A is selected from $CO_2R^9$;

$R^1$ and $R^2$ are independently selected from:
H,
$C_1$ to $C_8$ alkyl substituted with 0–2 $R^5$,
$C_2$ to $C_8$ alkenyl substituted with 0–2 $R^5$,
$C_4$ to $C_8$ cycloalkylmethyl,
$OR^{5a}$;

$R^3$ and $R^4$ are independently selected from:
H,
$C_1$ to $C_6$ alkyl substituted with 0–2 $R^5$,
I, F, Br, Cl, $CO_2R^{5a}$, $OR^{5a}$, $OCH_2CO_2R^{5a}$, $CO_2CH_2CO_2R^{5a}$, or $NO_2$;

$R^5$, $R^7$, $R^{5a}$, and $R^{5b}$ are independently selected from H, $C_1$ to $C_6$ straight or branched alkyl, $C_2$ to $C_6$ alkenyl, $C_4$ to $C_7$ cycloalkylmethyl, or $C_7$ to $C_{11}$ arylalkyl;

$R^6$, $R^{6a}$, and $R^8$ are independently selected from H, $C_1$ to $C_2$ alkyl, $C_2$ to $C_7$ alkylcarbonyl, $C_7$ to $C_{11}$ arylcarbonyl, $C_2$ to $C_{10}$ alkoxycarbonyl, $C_4$ to $C_{11}$ cycloalkoxycarbonyl, $C_7$ to $C_{11}$ bicycloalkoxycarbonyl, or $C_7$ to $C_{11}$ aryloxycarbonyl;

$R^9$ is selected from H, $C_1$ to $C_4$ alkyl, $C_3$ to $C_{10}$ alkylcarbonyloxyalkyl, $C_3$ to $C_{10}$ alkoxycarbonyloxyalkyl, $C_2$ to $C_{10}$ alkoxycarbonyl, $C_5$ to $C_{10}$ cycloalkylcarbonyloxyalkyl, $C_5$ to $C_{10}$ cycloalkoxycarbonyloxyalkyl, $C_5$ to $C_{10}$ cycloalkoxycarbonyl, $C_7$ to $C_{11}$ aryloxycarbonyl, $C_8$ to $C_{12}$ aryloxycarbonyloxyalkyl, $C_8$ to $C_{12}$ arylcarbonyloxyalkyl, $C_5$ to $C_{10}$ alkoxyalkylcarbonyloxyalkyl, $C_5$ to $C_{10}$ (5-alkyl-1,3-dioxa-cyclopenten-2-one-yl)methyl, or $C_{10}$ to $C_{14}$ (5-aryl-1,3-dioxa-cyclopenten-2-one-yl)methyl;

m is selected from 1 or 2;

n is an integer from 1 to 3;

p is selected from 0, 1, or 2;

and pharmaceutically acceptable salts thereof.

Further preferred are those compounds described above, or a pharmaceutically acceptable salt form thereof, wherein $L^1$ is a bond and $L^2$ is —$CH_2$=$CH_2$—.

Specifically preferred compounds of the present invention are compounds, or a pharmaceutically acceptable salt or prodrug form thereof, selected from:

(a) (E)-ethyl 5-[3-((3-(2-aminoethoxy)phenyl))-3-oxo-1-propenyl]-2-(carboxymethoxy)benzoate;

(b) (E)-(carboxymethyl) 5-[3-((3-(2-aminoethoxy)phenyl))-3-oxo-1-propenyl]-2(carboxymethoxy)benzoate;

(c) (E)-ethyl 5-[3-((3-(2-aminoethoxy-5-ethoxyphenyl))-3-oxo-1-propenyl]-2-(carboxymethoxy)benzoate;

(d) (E)-4-[3-((3-(2-aminoethoxy)-5ethoxyphenyl))-3-oxo-1-propenyl]phenoxyacetic acid;

(e) (E)-ethyl 5-[3-((3-(2-aminopropyl)phenyl))-3-oxo-1-propenyl]-2-(carboxymethoxy)benzoate;

(f) (E)-benzyl 5-[3-((3-(2-aminoethoxy)phenyl))-3-oxo-1-propenyl]-2-(carboxymethoxy)benzoate;

(g) (E)-methyl 5-[3-((3-(2-aminoethoxy))phenyl))-3-oxo-1-propenyl]-2-(carboxymethoxy)benzoate;

(h) (E)-4-[3-((3-(2-aminoethoxy)phenyl))-3-oxo-1-propenyl]-2-nitrophenoxyacetic acid;

(I) (E)-ethyl 5-[3-((2-(1-prop-2-enyloxy)-5-(2-aminoethoxy))phenyl))-3-oxo-1-propenyl]-2-(carboxymethoxy)benzoate;

(j) (E)-n-butyl 5-[3-((3-(2-aminoethoxy)-phenyl))-3-oxo-1-propenyl]-2-(carboxymethoxy)benzoate;

(k) (E)-4-[3-((3-(2-aminoethoxy)phenyl))-3-oxo-1-propenyl]-2-ethoxyphenoxyacetic acid;

(l) (E)-(carboxymethyl) 5-[3-((2(benzyloxy)-5-(2-aminoethoxy))phenyl))-3-oxo-1-propenyl]-2-(carboxymethoxy)benzoate;

(m) (E)-(carboxymethyl) 5-((3-((2-(1-prop-2-enyloxy)-5-(2-aminoethoxy))phenyl))-3-oxo-1-propenyl))-2-(carboxymethoxy)benzoate;

(n) (E)-4-[3-((3-(2-aminoethoxy)phenyl))-3-oxo-1-propenyl]-3-methoxyphenoxyacetic acid;

(o) (E)-(2-ethoxy-2-oxo-ethyl) 5-[3-((3-(2-aminoethoxy)phenyl))-3-oxo-1-propenyl]-2(carboxymethoxy)benzoate;

(p) (E)-4-[3-((3-(aminomethyl)phenyl))-3-oxo-1-propenyl]benzene-1,2-bis(oxyacetic acid);

(q) (E)-4-[3-((3-(2-aminoethoxy)phenyl))-3-oxo-1-propenyl]-benzene-1,2-bis (oxyacetic acid);

(r) (E)-4-[3-((3-(2-aminoethoxy)phenyl))-3-oxo-1-propenyl]-2-methoxyphenoxyacetic acid;

(s) (E)-4-[3-((3-(2-aminoethyl)phenyl))-3-oxo-1-propenyl]-2-ethoxyphenoxyacetic acid;

(t) (E)-4-[3-((3-(2-aminoethoxy)phenyl))-3-oxo-1-propenyl]-phenoxyacetic acid;

(u) (E)-4-[3-((3-(1-piperazinyl)phenyl)-3-oxo-1-propenyl]-2-methoxyphenoxyacetic acid;

(v) (E)-4-[3-((3-(guanidinylmethyl)phenyl))-3-oxo-1-propenyl]-2-methoxyphenoxyacetic acid;

(w) (E)-4-[3-((3-(2-(methylamino)ethoxy))phenyl))-3-oxo-1-propenyl]-2-methoxyphenoxyacetic acid;

(x) (E)-4-[3-((3-(1-piperazinyl)phenyl))-3-oxo-1-propenyl]-2-nitrophenoxyacetic acid;

(y) (E)-ethyl 5-[3-((2-(3-methyl-1-butoxy)5-(2-aminoethoxy))phenyl))-3-oxo-1-propenyl]-2-(carboxymethoxy)benzoate;

(z) (E)-Methyl 5-[[3-[3-((2-(methylamino)ethoxy))-phenyl]-3-oxo-1-propenyl]]-2-(carboxymethoxy)-benzoate;

(aa) (E)-4-[3-((5-(2-aminoethoxy)-2-benzyloxy-phenyl))-1-oxo-1-prop-2-enyl]-2-ethoxyphenoxy-acetic acid;

(bb) (E)-4-[2-((3-(2-aminoethoxy)phenylsulfonyl))-ethenyl]-2-nitrophenoxyacetic acid;

(cc) (E)-4-[2-((3-(2-aminoethoxy)phenylthio))-ethenyl]-2-nitrophenoxyacetic acid;

(dd) (E)-4-[2-((3-(2-aminoethoxy)phenylsulfoxo))-ethenyl]-2-nitrophenoxyacetic acid;

(ee) (E)-4-[[1-[2-((3-(2-aminoethoxy)phenyl))-ethenyl] sulfonyl-2-methoxyphenoxyacetic acid;

(ff) (E)-4-[[1-[2-((3-(2-aminoethoxy)phenyl))-ethenyl] sulfoxo-2-methoxyphenoxyacetic acid;

(gg) (E)-4-[[1-[2-((3-(2-aminoethoxy)phenyl))-ethenyl] thio-2-methoxyphenoxyacetic acid.

In the present invention it has been discovered that the compounds of Formula I above are useful as inhibitors of glycoprotein IIb/IIIa (GPIIb/IIIa). The compounds of the present invention inhibit the activation and aggregation of platelets induced by all known endogenous platelet agonists.

The present invention also provides pharmaceutical compositions comprising a compound of Formula I and a pharmaceutically acceptable carrier.

The compounds of Formula I of the present invention are useful for the treatment (including prevention) of thromboembolic disorders. The term thromboembolic disorders as used herein includes conditions involving platelet activation and aggregation, such as arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or diabetes, comprising administering to a mammal in need of such treatment a therapeutically effective amount of a compound of Formula I described above.

The compounds of the present invention are useful for inhibiting the binding of fibrinogen to blood platelets, inhibiting aggregation of blood platelets, treating thrombus formation or embolus formation, or preventing thrombus or embolus formation in a mammal. The compounds of the invention may be used as a medicament for blocking fibrinogen from acting at its receptor site in a mammal.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption, and where the aggregated platelets may form thrombi and thromboemboli. The compounds of the present invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. Platelets released from artificial surfaces show impaired homeostatic function. Compounds of the invention may be administered to prevent adhesion.

Other applications of these compounds include prevention of platelet thrombosis, thromboembolism, and reocclusion during and after thrombolytic therapy and prevention of platelet thrombosis, thromboembolism and reocclusion after angioplasty of coronary and other arteries and after coronary artery bypass procedures. The compounds of the present invention may also be used to prevent myocardial infarction. The compounds of the present invention are useful as thrombolytics for the treatment of thromboembolic disorders.

The compounds of the present invention can also be administered in combination with one or more additional therapeutic agents select from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds of Formula I of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "therapeutically effective amount" it is meant an amount of a compound of Formula I that when administered alone or in combination with an additional therapeutic agent to a cell or mammal is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin (available as Coumadin™) and heparin.

The term anti-platelet agents (or platelet inhibitory agents), as used herein, denotes agents than inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sutindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam. Piroxicam is commercially available from Pfizer Inc. (New York, N.Y.), as Feldane™. Other suitable anti-platelet agents include ticlopidine, including pharmaceutically acceptable salts or prodrugs thereof. Ticlopidine is also a preferred compound since it is known to be gentle on the gastro-intestinal trace in use. Still other suitable platelet inhibitory agents include thromboxane-A2-receptor antagonists and thromboxane-$A_2$-synthetase inhibitors, as well as pharmaceutically acceptable salts or prodrugs thereof.

The phrase thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boropeptides, hirudin and argatroban, including pharmaceutically acceptable salts and prodrugs thereof. Preferably the thrombin inhibitors are boropeptides. By boropeptides, it is meant, N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boropeptide thrombin inhibitors include those disclosed in PCT Application Publication Number 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. Anistreplase is commercially available as Eminase™. The term urokinase, as used herein, is intended to denote both dual and single chain urokinase, the latter also being referred to herein as prourokinase.

Administration of the compounds of Formula I of the invention in Combination with such additional therapeutic agent, may afford an efficacy advantage over the compounds and agents alone, and may do so while permitting the use of lower doses of each. A lower dosage minimizes the potential of side effects, thereby providing an increased margin of safety.

GPIIb/IIIa is known to be overexpressed in metastatic tumor cells. The compounds or combination products of the present invention may also be useful for the treatment, including prevention, of metastatic cancer.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention may contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^5$, $R^{5a}$, and $R^6$, p, etc.) occurs more than one time in any constituent or in any formula, its definition on each occurrence is independent of its definition at every other occurrence. Thus, for example, if a group is shown to be substituted with 0-2 $R^5$, then said group may optionally be substituted with up to two $R^5$ and $R^5$ at each occurrence is selected independently from the defined list of possible $R^5$. Also, by way of example, for the group —N($R^{5a}$)$_2$, each of the two $R^{5a}$ substituents on N is independently selected from the defined list of possible $R^{5a}$. Similarly, by way of example, for the group —C($R^7$)$_2$—, each of the two $R^7$ substituents on C is independently selected from the defined list of possible $R^7$.

When a bond to a substituent is shown to cross the bond connecting two atoms in a ring, then such substituent may be bonded to any atom on the ring.

When a substituent is listed without indicating the atom via which such substituent is bonded to the rest of the compound of Formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "-(alkyl)-", "-(alkyenyl)-", "-(phenyl)-", and the like, refer to alkyl, alkenyl, and phenyl groups, respectively, which are connected by two bonds to the rest of the structure of Formula I. Such groups may alternatively and equivalently be denoted as "alkylene", "alkenylene", "phenylene", and the like, respectively.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heteroaryl" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H, 6H-1,5,2-dithiazinyl, thiophenyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4a H-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, and the like. Examples of representative carboxyl and amino prodrugs are included under the definition of $R^9$, $R^6$, $R^{6a}$, and $R^8$.

The pharmaceutically acceptable salts of the compounds of Formula I include the conventional nontoxic salts or the quaternary ammonium salts of the compounds of Formula I formed, for example, from nontoxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable sales of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

Compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

Compounds of this invention of Formula I wherein $L^1$ is a bond, Z is C=O, and $L^2$ is a $C_2$ alkene (Formula Ia) may be prepared, as shown in Scheme I, by reacting suitably protected compounds of Formula (II) and Formula (III) with a metal hydroxide (MOH) in an appropriate solvent at temperatures ranging from 0° to 200° C. followed by deprotection. The choice of protecting groups and methods for their removal will be apparent to one skilled in the art, as generally described in Green, T. and Wuts, P. *Protective Groups in Organic Synthesis*, 2nd ed.; J. Wiley & Sons: New York, 1991. Commonly employed solvents include the lower alcohols, such as methanol or ethanol, and N,N-dialkylamides, such as N,N-dimethylformamide. Alternatively, a two-phased system consisting of water and an immiscible organic solvent, such as dichloromethane, along with a phase transfer catalyst, such as a quaternary alkylammonium salt, may be used.

SCHEME I

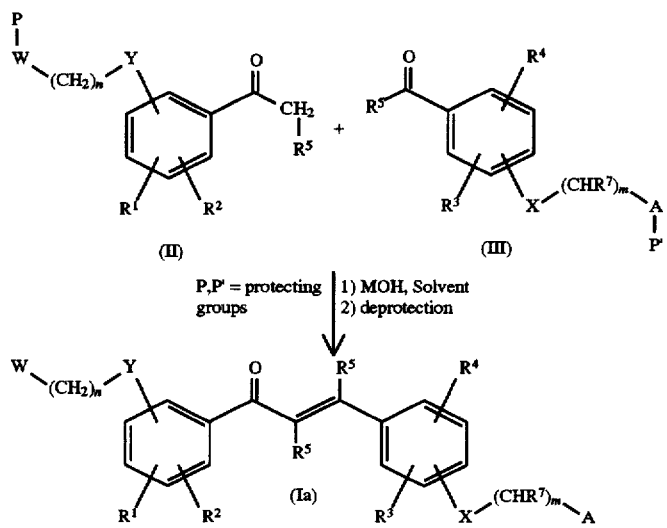

Compounds of Formula I wherein $L^1$ is a bond, Z is C=O, $L^2$ is a $C_2$ alkene, substituents $R^3$ and $R^4$ are sufficiently electron withdrawing (e.g. $R^3$=H and $R^4$=$NO_2$), and X=O, may be prepared, as shown in Scheme II, by treatment of suitably protected compounds of Formula (II) with free phenols of Formula (IV) and an excess amount of a metal hydroxide, typically 1.1 to 5 molar equivalents, in a solvent, such as methanol or ethanol, followed by an acidic workup to yield the intermediate phenol of Formula (V). This phenol (V) may be converted to product of Formula (Ib) via either of two alkylation methods, followed by final removal of protecting groups.

In the first alkylation method, the phenol (V) is treated with a base and an acid group protected reagent of Formula (VI) bearing a suitable leaving group in an appropriate solvent. Suitable bases include, but are not limited to, metal carbonates, non-nucleophilic tertiary amines, metal hydroxides, and metal hydrides. Typically used solvents are polar in nature, such as lower alcohols (methanol or ethanol), lower ketones (such as acetone), ethers (such as tetrahydrofuran), sulfoxides (such as dimethyl sulfoxide), and N,N-dialkylamides (such as N,N-dimethylformamide). Leaving groups G include halogens (especially Br, I) and alkyl- or aryl-sulfonates.

The second type of alkylation involves reaction of the phenol (V) with an alcohol of Formula VI (G=in the presence of an azodicarboxylate ester (typically dimethyl, diethyl, or diisopropyl) and a triarylphosphine (typically triphenylphosphine) in an inert solvent (such as tetrahydrofuran), as generally described by Mitsunobu, O. *Synthesis* (1981) 1.

SCHEME II

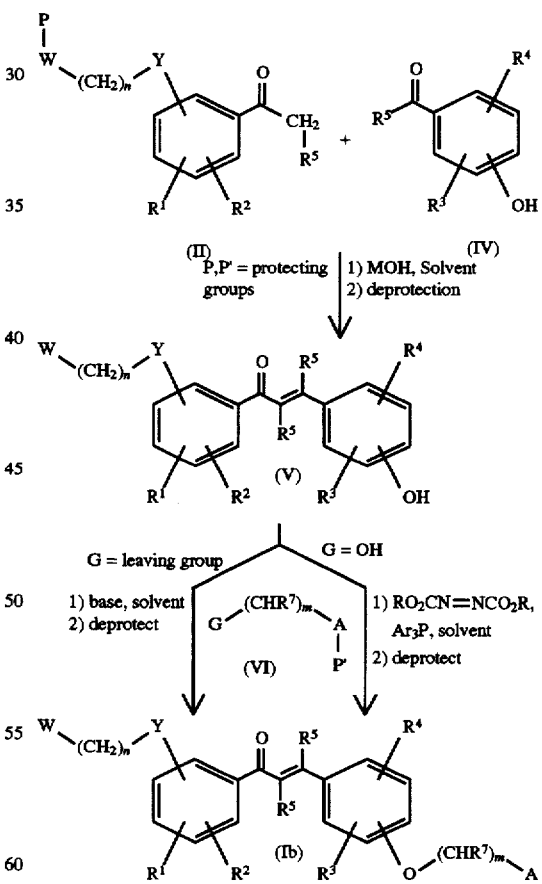

An alternate method for the preparation of compounds of Formula I, as shown in Scheme III, wherein $L^1$ is a bond, Z is C=O, and $L^2$ is a $C_2$ alkene involves treatment of suitably protected ketones of Formula (II) with suitably protected benzaldehydes of Formula (VII), a tetraalkoxysilane, typically tetramethoxysilane or tetraethoxysilane in the amount of half a molar equivalent, and a metal fluoride, typically cesium fluoride or potassium fluoride, in an inert solvent, typically N,N-dimethylformamide, at a temperature ranging from around 20° to 100° C. typically from 60° to 80° C. as has generally been described by Chuit et al. *Synthesis* 1983, 294. The resulting enone intermediate is then deprotected to give compound of Formula (Ic) according to Green, T. and Wuts, P. *Protective Groups in Organic Synthesis*, 2nd ed.; J. Wiley & Sons: New York, 1991.

tected aldehyde or ketone of Formula (III) and a strong base in an inert solvent. Deprotection of the resulting intermediate yields product of Formula (Id). Appropriate bases include, but are not limited to, alkali metal hydrides, such as sodium or potassium hydride, alkali metal amides, such as lithium diisopropyl amide or lithium or potassium bis (trimethylsilyl)amide, or metal carbonates, such as potassium carbonate. Appropriate solvents include ethers, such as tetrahydrofuran or dimethoxyethane, N,N-dialkylamides, such as N,N-dimethylformamide, lower alkylsulfoxides,

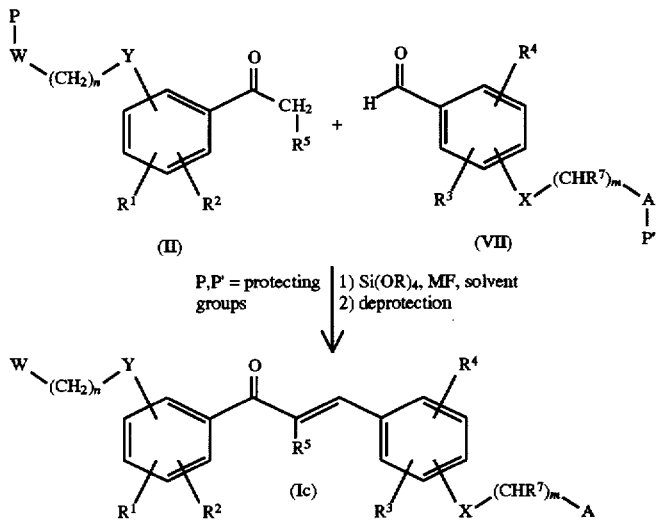

Alternatively, compounds of Formula I, wherein $L^1$ is a bond, Z is C=O, and $L^2$ is a $C_2$ alkene, may be prepared, as shown in Scheme IV, by treatment of a suitably protected D-ketophosphonate of Formula (VIII) with a suitably prosuch as dimethylsulfoxide, lower alkanenitriles, such as acetonitrile, or aromatic hydrocarbons, such as benzene, toluene, or xylenes. Reaction temperatures range from about −100° to 100° C.

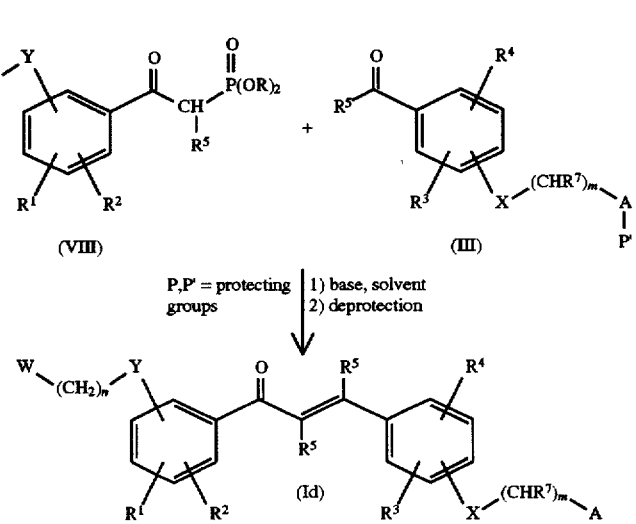

Compounds of Formula I, wherein L¹ is a bond, Z is C=O, and L² is a C₂ alkene, may also be prepared, as shown in Scheme V, by conversion of a suitably protected benzaldehyde of Formula (IX) into an oxime of Formula (X) under standard conditions, which is then further transformed in situ into a nitrile oxide of Formula (XI) in the presence of a styrene of Formula (XII) to form an isoxazoline of Formula (XIII). The isoxazoline (XIII) is then reduced and eliminated to form an enone, which after deprotection provides compounds of Formula (Ie). An excellent review of the methods and reaction conditions required for the nitrile oxide synthesis, its cycloaddition with olefins to form isoxazolines, and their reduction and hydrolysis to enones may be found in Torssell, K. B. G. *Nitrile Oxides, Nitrones, and Nitronates in Organic Synthesis*; VCH Publishers: New York, 1988.

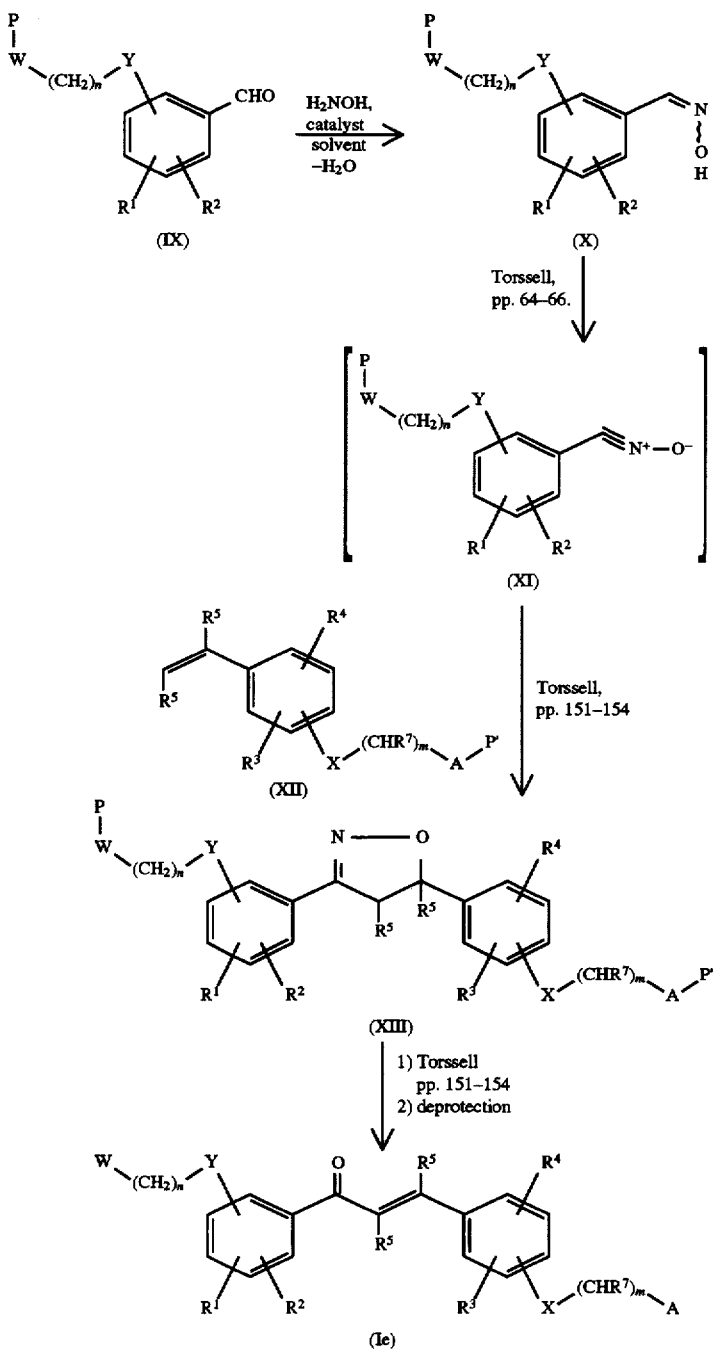

Compounds of Formula I wherein L¹ is a C₂ alkene, Z is C=O, and L² is a bond may be prepared, as shown in Scheme VI, by treating suitably protected compounds of Formula (XIV) and Formula (XV) with a metal hydroxide in an appropriate solvent at temperatures ranging from 0° to 200° C. followed by deprotection. The choice of solvent is the same as those described for the synthesis of compounds of Formula (Ia) in Scheme I.

SCHEME VI

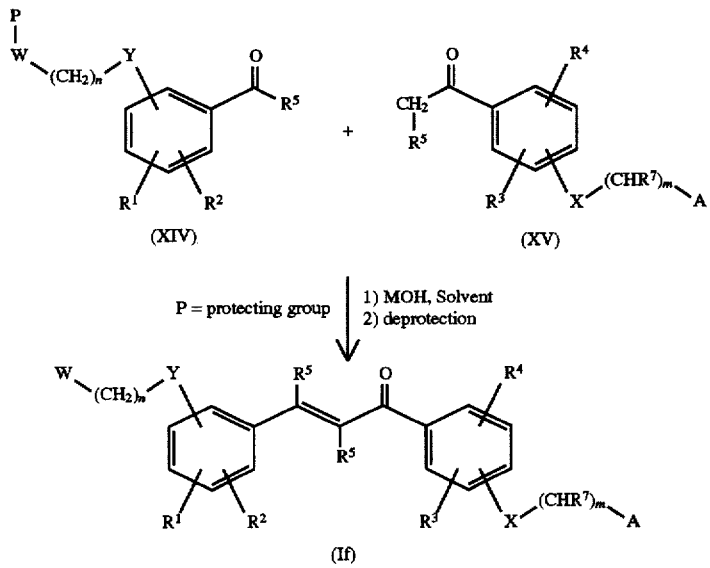

Compounds of Formula I wherein $L^1$ is a $C_2$ alkene, Z is C=O, $L^2$ is a bond, substituents $R^1$ and $R^2$ are sufficiently electron withdrawing, n=2–4, and Y=O, may be prepared, as shown in Scheme VII, by treating phenols of Formula (XVI) and suitably protected ketones of Formula (XV) and an excess amount of a metal hydroxide, typically 1.1 to 5 molar equivalents, in a solvent, such as methanol or ethanol, followed by acidic workup to yield the intermediate phenol of Formula (XVII). This phenol (XVII) may be converted to product (Ig) via either of two alkylation methods, similar to those described earlier for compound (Ib) in Scheme II, using here suitably protected compounds of Formula (XVIII), followed by final removal of protecting groups,

SCHEME VII

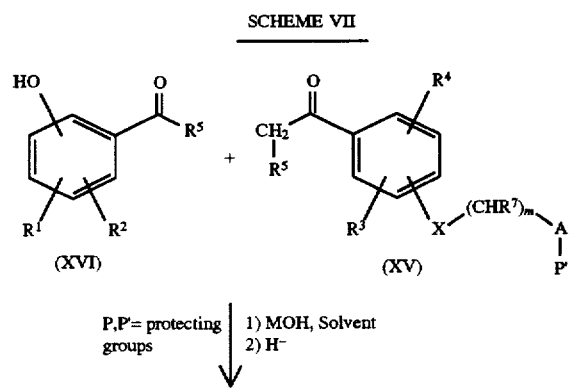

-continued
SCHEME VII

Alternatively, compounds of Formula I wherein $L^1$ is a $C_2$ alkene, Z is C=O, and $L^2$ is a bond may be prepared, as shown in Scheme VIII, by treating suitably protected benzaldehydes of Formula (XIX) with suitably protected ketones of Formula (XV), as shown in Scheme VIII, with a tetraalkoxysilane, a metal fluoride, and an inert solvent as described earlier for the synthesis of compounds (Ic) in Scheme III.

SCHEME VIII

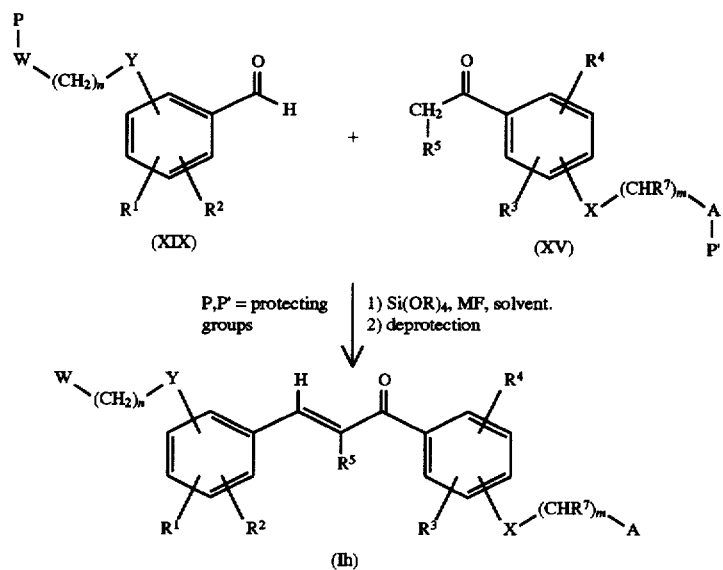

Alternatively, compounds of Formula I wherein $L^1$ is a $C_2$ alkene, Z is C=O, and $L^2$ is a bond may be prepared, as shown in Scheme IX, by treating suitably protected compounds of Formula (XIV) with a β-ketophosphonate of Formula (XX) and a strong base in an inert solvent. The selection of base, temperature, and solvent is the same as those described for the preparation of compounds of Formula (Id) in Scheme IV.

as shown in Scheme X, by conversion of a suitably protected benzaldehyde of Formula (XXI) into an oxime of Formula (XXII) under standard conditions. This oxime is then further transformed, as described earlier for Scheme V, in situ into a nitrile oxide of Formula (XXIII) in the presence of a styrene of Formula (XXIV) to form an isoxazoline of Formula (XXV). The isoxazoline (XXV) is then reduced and

SCHEME IX

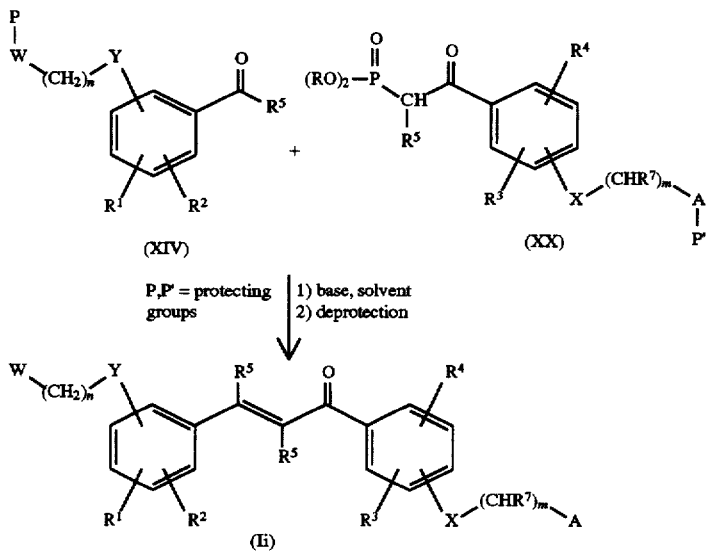

Alternatively, compounds of Formula I, wherein $L^1$ is a $C_2$ alkene, Z is C=O, and $L^2$ is a bond, may be prepared, eliminated to form an enone, which after deprotection provides compounds of type (Ij).

SCHEME X

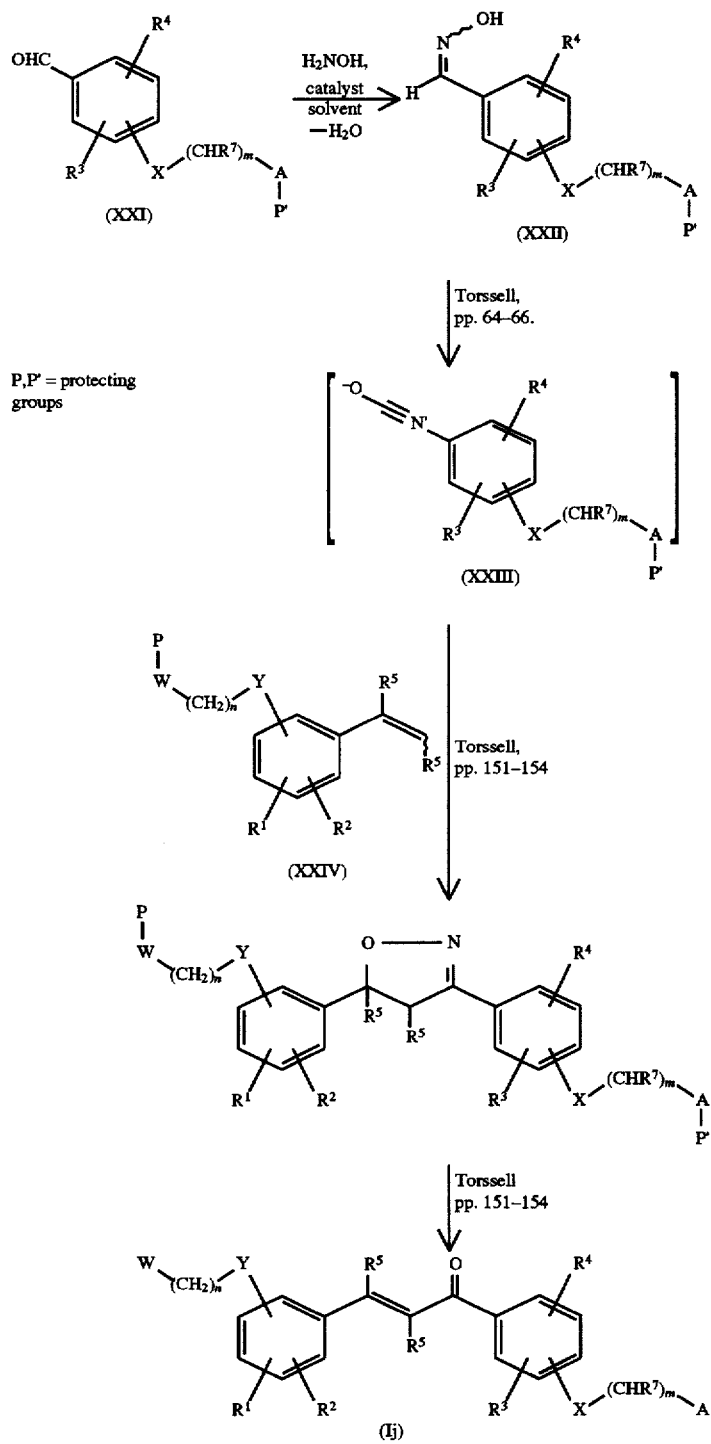

Suitably protected compounds of types (Ia–e) may be converted to compounds of type (Ik) wherein $L^1$ is a bond, $Z=O$, and $L^2$ is a $C_2$ alkyl by selective reduction of the C=C bond, followed by deprotection, as shown in Scheme XI. A host of methods are available for this reduction, including hydrogenation by a metal catalyst, dissolving metal reductions, and metal hydride additions. The choices of reagents and solvents are known to those skilled in the art, as has been reviewed in House, H. O. *Modern Synthetic Reactions*, 2nd ed.; Benjamin/Cummings: Reading, Mass., 1972, and Seyden-Penne, J. *Reductions by the Alumino-and Borohydrides in Organic Synthesis*; VCH Publishers: New York, 1991; pp 96–100.

SCHEME XI

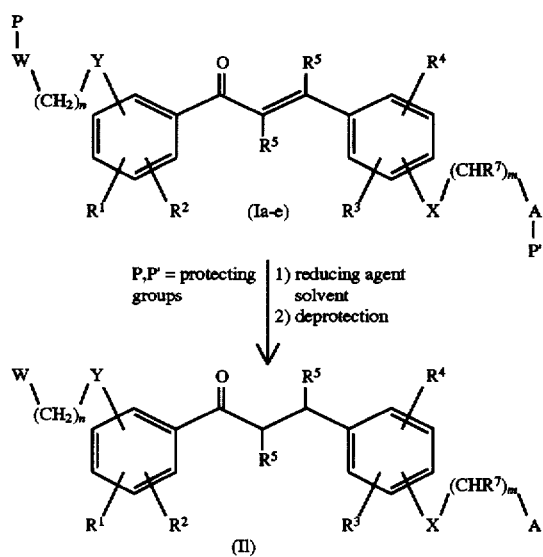

Compounds of Formula Z, wherein $L^1$ is a $C_2$ alkyl, Z=O, and $L^2$ is a bond may be prepared by the selective reduction of the C=C bond of suitably protected compounds (If–j), followed by deprotection, as shown in Scheme XII. Many methods are available for this reduction, including hydrogenation by a metal catalyst, dissolving metal reductions, and metal hydride additions, as described for compounds (II) immediately preceeding.

SCHEME XII

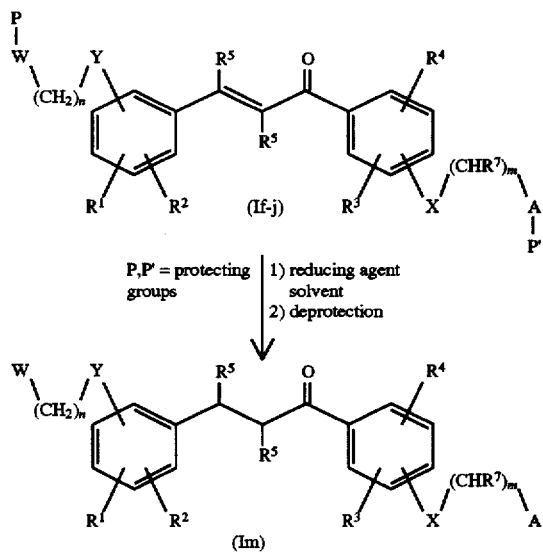

Compounds of this invention wherein $L^1$ is a bond, Z is $S(O)_p$ where p=0,1,2, and $L^2$ is a $C_2$ alkene may be prepared, as shown in Scheme XIII, by treating suitably protected compounds of Formula (XXVI) and Formula (III) in the presence of a strong base in an inert solvent, an temperatures from –100° to 200° C. The choice of the appropriate base will be known to those skilled in the art, and includes alkali metal hydrides, such as sodium or potassium hydride, alkali metal amides, such as lithium diisopropyl amide or potassium bis(trimethylsilyl)amide, or alkyllithiums, such as n-butyl lithium. Useful solvents include, but are not limited to, ethers, such as tetrahydrofuran or dimethoxyethane, or aromatic hydrocarbons, such as benzene, toluene, or xylenes. Preferred temperatures range from about –80° to 110° C. After deprotection, compounds of Formula (Ia) are obtained.

Those skilled in the art will realize that, in many instances, the intermediate hydroxy adduct (XXVII) may be isolated, which must then be eliminated to generate the alkene unit. A host of methods are generally known in the chemical literature for accomplishing such an elimination, such as treatment with a protonic or Lewis acid, or conversion of the —OH to a leaving group, such as an alkyl- or aryl-sulfonate, in the presence of a suitable base.

SCHEME XIII

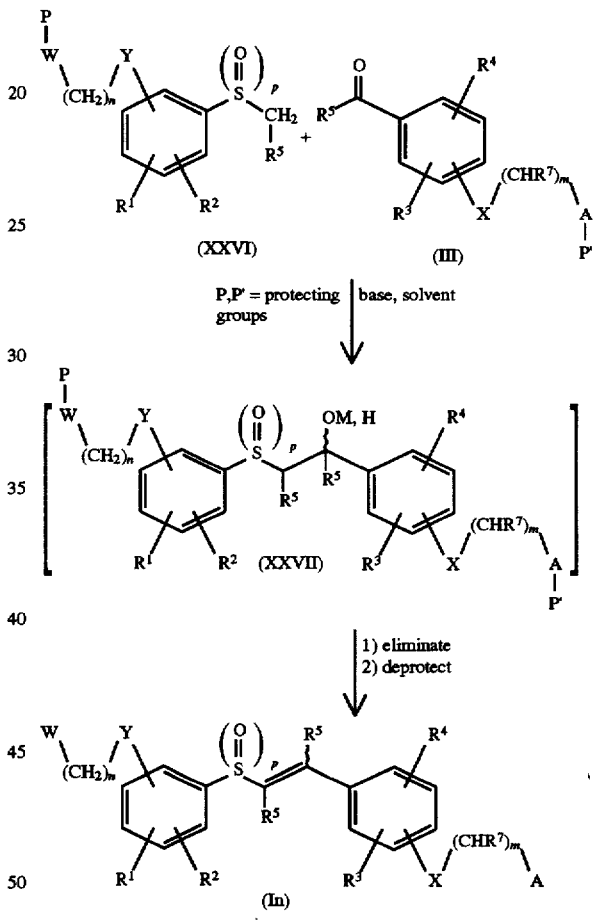

Compounds of this invention wherein $L^1$ is a bond, Z is $S(O)_p$ where p=0,1,2, and $L^2$ is a $C_2$ alkene may be prepared, as shown in Scheme XIV, by treating suitably protected compounds of Formula (XXVIII), where Q represents an activating/leaving group such as trialkylsilyl, —P(=O)(alkoxy)$_2$, —P(=O)(aryl)$_2$, —P(aryl)$_3$, —As(aryl)$_3$, or Cl, and Formula (III) in the presence of a suitable base in an inert solvent, at temperatures from –100° to 200° C. The choice of base includes, but is not limited to, alkali metal hydrides, such as sodium or potassium hydride, alkali metal amides, such as lithium diisopropyl amide or potassium bis(trimethylsilyl)amide, or alkyllithiums, such as n-butyl lithium. Useful solvents include, but are not limited to, ethers, such as tetrahydrofuran or dimethoxyethane, or aromatic hydrocarbons, such as benzene, toluene, or xylenes.

After deprotection, compounds of Formula (Io) are obtained.

SCHEME XIV

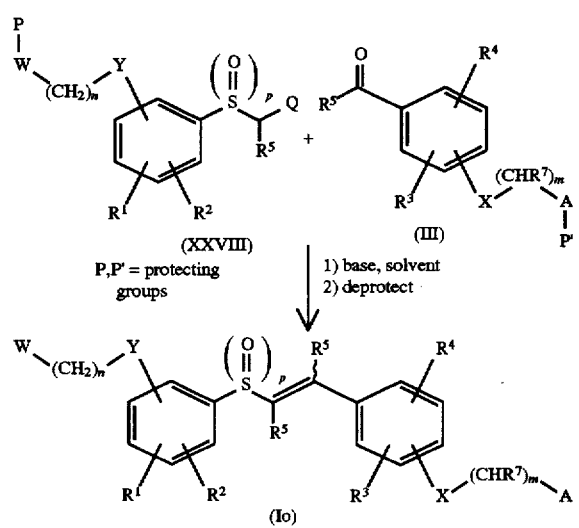

Compounds of Formula I, wherein $L^1$ is a single bond, $Z=SO_2$, and $L^2$ is a $C_2$ alkyne, may be prepared, as shown in Scheme XV, by treatment of suitably protected compounds of Formula (XXIX) with benzaldehydes (VII) in the presence of strong base in an inert solvent, conditions which have been generally reported by Lee, J. W.; Kim, T. H.; Oh, D. Y. *Synth. Commun.* 1989, 19, 2633. Deprotection provides product of Formula (Ip).

Compounds of this invention of Formula (I) wherein $L^1$ is a bond, Z is $S(O)_p$ where p=0, and $L^2$ is a $C_1$ to $C_4$ alkyl, nonconjugated (to the sulfur atom) $C_3$ or $C_4$ alkene or alkyne may be prepared, as shown in Scheme XVI, by treating suitably protected mercaptans of Formula (XXX) and alkylating agents (XXXI), wherein G is a good leaving group, in the presence of a base in an appropriate solvent, at temperatures from about −100° to 100° C. The choice of the appropriate base will be known to those skilled in the art, and includes metal hydroxides, metal alkoxides, metal carbonates, alkali metal hydrides, such as sodium or potassium hydride, or alkali metal amides, such as lithium diisopropyl amide or potassium bis(trimethylsilyl)amide. Useful solvents include, but are not limited to, water, lower alcohols, such as methanol or ethanol, ethers, such as tetrahydrofuran or dimethoxyethane, N,N-dialkylamides, such as N,N-dimethylformamide, sulfoxides, such as dimethylsulfoxide, or aromatic hydrocarbons, such as benzene, toluene, or xylenes. Leaving groups G in (XXXI) include halogens (especially Br, I), alkyl- or aryl-sulfonates, or perfluoroalkylsulfonates. After deprotection, compounds of Formula (Iq) are obtained.

SCHEME XVI

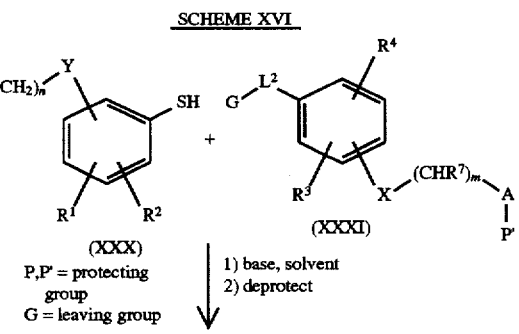

SCHEME XV

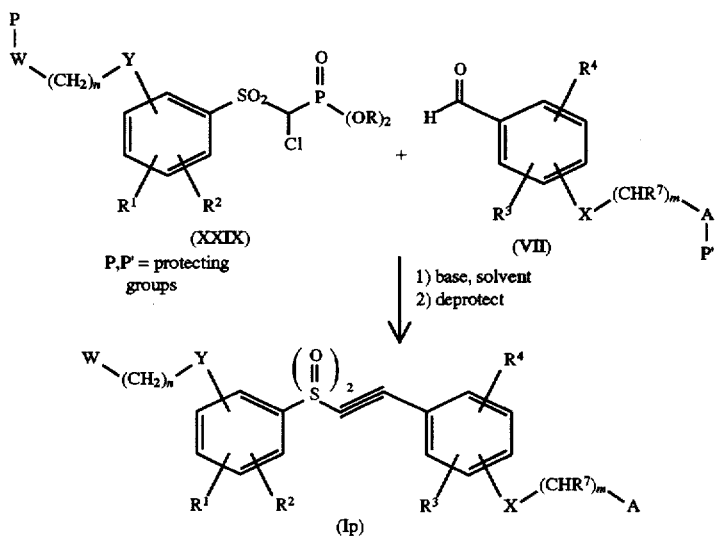

SCHEME XVI

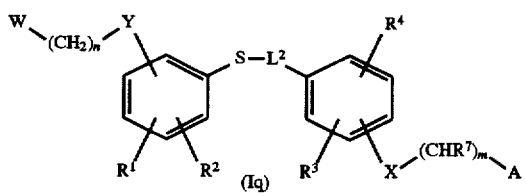

Compounds of this invention of Formula (I) wherein $L^1$ is a bond, Z is $S(O)_p$ where p=1 or 2, and $L^2$ is a $C_1$ to $C_4$ alkyl, nonconjugated (to the sulfur atom) $C_3$ or $C_4$ alkene or alkyne may be prepared, as shown in Scheme XVII, by treating suitably protected sulfides (Iq) with an oxidant in an appropriate solvent, followed by deprotection. Many methods are known in the chemical literature for the oxidation of sulfides to sulfoxides and sulfones, such as are found in the recent review by Hudlicky, M. *Oxidations in Organic Chemistry*; ACS Monograph 186; American Chemical Society: Washington, D.C., 1990; pp 252–262.

SCHEME XVII

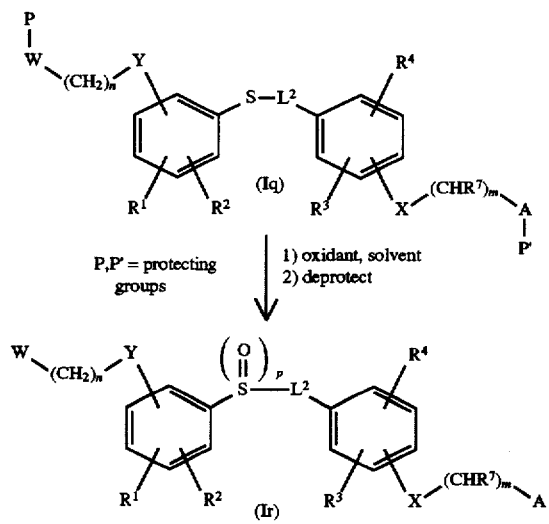

Compounds of this invention wherein $L^1$ is a $C_2$ alkene, Z is $S(O)_p$ where p=0, 1, or 2, and $L^2$ is a bond may be prepared, as shown in Scheme XVIII, by treating suitably protected compounds of Formula (XIV) and Formula (XXXII) in the presence of a strong base in an inert solvent, at temperatures from −100° to 200° C. The choice of base and solvent are the same as those described for Scheme XIII. Just as was described for Scheme XIII, the intermediate hydroxy adduct (XXXIII) may be isolated, which must be eliminated to generate the alkene unit. After deprotection, compounds of Formula (Is) are obtained.

SCHEME XVIII

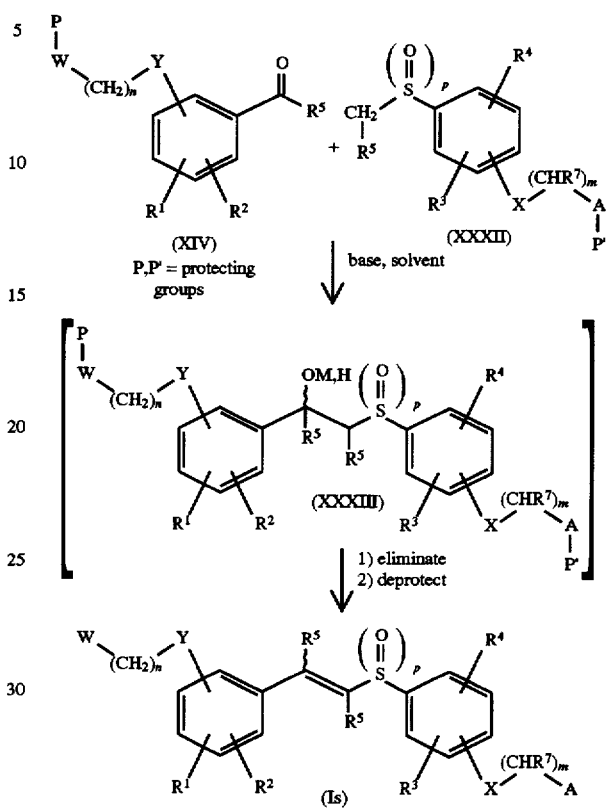

Alternatively, compounds of this invention wherein $L^1$ is a $C_2$ alkene, Z is $S(O)_p$ where p=0, 1, or 2, and $L^2$ is a bond may be prepared, as shown in Scheme XIX, by treating suitably protected compounds of Formula (XIV) and Formula (XXXIV), where Q represents an activating/leaving group such as trialkylsilyl, —P(=O)(alkoxy)$_2$, —P(=O)(aryl)$_2$, —P(aryl)$_3$, —As(aryl)$_3$, or Cl, in the presence of a strong base in an inert solvent, at temperatures from −100° to 200° C. The choice of base and solvent are the same as those described for Scheme XIV.

SCHEME XIX

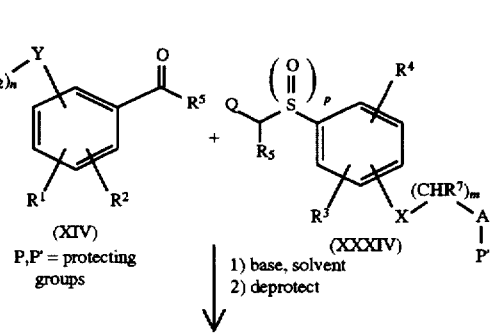

SCHEME XIX -continued

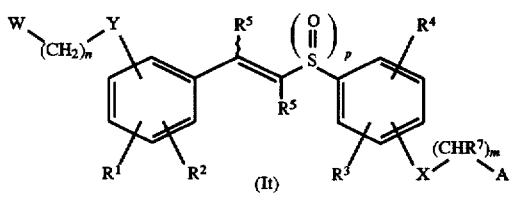

Compounds of this invention wherein $L^1$ is a $C_2$ alkyne, Z is $SO_2$, and $L^2$ is a bond may be prepared, as shown in Scheme XX, by treating suitably protected benzaldehydes of Formula (XIX) and sulfone chlorophosphonates of Formula (XXXV) in the presence of a strong base in an inert solvent under the Lee conditions cited in the discussion of Scheme XV. Final deprotection yields compounds (Iu).

SCHEME XX

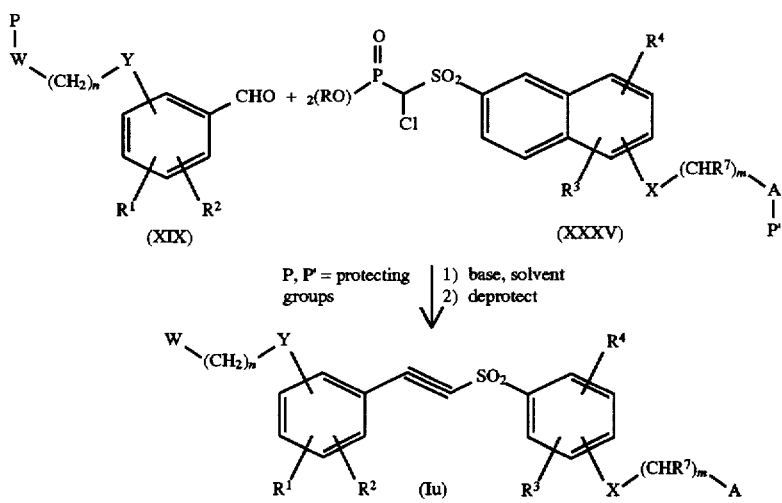

Compounds of this invention (I) wherein $L^1$ is a $C_1$ to $C_4$ alkyl, nonconjugated (to the sulfur atom) $C_3$ or $C_4$ alkene or alkyne, Z is $S(O)_p$ where p=0, and $L^2$ is a bond, may be prepared, as shown in Scheme XXI, by treating suitably protected mercaptans of Formula (XXXVI) and alkylating agents (XXXVII), wherein G is a good leaving group, in the presence of a base in an appropriate solvent, at temperatures from about −100° to 100° C. The choice of the appropriate base, solvent, and leaving group G are the same as those discussed for Scheme XVI. Deprotection yields compound of Formula (Iv).

SCHEME XXI

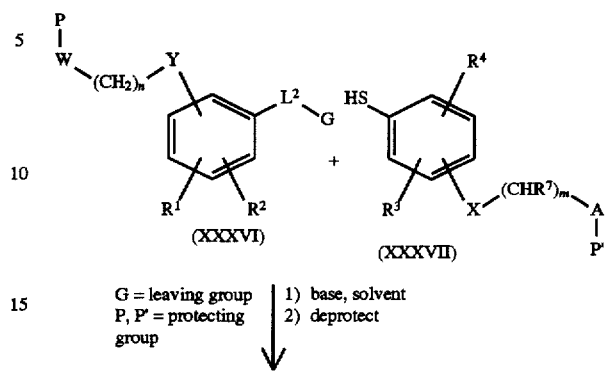

G = leaving group
P, P' = protecting group 1) base, solvent
2) deprotect

SCHEME XXI -continued

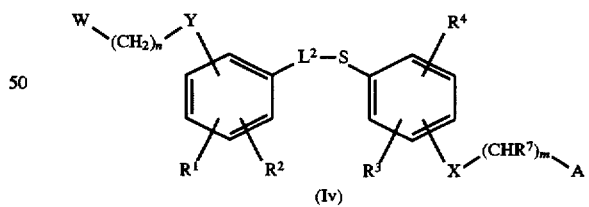

Compounds of this invention (I) wherein $L^1$ is a $C_1$ to $C_4$ alkyl, nonconjugated (to the sulfur atom) $C_3$ or $C_4$ alkene or alkyne, Z is $S(O)_p$ where p=1 or 2, and $L^2$ is a bond may be prepared, as shown in Scheme XXII, by treating suitably protected sulfides (Iv) with an oxidant in an appropriate solvent, followed by deprotection. The methods for the oxidation of sulfides to sulfoxides and sulfones are the same as those described for Scheme XVII.

SCHEME XXII

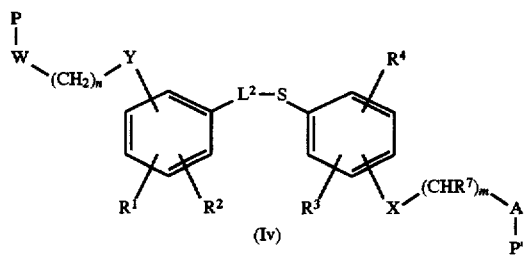
(Iv)

P, P' = protecting groups
1) oxidant, solvent
2) deprotect

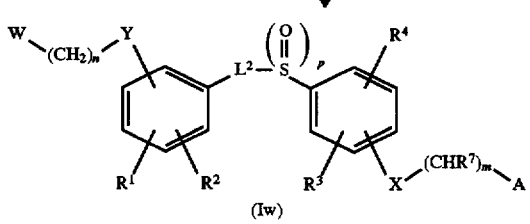
(Iw)

SCHEME XXIII

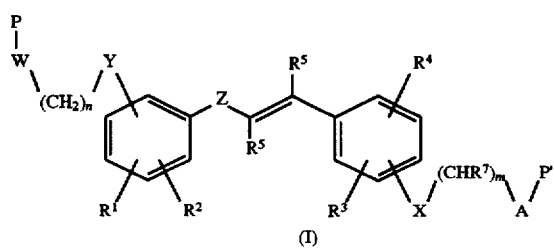
(I)

P, P" = protecting groups
1) 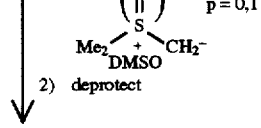 p = 0,1
2) deprotect

SCHEME XXIII -continued

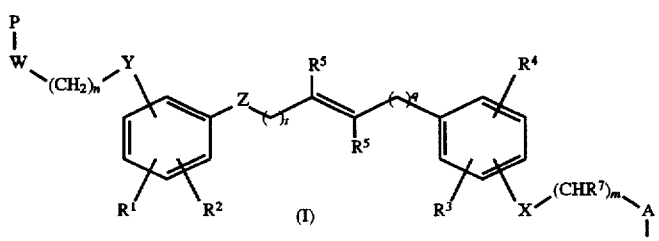
(Ix)

Suitably protected compounds of formula (I), where Z is (C=O), SO$_2$, or (S=O) may be converted into cyclopropyl compounds of formula (Ix), as shown in Scheme XXIII, by treatment with a sulfur ylide, such as dimethylsulfonium methylide or dimethylsulfoxonium methylide in a suitable solvent, such as DMSO, from about 0° to about 100° C. The ylides are prepared in situ from the analogous methylsulf (ox)onium salts upon treatment with a strong base, such as sodium hydride. The resulting cyclopropane is then deprotected in the usual way to give compounds of formula (Ix).

SCHEME XXIV

P, P" = protecting groups
q = 0,1
t = 0,1
1) Simmons-Smith cyclopropanation
2) deprotect

SCHEME XXIV -continued

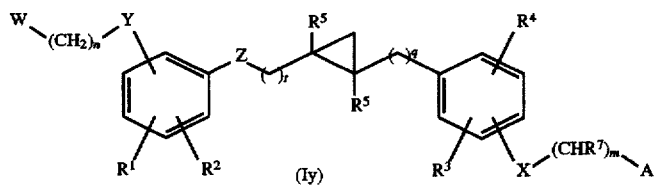

(Iy)

Compounds of formula (I) may be prepared, as shown in Scheme XXIV, by the Simmons-Smith cyclopropanation of a suitably protected alkene, typically using $CH_2I_2$ and Zn dust in an inert solvent, such as diethyl ether, from around room temperature to around 50° C. The cyclopropane product is then deprotected in the usual way to give compounds of formula (Iy).

SCHEME XXV

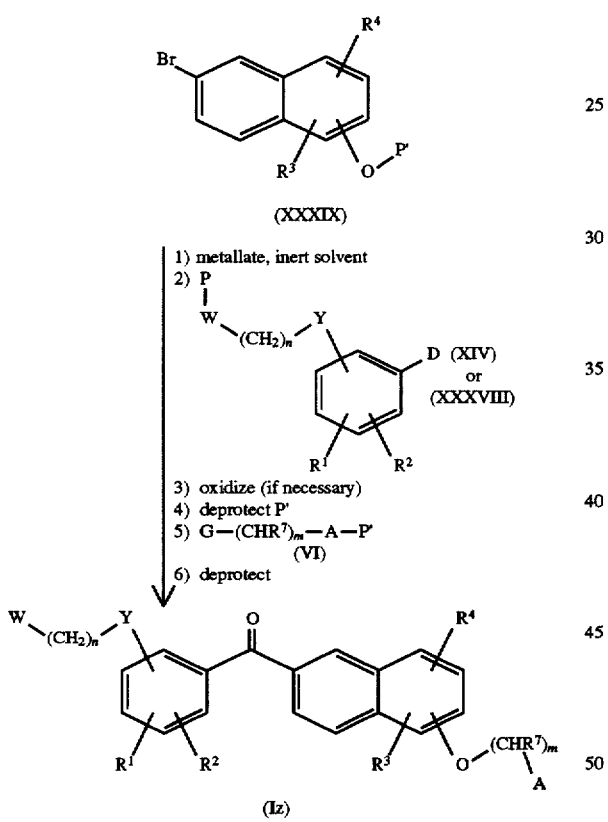

Certain compounds of formula (I) may be prepared as shown in Scheme XXV. A suitably protected 6-bromo-naphthol of formula (XXXIX) is converted to its corresponding naphthyllithium by treatment with a metallating agent, such as n-butyllithium, in an inert solvent, such as tetrahydrofuran, at low temperature, typically about −100° C. to about 0° C. The resulting lithiated naphthol intermediate is allowed to react with a suitably protected compound of formula XIV (where D is $(C=O)R^5$) or formula XXX-VIII (where D is CN), at temperatures ranging from −100° C. to 100° C. After aqueous work-up, a ketone bridge is formed from D=CN, while an alcohol is generated from D=$(C=O)R^5$. In those instances where the alcohol is formed, it must then be oxidized by any of a multitude of methods such as a Swern oxidation, into the ketone. The hydroxyl protecting group P' is then cleaved under the appropriate conditions to produce the naphthol. The naphthol is then allowed to react with a compound of formula (VI) as has been described earlier for the analogous phenolic alkylation in Scheme II. Final deprotection in the usual way provides compounds of formula (Iz).

SCHEME XXVI

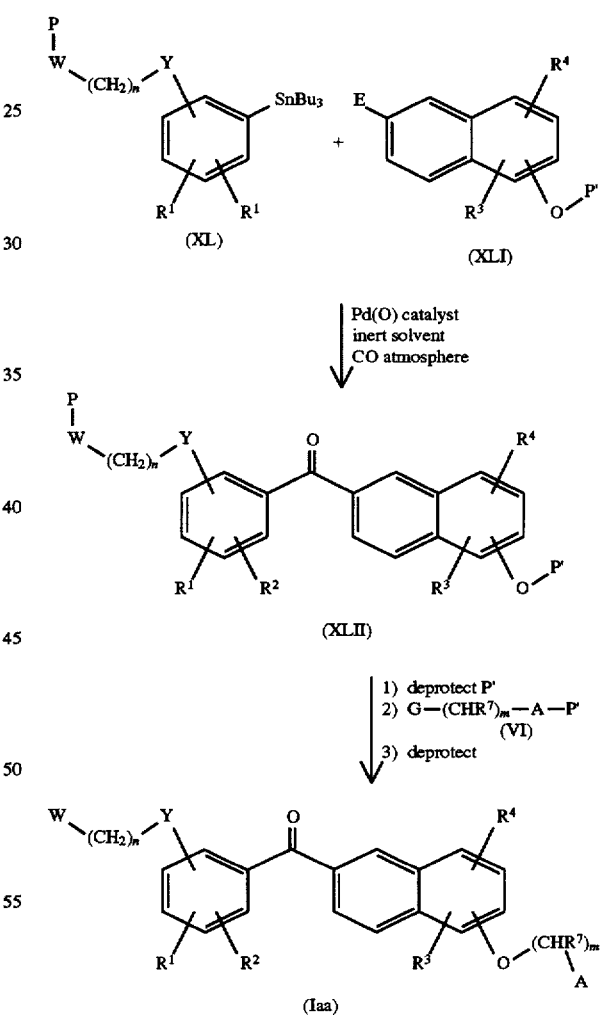

Certain compounds of formula (I) may be prepared as shown in Scheme XXVI. A suitably protected phenyl tributylstannane of formula (XL) is allowed to react with a suitably protected compound of formula (XLI), wherein E may be Br, I, $OSO_2CF_3$ or $(C=O)Cl$, in an inert solvent, such as toluene or benzene, under an atmosphere of carbon monoxide at elevated temperature in the presence of an appropriate palladium (0) catalyst, such as tetrakis (triphenylphosphine)palladium (0). The resulting ketone of formula (XLII) is converted to the target compound of formula (Iaa) via the same sequence of steps as described in Scheme XXV.

The following examples further illustrate details for the preparation of the compounds of the present invention. Those skilled in the are will readily understand that known variations of the conditions and processes of the following preparative procedures can be used to prepare the compounds of the present invention. All temperatures are degrees Celsius unless otherwise noted.

EXAMPLES

Representative examples were prepared by the methods see forth below.

Example 1

(E)-4-[3-((3-(2-Aminoethoxy)phenyl))-3-oxo-1-propenyl]phenoxyacetic acid.hydrochloride.

1a) 3'-(2-Hydroxyethoxy)acetophenone

3'-Hydroxyacetophenone (5.0 g, 37 mmol), potassium carbonate (6.1 g, 44 mmol), sodium iodide (0.28 g, 1.8 mmol), and 2-bromoethanol (2.6 mL, 37 mmol) were stirred in N,N-dimethylformamide (DMF) for 20 h at room temperature, then for 4 days at 70°–80° C. The reaction mixture was diluted with ethyl acetate (EtOAc) and extracted several times with water, then dried over magnesium sulfate ($MgSO_4$), and concentrated in vacuo. Chromatography on silica gel, eluting with 30% to 50% EtOAc in hexanes, after solvent removal, gave a viscous oil (2.1 g). $^1$H-NMR (300 MHz, $CDCl_3$): 7.56 (d, 1H, J=8 Hz), 7.51(s, 1H), 7.39(t, 1H, J=8 Hz), 7.14(d, 1H, J=8 Hz), 4.14 (m, 2H), 3.99 (m, 2H), 2.60 (s, 3H), 2.09 (br, 1H).

1b) 3'-(2-p-Toluenesulfonyloxyethoxy)acetophenone

A solution of p-toluenesulfonic anhydride (3.6 g, 11 mmol) in dichloromethane ($CH_2Cl_2$, 36 mL) was added dropwise over 1 h to a solution of 3'-(2-hydroxyethoxy) acetophenone (1.5 g, 8.3 mmol) and triethylamine (1.7 mL, 12 mmol) in $CH_2Cl_2$ (76 mL). After stirring at room temperature overnight, the solvent was evaporated in vacuo. The residue was extracted with water, 1M hydrochloric acid, saturated aqueous sodium bicarbonate, and brine. Drying ($MgSO_4$), and solvent removal gave the crude tosylate as a gum (2.9 g), which was not purified. $^1$H-NMR(300 MHz, $CDCl_3$): 7.8 (d, 2H), 7.55 (d, 1H), 7.4 (m, 4H), 7.0 (d, 1H), 4.4 (m, 2H), 4.2 (m, 2H), 2.6 (s, 3H), 2.45 (s, 3H).

1c) 3'-[2-(N,N-Bis-t-butyloxycarbonyl)aminoethoxy]acetophenone

Crude tosylate 1b (2.9 g, 8.3 mmol) and di-t-butyliminodicarboxylate, potassium salt (2.2 g, 8.4 mmol) were stirred in DMF at room temperature for 65 h, then diluted with EtOAc and extracted several times with water. After drying ($MgSO_4$) and solvent removal, the product was chromatographed on silica gel, eluting with 20–40% EtOAc in hexanes. Solvent removal gave an oil (3.2 g). $^1$H-NMR (300 MHz, $CDCl_3$): 7.54 (d, 1H, J=8 Hz), 7.47 (m, 1H), 7.36 (t, 1H, J=8 Hz), 7.10 (m, 1H), 4.18 (t, 2H, J=6 Hz), 4.03 (t, 2H, J=6 Hz), 2.59 (s, 3H), 1.51 (s, 18H).

1d) 4-[3-((3-(2-t-(Butyloxycarbonylaminoethoxy)phenyl))-3-oxo-1-propenyl]phenoxyacetic acid The N-protected acetophenone 1c (1.5 g, 3.9 mmol), 4-formylphenoxyacetic acid (0.70 g, 3.9 mmol), and sodium hydroxide (0.32 g, 8.0 mmol) were heated at reflux in methanol (30 mL) for 8 days. After cooling and solvent removal, the residue was extracted with EtOAc and 5% aqueous $KHSO_4$. After drying ($MgSO_4$) and solvent removal, the product was chromatographed on silica gel, eluting with 10–20% methanol in chloroform. Solvent removal gave a solid (0.77 g). $^1$H-NMR(300 MHz, $d_6$-DMSO): 7.79 (d, 2H, J=8 Hz), 7.71 (m, 3H), 7.58 (s, 1H), 7.46 (m, 1H), 7.21 (d, 1H, J=8 Hz), 7.05 (br, 1H), 6.90 (d, 2H, J=9 Hz), 4.35 (s, 2H), 4.04 (m, 2H), 3.33(m, 2H), 1.38 (s, 9H). HR-MS: Calc. 442.1866, Found 442.1860.

1e) (E)-4-[3-((3-(2-Aminoethoxy)phenyl))-3-oxo-1-propenyl]phenoxyacetic acid.hydrochloride A mixture of N-BOC amine 1d (0.20 g, 0.45 mmol) and 4M hydrogen chloride in 1,4-dioxane (1.0 mL) was stirred at room temperature under a $CaSO_4$ drying tube for 3.3 h. Dilution with diethyl ether produced a precipitate, which was collected by filtration and dried to give a yellow powder (0.17 g). $^1$H-NMR(300 MHz, $d_6$DMSO): 13.1 (br, 1H), 8.09 (br, 3H), 7.87–7.82 (m, 3H), 7.78 and 7.74 (AB quartet, 2H, J=15 Hz), 7.63 (s, 1H), 7.53 (t, 1H, J=8 Hz), 7.28 (rid, 1H, J=8,2 Hz), 7.01 (d, 2H, J=9Hz), 4.78 (s, 2H), 4.30–4.26 (m, 2H), 3.36 (br, 2H). HR-MS: Calc. 342.1341, Found 342.1349. IR(KBr) $cm^{-1}$ 3398, 1744, 1656.

Example 2

(E)-Ethyl 5-[3-((3-(2-aminoethoxy)phenyl))-3-oxo-1-propenyl]-2-(carboxymethoxy)benzoate.trifluoroacetate 2a) Methyl 3-[2-(t-butyloxycarbonylamino)ethoxy]benzoate Methyl 3-hydroxybenzoate (1.0 g, 6.7 mmol), N-BOC-2-aminoethanol (1.0 g, 6.7 mmol), triphenylphosphine (1.8 g, 6.7 mmol), and diisopropylazodicarboxylate (1.4 mL, 6.7 mmol) were stirred in tetrahydrofuran (THF) at −20° C. under nitrogen for around 6 hours, then at room temperature overnight. After removal of solvent in vacuo, the mixture was chromatographed on silica gel, eluting with 0% to 35% EtOAc in hexanes. Removal of solvent gave a pale yellow, viscous oil (1.9 g) which was contaminated with a small amount of the unreacted starting phenol. $^1$H-NMR(300 MHz, $CDCl_3$): 7.67–7.08 (m, 4H), 5.16 (br, 1H), 4.07 (t, 2H, J=5 Hz), 3.92 (s, 3H), 3.58–3.53 (m, 2H), 1.46 (s, 9H), IR(neat) $cm^{-1}$ 3376, 1722.

2b) Dimethyl 2-[3-((2-(N-1-butyloxycarbonyl)aminoethoxy]))phenyl]-2-oxo-ethylphosphonate Diisopropylamine (1.4 mL, 10 mmol) was added dropwise via syringe over 3 min to a solution of n-butyllithium (1.6M in hexanes, 5.8 mL, 9.2 mmol) in dry THF at −60° C. with stirring under nitrogen. After 15 min, a solution of dimethyl methylphosphonate (0.66 mL, 6.1 mmol) in THF (5 mL) was added via cannula. After 10 min, a solution of methyl ester 2a (1.8 g, 6.1 mmol) in THE (5 mL) was introduced via cannula over about 1 min. After stirring for another 10 min at −60° C., the cold bath was replaced with an ice water bath. After 20 min, the reaction was quenched by adding 1M HCl (20 mL). The mixture was immediately extracted with EtOAc. The organic layer was extracted further with water (2×), then brine, and dried ($MgSO_4$). After solvent removal, the crude product was chromatographed on silica gel, eluting with EtOAc. Solvent removal gave a viscous yellow oil (0.76 g). $^1$H-NMR(300 MHz, $CDCl_3$): 7.60 (dt, 1H, J=8,1 Hz), 7.53 (t, 1H, J=3 Hz), 7.40 (t, 1H, J=8 Hz), 7.14 (ddd, 1H, J=8, 3, 1 Hz), 5.00 (br, 1H), 4.10–4.06 (m, 2H), 3.79 (d, 6H, J=11 Hz), 3.63 (d, 2H, J=23 Hz), 3.58–3.52 (m, 2H), 1.45 (s, 9H). Anal. Calc'd for $Cl_{17}H_{26}NO_7P$: C, 52.71; H, 6.77; N, 3.62; Found: C, 52.49; H, 6.97; N, 3.35.

2c) Ethyl 5-formyl-2-hydroxybenzoate

5-Formylsalicylic acid (3.0 g, 17 mmol), conc. sulfuric acid (1 mL) and absolute ethanol (100 mL) were heated at reflux for 3.5 days with stirring under $N_2$. The reaction was cooled, then carefully quenched by adding saturated sodium bicarbonate (40 mL). Solvent was removed in vacuo, and the resulting mixture was acidified with 1M HCl (50 mL), then extracted with EtOAc. The organic phase was extracted with water, then brine, and dried (MgSO$_4$). Removal of solvent and chromatography on silica gel, eluting with 0% to 25% EtOAc in hexanes gave a colorless crystalline solid (2.3 g), mp 67°–69° C. after solvent removal. $^1$H-NMR(300 MHz, CDCl$_3$): 11.49 (s, 1H), 9.90 (s, 1H), 8.40 (d, 1H, J=2 Hz), 8.00 (dd, 1H, J=8.2 Hz), 7.11 (d, 1H, J=8 Hz), 4.48 (q, 2H, J=7 Hz), 1.46 (t, 3H, J=7 Hz). IR(KBr): cm$^{-1}$ 3186, 1684.

2d) Ethyl 2-[2-(t-butyloxy)-2-oxo-ethoxy]-5-formylbenzoate

Phenol 2c (1.0 g, 5.2 mmol), C-butyl bromoacetate (0.84 mL, 5.2 mmol), and potassium carbonate (0.79 g, 5.7 mmol) were heated at 65° C. in DMF (8 mL) overnight. After solvent removal, the mixture was diluted with EtOAc and extracted with water (3×), then brine. Drying (MgSO$_4$) and removal of solvent gave a clear yellow oil (1.56 g). $^1$H-NMR (300 MHz, CDCl$_3$): 9.93 (s, 1H), 8.35 (d, 1H, J=2 Hz), 7.99 (dd, 1H, J=9.2 Hz), 6.95 (d, 1H, J=9 Hz), 4.71 (s, 2H), 4.41 (q, 2H, J=7 Hz), 1.48 (t, 3H, J=7 Hz). Anal. Calc'd for C$_{16}$H$_{20}$O$_6$: C, 62.33; H, 6.54; Found: C, 62.05; H, 6.58.

2e) (E)-Ethyl 5-[3-((3-(2-t-butyloxycarbonylamino)-ethoxyphenyl))-3-oxo-1-propenyl]-2-[2-(t-butyloxy)-2-oxo]ethoxybenzoate Sodium hydride (60% oil disp., 26 mg, 0.65 mmol) was added to a solution of β-ketophosphonate 2b (0.25 g, 0.65 mmol) and aldehyde 2d (0.20 g, 0.65 mmol) in dry THF (5 mL) with stirring at room temperature. After 19 h, solvent was removed under a rapid stream of N$_2$. The mixture was diluted with EtOAc and extracted with water (2×), then brine, and dried (MgSO$_4$). After solvent removal, the residue was chromatographed on silica gel, eluting with 0% to 50% EtOAc in hexanes. After solvent removal, a yellow gum (0.24 g) was obtained. $^1$H-NMR(300 MHz, CDCl$_3$): 8.12 (d, 1H, J=2 Hz), 7.77 (d, 1H, J=16 Hz), 7.71 (dd, 1H, J=9.2 Hz), 7.62 (d, 1H, J=8 Hz), 7.54–7.52 (m, 1H), 7.43 (d, 1H, J=16 Hz), 7.42 (t, 1H, J=8 Hz), 7.13 (dd, 1H, J=8.2 Hz), 6.89 (d, 1H, J=9 Hz), 5.00 (br, 1H), 4.66 (s, 2H), 4.42 (q, 2H, J=7 Hz), 4.13–4.09 (m, 2H), 3.60–3.55 (m, 2H), 1.49 (s, 9H). MS(NH$_3$): 587 (base, M+NH$_4$).

2f) (E)-Ethyl 5-[3-((3-(2-aminoethoxy)phenyl))-3-oxo-1-propenyl]-2-(carboxymethoxy)benzoate.trifluoroacetate Trifluoroacetic acid (1 mL) was added to a solution of substrate 2e (0.24 g, 0.42 mmol) in dichloromethane (3 mL) with stirring at room temperature under a CaSO$_4$ tube. After 80 minutes, diethyl ether was added, which led to precipitate formation. The precipitate was collected by filtration and dried under high vacuum to give a yellow powder (0.17 g). $^1$H-NMR(300 MHz, d$_6$-DMSO): 8.10 (d, 1H, J=2 Hz), 7.97 (dd, 1H, J=9.2 Hz), 7.87–7.80 (m, 3H), 7.72 (d, 1H, J=16 Hz), 7.61 (br s, 1H), 7.53 (t, 1H, J=8 Hz), 7.28 (dd, 1H, J=8.2 Hz), 7.03 (d, 1H, J=9 Hz), 4.68 (s, 2H), 4.33–4.24 (m, 4H), 3.25 (m, 2H), 1.32 (t, 3H, J=7 Hz). IR(KBr): cm$^{-1}$ 3300–2300, 1736, 1686, 1658.

Example 3
(E)-Ethyl 5-[3-((2-(1-prop-2-enyloxy)-5-(2aminoethoxy)phenyl))-3-oxo-1-propenyl]-2-(carboxymethoxy)benzoate.trifluoroacetate.

3a) Methyl 2,5-dihydroxybenzoate 2,5-Dihydroxybenzoic acid was converted to its methyl ester using catalytic sulfuric acid in methanol following the same protocol as for esterification 2c in 94% yield. mp 86.4°–88.5° C. IR(KBr): cm$^{-1}$ 3346, 1684.

3b) Methyl 5-(2-t-butyloxycarbonylamino)ethoxy-2-hydroxybenzoate

Methyl 2,5-dihydroxybenzoate was converted to its 5-(N-BOC-aminoethoxy) adduct following the Mitsunobu coupling protocol used in the preparation of 2a (53% yield). 1H-NMR(300 MHz, CDCl$_3$): 90% pure, 10.38 (s, 1H), 7.28 (d, 1H, J=3 Hz), 7.06 (dd, 1H, J=9.3 Hz), 6.90 (d, 1H, J=9 Hz), 5.00 (br, 1H), 3.97 (t, 2H, J=5 Hz), 3.94 (s, 3H), 3.50 (m, 2H), 1.44 (s, 9H).

3c) Methyl 5-(2-t-butyloxycarbonylamino)ethoxy-2-1-prop-2-enyloxy)benzoate

Phenol 3b (3.94 g, 12.7 mmol), allyl bromide (1.2 mL, 14 mmol), and potassium carbonate (1.95 g, 14 mmol) were heated to 45°–55° C. in DMF. After 4 days, TLC indicated incomplete reaction, so more allyl bromide was added (0.5 mL). After 3 more days, still more allyl bromide (0.75 mL) was added. The next day, the reaction was worked up and chromatographed on silica gel, eluting with 0% to 40% EtOAc in hexanes. After removal of solvent, an oil (2.7 g) was obtained. $^1$H-NMR(300 MHz, CDCl$_3$): 7.34 (d, 1H, J=3 Hz), 7.00 (dd, 1H, J=9.3 Hz), 6.92 (d, 1H, J=9 Hz), 6.12–6.00 (m, 1H), 5.51–5.27 (m, 2H), 4.98 (br, 1H), 4.59–4.56 (m, 2H), 4.00 (t, 2H, J=5 Hz), 3.90 (s, 3H), 3.55–3.51 (m, 2H), 1.45 (s, 9H). HR-MS: Calc'd. 369.2026, Found 369.2014.

3d) Dimethyl 2-[3-((2-(N-1-butyloxycarbonylamino)ethoxy))-2-(1-prop-2-enyloxy)phenyl]-2-oxo-ethylphosphonate Methyl ester 3c was converted to a dimethyl β-ketophosphonate according to the procedure used for the synthesis of 2b in 46% yield as an oil. $^1$H-NMR(300 MHz, CDCl$_3$): 7.27 (d, 1H, J=2 Hz), 7.03 (dd, 1H, J=9.2 Hz), 6.90 (d, 1H, J=9 Hz), 6.13–6.04 (m, 1H), 5.44–5.31 (m, 2H), 4.90 <br, 1H), 4.62 (d, 2H, J=6 Hz), 3.99 (t, 2H, J=5 Hz), 3.88 (d, 2H, J=21 Hz), 3.75 (d, 6H, J=11 Hz), 3.54–3.49 (m, 2H), 1.45 (s, 9H). HR-MS: Calc'd. 461.2053, Found 461.2063.

3e) (E)-Ethyl 5-[3-((5-(2-t-butyloxycarbonylamino)-ethoxy-2-(1-prop-2enyloxy)phenyl))-3-oxo-1-propenyl]-2-[2-(t-butyloxy)-2oxo]ethoxybenzoate Aldehyde 2d and D-ketophosphonate 3d were condensed using the conditions described for the synthesis of 2e to give a yellow oil in 20% yield. HR-MS: Calc'd. 626.2965, Found 626.2964.

3f) (E)-Ethyl 5-[3-((2-(1-prop-2-enyloxy)-5-(2-aminoethoxy)phenyl ))-3-oxo-1-propenyl]-2-carboxymethoxy)benzoate.trifluoroacetate Chalcone 3e was deprotected using trifluoroacetic acid in CH$_2$Cl$_2$ as described for 2f to yield a yellow solid (76%). HR-MS: Calc'd. 470.1815, Found 470.1810.

Example 23
(E)-4-[3-((3-(2-Aminoethoxy))phenyl))-3-oxo-1-propenyl]-2-methoxyphenoxyacetic acid.trifluoroacetate 23a) 3-Methoxy-4-(2-t-butyloxy-2-oxo-ethoxy)benzaldehyde Vanillin was alkylated with t-butyl bromoacetate in DMF in the presence of potassium carbonate the usual way to give a waxy solid. (quant.) mp 86.8°–90° C. MS(NH$_3$): 284 (base, M+NH$_4$).

23b) (E)-[-Butyl 4-[3-((3-(2-t-butyloxycarbonylamino)-ethoxyphenyl))-3-oxo-1-propenyl]-2-methoxyphenoxyacetate A solution of potassium t-butoxide in t-butanol (1M, 1.3 mL, i.3 mmol) was added dropwise to a stirred solution of β-ketophosphonate 2b (0.50 g, 1.3 mmol) in dry THF (20 mL) at room temperature. After 2 h, aldehyde 5a (0.34 g, 2.6 mmol) was added. After stirring overnight, the reaction was quenched with 5% aq. KHSO$_4$, then extracted with EtOAc. The organic layer was further extracted with water, then dried (Na$_2$SO$_4$ and concentrated. The product was purified by chromatography on silica gel, eluting with 0% to 40% EtOAc in hexanes. After solvent removal, a yellow oil was obtained (0.16 g). MS(NH$_3$): 545 (M+NH$_4$), 528 (M+H).

23c) (E)-4-[3-((3-(2-Aminoethoxy)phenyl))-3-oxo-1-propenyl]-2-methoxyphenoxyacetic acid.trifluoroacetate Substrate 23b was deprotected with trifluoroacetic acid/dichloromethane in the usual way to give a yellow solid (0.12 g). MS(NH$_3$): 372 (base, M+H). mp. 195°–198° C.

Example 24
(E)-n-Butyl 5-[3-((3-(2-aminoethoxy)-phenyl))-3-oxo-1-propenyl]-2-(carboxymethoxy)benzoate -trifluoroacetate 24a) n-Butyl 5-formyl-2-hydroxybenzoate 5-Formylsalicylic acid (5.0 g, 30 mmol), n-butyl iodide (3.4 mL, 30 mmol), and potassium carbonate (4.2 g, 30 mmol) were stirred in DMF (40 mL) for 27 h at room temperature. After several EtOAc/H$_{2}$O extractions, the mixture was dried (MgSO$_4$), and concentrated. Chromatography on silica gel, eluting with 5% to 30% EtOAc in hexanes, followed by solvent removal gave a white solid (2.0 g). HR-MS: Calc'd 223.0970, Found 223.0968. Anal. Calc'd for C$_{12}$H$_{14}$O$_4$: C, 64.84; H, 6.36; Found: C, 64.82; H, 6.30.

24b) (E)-n-Butyl 5-[3-((3-(2-aminoethoxy)phenyl))-3-oxo-1-propenyl]-2-(carboxymethoxy)benzoate.trifluoroacetate Phenol 24a was converted, via the usual sequence of steps, into final produce 24b as a solid. HR-MS: Calc'd 442.1866, Found 442.1851.

Example 36
(E)-Methyl 5-[3-((3-(2-aminoethoxy)-phenyl))-3-oxo-1-propenyl]-2-(carboxymethoxy)-3-(1-prop-2-enyl) benzoate.trifluoroacetate 36a) Methyl 5-formyl-2-(1-prop-2-enyloxy)benzoate Methyl 5-formylsalicylate (3.3 g, 18 mmol), allyl bromide (1.7 mL, 20 mmol), and potassium carbonate (2.8 g, 20 mmol) were stirred at room temperature in DMF (20 mL) overnight. After concentration, the mixture was diluted with EtOAc and extracted with water (5×), then brine. After drying (MgSO$_4$), solvent was removed to give a yellow solid (4.2 g). $^1$H-NMR(300 MHz, CDCl$_3$): 9.92 (s, 1H), 8.35 (d, 1H, J=2 Hz), 8.00 (dd, 1H, J=9,2 Hz), 7.09 (d, 1H, J=9 Hz), 6.13–6.01 (m, 1H), 5.58–5.34 (m, 2H), 4.75–4.73 (m, 2H), 3.93 (s, 3H). Anal. Calc'd for C$_{12}$H$_{12}$O$_4$: C, 65.45; H, 5.49; Found: C, 65.10; H, 5.36.

36b) Methyl 5-formyl-2-hydroxy-3-(1-prop-2enyl) benzoate

Allyl ether 36a was heated neat to ca. 175° C. overnight with stirring under N$_2$. After cooling, the product was purified by chromatography on silica gel, eluting with 0% to 30% EtOAc in hexanes. Solvent was removed to give a yellow oil (50% yield). $^1$H-NMR(300 MHz, CDCl$_3$): 11.68 (s, 1H), 9.85 (s, 1H), 8.27 (d, 1H, J=2 Hz), 7.88–7.87 (m, 1H), 6.06–5.92 (m, 1H), 5.14–5.08 (m, 2H), 3.99 (s, 3H), 3.46 (d, 2H, J=7 Hz). Anal. Calc'd for C$_{12}$H$_{12}$O$_4$: C, 65.45; H, 5.49; Found: C, 65.54; H, 5.49.

36c) Methyl 5-formyl-2-(2-E-butyloxy-2-oxo-ethoxy)-3-(1-prop-2-enyl)benzoate

Phenol 36b was alkylated with C-butyl bromoacetate the usual way Io give a yellow oil (quant.). $^1$H-NMR(300 MHz, CDCl$_3$): 9.94 (s, 1H), 8.21 (d, 1H, J=2 Hz), 7.90 (d, 1H, J=9 Hz), 6.05–5.92 (m, 1H), 5.15–5.05 (m, 2H), 4.51 (s, 2H), 3.93 (s, 3H), 3.61 (br d, 2H, J=7 Hz), 1.49 (s, 9H). Anal. Calc'd for C$_{18}$H$_{22}$O$_6$: C, 64.66; H, 6.63; Found: C, 64.54; H, 6.62.

36d) (E)-Methyl 5-[3-((3-(2-t-butyloxycarbonylaminoethoxy)phenyl))-3-oxo-1-propenyl]-2-[2-(t-butyloxy)-2-oxo-ethoxy]-3-(1-prop-2-enyl)benzoate Methyl ketone 1c (0.28 g, 1.0 mmol), aldehyde 36c (0.34 g, 1.0 mmol), potassium fluoride (freshly dried, 58 mg, 1.0 mmol), and tetramethylorthosilicate (74 mL, 0.50 mmol) were heated under nitrogen in dry DMF (2 mL) at room temperature for 2 days and then at 70° C. for 2 days. After cooling, the mixture was extracted with EtOAc and water (5×), then brine. After drying (MgSO$_4$), solvent was removed and the product was chromatographed on silica gel, eluting with 0% to 35% EtOAc in hexanes. Removal of solvent gave a yellow foam (0.20 g). MS(NH$_3$): 613 (base, M+NH$_4$).

36e) (E)-Methyl 5-[3-((3-(2-aminoethoxy)phenyl))-3-oxo-1-propenyl]-2-(carboxymethoxy)-3-(1-prop-2-enyl) benzoate.trifluoroacetate Substrate 36d was deprotected in the usual way to give a yellow powder (85%). $^1$H-NMR(300 MHz, d$_6$DMSO): 8.09 (d, 1H, J=2Hz), 7.99–7.87 (m, 6H), 7.73 (d, 1H, J=16 Hz), 7.63 (br s, 1H), 7.55 (t, 1H, J=8 Hz), 7.31 (dd, 1H, J=8, 3Hz), 6.11–5.97 (m, 1H), 5.11–5.06 (m, 2H), 4.52 (s, 2H), 4.28–4.25 (m, 2H), 3.86 (s, 3H), 3.54 (d, 2H, J=7 Hz), 3.30–3.25 (m, 2H). Anal. Calc'd for C$_{26}$H$_{26}$F$_3$NO$_9$.H$_2$O: C, 54.64; H, 4.94; N, 2.45; F, 9.97; Found: C, 54.87; H, 4.66; N, 2.48; F, 10.05.

Example 76
(E)-4-[3-((3-(Aminomethyl)phenyl))-3-oxo-1-propenyl] benzene-1,2-bis(oxyacetic acid.trifluoroacetate.

76a) 3,4-Bis-(2-1-butyloxy-2-oxo-ethoxy)benzaldehyde 3,4-Dihydroxybenzaldehyde (10 g, 7.2 mmol), butyl bromoacetate (32 mL, 20 mmol, added in portions over 3 days), and potassium carbonate (22 g, 16 mmol) were heated in DMF (75 mL) to 60°–65° C. for 4 days. After the usual work-up, the product was chromatographed on silica gel, eluting with 0% to 25% EtOAc in hexanes.

Solvent was removed in vacuo to give a pale yellow solid (13.6 g). mp. 90.5–93.7° C. HR-MS: Calc'd 384.2022, Found 384.2014.

76b) Methyl 3-[(N,N-bis-t-butyloxycarbonyl) aminomethyl]benzoic acid

Methyl 3-(bromomethyl)benzoate (10 g, 44 mmol) and di-t-butyliminodicarboxylate, potassium sale (11.4 g, 44 mmol) were stirred at room temperature in DMF for 3.5 h. The mixture was diluted with EtOAc and extracted with water (3×), then brine. After drying (MgSO$_4$), solvent was removed in vacuo to give a clear oil (15.5 g). $^1$H-NMR(300 MHz, CDCl$_3$): 7.99 (s, 1H), 7.94 (d, 1H, J=8 Hz), 7.50 (d, 1H, J=8Hz), 1.39 (t, 1H, J=8 Hz), 4.82 (s, 2H), 3.91 (s, 3H), 1.47 (s, 18H). MS(NH$_3$): 383 (base, M+NH$_4$).

76c) (E)-4-[3-((3-(Aminomethyl)phenyl))-3-oxo-1-propenyl]benzene-1,2-bis(oxyacetic acid).trifluoroacetate Methyl ester 76b was converted to the β-ketophosphonate, coupled with aldehyde 76a, and deprotected via the usual methods to give a yellow solid. IR(KBr) cm$^{-1}$ 3400–2700, 1732, 1662. FAB-HR-MS(glycerol): Calc'd 386.1240, Found 386.1250.

Example 91
(E)-4-[3-((3-(2-Aminoethyl)phenyl))-3-oxo-1-propenyl]-2-ethoxyphenoxyacetic acid trifluoroacetate.

91a) Methyl 3-(cyanomethyl)benzoate

Methyl 3-(bromomethyl)benzoate (8.5 g, 37 mmol) and sodium cyanide (1.8 g, 37 mmol) were stirred at room temperature in DMF (40 mL) overnight. The mixture was diluted with EtOAc and extracted several times with water containing a small amount of brine, then brine, dried (MgSO$_4$), and solvent removed in vacuo. The crude product (6.8 g, yellow oil) was sufficiently pure to be used in the next step without purification. IR(neat): cm$^{-1}$ 2249, 1722. $^1$H-NMR(300 MHz, CDCl$_3$): 8.03–8.01 (m, 2H), 7.57–7.46 (m, 2H), 3.94 (s, 3H), 3.82 (s, 2H).

91b) Methyl 3-(2-aminoethyl)benzoate.p-toluenesulfonate

Nitrile 91a (4.8 g, 27 mmol) was hydrogenated on a Parr shaker at 40 psi $H_2$ in the presence of 10% Pd/C (0.48 g) and p-toluenesulfonic acid (5.2 g, 27 mmol) in methanol (100 mL). The solution was filtered through a Celite pad to remove the catalyst, then solvent was removed in vacuo to give an orange solid (10.7 g). HR-MS: Calc'd. 180.1025. Found 180.1025.

91c) Methyl 3-(2-t-butyloxycarbonylaminoethyl)benzoate

Amine salt 91b (12.5 g, 34 mmol), triethylamine (4.7 mL, 34 mmol), and di-t-butyl-dicarbonate (7.4 g, 34 mmol) were stirred in methanol (150 mL) for 5 h at room temperature. After solvent removal, the residue was diluted with EtOAc and extracted with water (2×), then brine. Drying ($MgSO_4$) and solvent removal gave an oil (9.3 g). $^1$H-NMR(300 MHz, $CDCl_3$): 7.92–7.88 (m, 2H), 7.40–7.38 (m, 2H), 3.92 (s, 3H), 3.41–3.36 (m, 2H), 2.86 (t, 2H, J=7 Hz), 1.43 (s, 9H).

91d) 4-Formyl-2-ethoxyphenoxyacetic acid

4-Hydroxy-3-ethoxybenzaldehyde (5.0 g, 36 mmol), potassium carbonate (5.0 g, 36 mmol), and t-butyl bromoacetate (5.9 mL, 36 mmol) were heated to 55° C. overnight in DMF (35 mL). After removal of solvent, the mixture was extracted with EtOAc and water, then brine. After drying ($Na_2SO_4$), solvent was removed no yield a white solid (9.7 g). mp 90°–92.6° C. MS($NH_3$): 298 (base, M+$NH_4$).

91e) (E)-4-[3-((3-(2-Aminoethyl)phenyl))-3-oxo-1-propenyl]-2-ethoxyphenoxyacetic acid.trifluoroacetate The N-BOC methyl ester 91c was converted to a β-ketophosphonate in the usual manner, then coupled to aldehyde 91d and deprotected as previously described give a yellow solid. HR-MS: Calc'd 370.1654, Found 370.1646.

Example 112
(E)-4-[3-((3-(guanidinylmethyl)phenyl))-3-oxo-1-propenyl]-2-methoxyphenoxyacetic acid.trifluoroacetate 112a) Methyl 3-((N,N-bis-(t-butyloxycarbonyl)aminomethyl))benzoate Methyl 3-bromomethylbenzoate (10 g, 44 mmol) and $(BOC)_2NK$ (11.4 g, 44 mmol) were stirred in DMF (40 mL) for 3 h at room temperature. The mixture was diluted with EtOAc and extracted with water (3×), then brine. Drying ($Na_2SO_4$), filtration, and evaporation yielded a clear oil (15.5 g) which was sufficiently pure for use in the next step. IR(film) $cm^{-1}$ 1791, 1726. $^1$H NMR(300 MHz, $CDCl_3$): 7.99–7.39 (m, 4H), 4.82 (s, 2H), 3.91 (s, 3H), 1.47 (s, 18H). MS($NH_3$): 383 (base, M+$NH_4$), 327 (32%), 283 (8%).

112b) Dimethyl 2-((3-(N-t-butyloxycarbonyl)aminomethyl))phenyl-2-oxo-ethylphosphonate Diisopropylamine (8.0 mL, 57 mmol) was added dropwise over 6 min to a −65° C. solution of n-butyllithium (35 mL, 56 mmol, 1.6M in hexanes) in dry THF (200 mL). After 0.5 h, a solution of dimethyl methylphosphonate (3.0 mL, 28 mmol) in dry THF (30 mL) was added over 8 min. After 2.75 h at −65° C., a solution of ester 112a (10 g, 27 mmol) in dry THF (70 mL) was added over 45 min. The mixture was stirred for an additional 45 min at −65° C. then for 3 h at 0°–5° C. The reaction was quenched with 1M HCl (50 mL) and extracted with EtOAc and water, then brine. After drying ($Na_2SO_4$), filtering, and evaporation, the produce was purified by two silica gel chromatographies, initially eluting with EtOAc/hexane, then methanol/chloroform gradients. Evaporation of solvent yielded a yellow oil (0.78 g). 1H NMR(300 MHz, $CDCl_3$): 7.90–7.43 (m, 4H), 4.9 g (br, 1H), 4.38 (d, 2H, J=6 Hz), 3.79 (d, 6H, J=11 Hz), 3.64 (d, 2H, J=23 Hz), 1.47 (s, 9H).

The chromatographies also yielded many fractions which were a mixture of mono- and bis-N-BOC products. These were most readily dealt with by complete N-BOC removal by treatment with TFA/$CH_2Cl_2$, followed by reprotection (di-t-butyl dicarbonate, $Et_3N$, EtOAc) to give mono-BOC exclusively. Chromatography purification yielded an additional 2.3 g of the desired product.

112C) 3-Methoxy-4-(2-methoxy-2-oxo-ethoxy)benzaldehyde

Vanillin was alkylated with methyl bromoacetate in DMF in the presence of $K_2CO_3$ in the usual way to give a colorless solid (77%). mp 91°–93° C. IR(KBr) $cm^{-1}$ 1760, 1682. $^1$H NMR(300 MHz, $CDCl_3$): 9.86 (s, 1H), 7.44–7.40 (m, 2H), 6.86 (d, 1H, J=8 Hz), 4.79 (s, 2H), 3.95 (s, 3H), 3.80 (s, 3H). Anal. Calc'd for $C_{11}H_{12}O_5$: C, 58.92; H, 5.41; Found: C, 59.02; H, 5.26.

112d) (E)-Methyl 4-(3-((3-N-(t-butyloxycarbonyl)aminomethyl))phenyl-3-oxo-1-propenyl]-2-methoxyphenoxyacetate Benzaldehyde 112c and β-ketophosphonate 112b were condensed in the usual way to give a yellow glassy solid (76%). IR(KBr) $cm^{-1}$ 3368, 1760, 1708, 1660. $^1$H NMR(300 MHz, $CDCl_3$): 7.90 (m, 2H), 4.74 (d, 1H, J=16 Hz), 7.50–7.46 (m, 2H), 7.36 (d, 1H, J=16 Hz), 7.20–7.17 (m, 2H), 6.81 (d, 1H, J=8 Hz), 4.90 (br, 1H), 4.75 (s, 2H), 4.39 (d, 2H, J=6 Hz), 3.95 (s, 3H), 3.80 (s, 3H), 1.45 (s, 9H). HR-MS: Calc'd. 473.2288, Found 473.2291.

112e) (E)-Methyl 4-[3-((3-(aminomethyl)phenyl))-3-oxo-1-propenyl]-2-methoxyphenoxyacetate.trifluoroacetate BOC-amine 122d was deprotected with TFA/$CH_2Cl_2$ in the usual way to yield a yellow solid (79%). IR(KBr) $cm^{-1}$ 1756, 1704, 1656. $^1$H NMR(300 MHz, DMSO): 8.26–8.21 (m, 4H), 7.83 (d, 1H, J=16 Hz), 7.76–6.96 (m, 6H), 4.89 (s, 2H), 4.20–4.14 (m, 2H), 3.89 (s, 3H), 3.71 (s, 3H). HR-MS: Calc'd. 356.1498, Found 56.1505.

(112f) N,N'-bis-(t-Butyloxycarbonyl)-3,5-dimethyl-1H-pyrazole-1-carboxamidine

This reagent was prepared according to the method recently reported (Bernatowicz, M. S.; Wu, Y.; Matsueda, G. R. Tetrahedron Letters 1993, 34, 3389–92) for the desdimethyl analog, yielding a white solid in 70% over two seeps. mp 94°–96° C. IR(KBr) $cm^{-1}$ 3338, 2338, 1770, 1710, 1674. $^1$H NMR(300 MHz, $CDCl_3$): 9.03 (s, 1H), 5.95 (s, 1H), 2.55 (s, 3H), 2.20 (s, 3H), 1.53 (s, 9H), 1.49 (s, 9H). Anal. Calc'd for $C_{16}H_{26}N_4O_4$: C, 56.77; H, 7.76; N, 16.56; Found: C, 56.81; H, 7.71; N, 16.46. HR-MS: Calc'd. 339.2032, Found 339.2031.

112g) (E)-Methyl 4-[3-((3-N,N'-bis-(t-butyloxycarbonyl)guanidinylmethyl))phenyl-3-oxo-1-propenyl]-2-methoxyphenoxyacetate Benzylic amine sale 112e (0.78 g, 1.7 mmol), N,N'-bis-BOC-pyrazole carboxamidine 122f (0.51 g, 1.5 mmol), and $Et_3N$(0.23 mL, 17 mmol), were stirred in THF (5 mL) at room temperature for 44 h. After evaporation of solvent, the product was isolated by chromatography on silica gel, eluting with 30% to 50% EtOAc in hexane, to yield a yellow solid (0.81 g) following solvent evaporation. IR(KBr) $cm^{-1}$ 3328, 2338, 1760, 1726. $^1$H NMR(300 MHz, $CDCl_3$): 11.54 (br, 1H), 8.60 (br, 1H), 7.91 (m, 2H), 7.74 (d, 1H, J=16 Hz), 7.54–6.81 (m, 6H), 5.95 (s, 1H), 4.75 (s, 2H), 4.72 (d, 2H, J=6 Hz), 3.96 (s, 3H), 3.81 (S, 3H), 1.51 (S, 9H), 1.47 (S, 9H). MS($NH_3$): 598 (base, M+H).

112h) (E)-4-[3-((3-(Quanidinylmethyl)phenyl))-3-oxo-1-propenyl]-2-methoxyphenoxyacetic acid.trifluoroacetate Methyl ester 112 g (0.20 g, 0.33 mmol) was saponified by stirring with 1M aq. NaOH (0.33 mL, 0.33 mmol) in MeOH (10 mL) for 22 h. Acidification with 1M HCl and EtOAc extraction allowed isolation of the carboxylic acid as a yellow glassy solid (quant.). HR-MS: Calc'd. 584.2608, Found 584.2600.

This crude carboxylic acid was deprotected with TFA/ $CH_2Cl_2$ in the usual way to yield a hygroscopic yellow powder (0.11 g). IR(KBr) $cm^{-1}$ 3500–2700, 1738, 1668. HR-MS: Calc'd. 384.1559, Found 384.1567.

Example 120
(E)-4-[3-((3-(1-piperazinyl)phenyl)-3-oxo-1-propenyl]-2-methoxyphenoxyacetic acid.trifluoroacetate 120a Methyl 3-((N,N-bis-(2-hydroxyethyl)amino))benzoate Ethylene oxide (16 mL, 330 mmol) was added rapidly via a cold syringe to a solution of methyl 3aminobenzoate (5.0g, 33 mmol), glacial acetic acid (40 mL), and water (40 mL) with stirring at 0° C. under nitrogen beneath a dry ice/acetone condenser. After 1 h, the cold bath was removed and the reaction stirred for 43 h at room temperature. Water was added, and the mixture neutralized by adding solid sodium bicarbonate portionwise. After a series of $EtOAc/H_2O$ extractions, the crude produce was isolated by concentration under reduced pressure. Purification by chromatography on silica gel, eluting with 0% to 5% MeOH in EtOAc, and evaporation yielded an oil (6.9 g). IR(neat): $cm^{-1}$ 340, 1718. $^1H$ NMR(300 MHz, $CDCl_3$): 7.38–6.87 (m, 4H), 3.90–3.85 (m, 7H), 3.65–3.59 (m, 4H), 3.27 (s, 2H). HR-MS: Calc'd. 240.1236, Found 240.1237.

120b) Methyl 3-((N,N-bis-(2-chloroethyl)amino))benzoate

A solution of 120a (6.9 g, 29 mmol) in chloroform (50 mL) was added over 2 h to $POCl_3$ (9.9 g) with heating under reflux. After 2.7 h additional reflux, the mixture was cooled in an ice bath, and filtered to remove a white precipitate. The filtrate was neutralized by extraction with saturated aqueous $NaHCO_3$ and chloroform. The organic phase was dried ($Na_2SO_4$), filtered, and evaporated no an oil (5.4 g). IR(neat): $cm^{-1}$ 1720. $^1H$ NMR(300 MHz, $CDCl_3$): 7.42–6.87 (m, 4H), 3.90(s, 3H), 3.77 (t, 4H, J=7 Hz), 3.64 4H, J=7 Hz). HR-MS: Calc'd. 276.0558, Found 276.0553.

120c) Methyl 3-(4-benzyl-1-piperazinyl)benzoate

Benzylamine (1.2 mL, 11 mmol), 120b (1.0 g, 3.6 mmol), water (50 mL), and acetone (50 mL) were heated an reflux for 28 h, then stirred at room temperature an additional 41 h. After evaporation of the acetone, the mixture was extracted with EtOAc (2x). The organic phase was extracted further with water and brine, then dried ($Na_2SO_4$), filtered and concentrated. The product was purified by chromatography on silica gel, eluting with 30% to 50% EtOAc in hexanes, then evaporated to yield a yellow oil (0.57 g). IR(neat): $cm^{-1}$ 1722. $^1H$ NMR(300 MHz, $CDCl_3$): 7.57–7.08 (m, 9H), 3.88 (s, 3H), 3.56 (s, 2H), 3.24 (m, 4H), 2.61 (m, 4H). HR-MS: Calc'd. 311.1760, Found 311.1764.

120d) Methyl 3-(1-piperazinyl)benzoate.p-toluene sulfonic acid

A mixture of 120c (2.6 g, 8.5 mmol), p-toluene sulfonic acid (1.6 g, 8.5 mmol), 10% Pd/C (0.52 g) and MeOH (40 mL) were shaken on a Parr hydrogenation apparatus at 49 psi of $H_2$. After TLC indicated complete reaction, the catalyst was removed by filtration through a Celite pad, and solvent was evaporated to yield a white solid (3.3 g). IR(KBr): $cm^{-1}$ 3416, 1724. $^1H$ NMR(300 MHz, $CDCl_3$): 8.70 (br, 1H), 7.51–7.28 (m, 6H), 7.12 (d, 2H, J=8 Hz), 4.10 (br, 1H), 3.85 (s, 3H), 3.41–3.24 (m, 8H), 2.29 (s, 3H). HR-MS: Calc'd. 221.1290, Found 221. 1294.

120e) Methyl 3-((4-(t-butyloxycarbonyl)-1-piperazinyl)benzoate

Piperazine salt 120d (3.3 g, 8.1 mmol), $Et_3N$ (1.2 mL, 8.6 mmol), di-1-butyl dicarbonate (1.8 g, 8.2 mmol), EtOAc (40 mL), and MeOH (a few mL, no aid solubility) were stirred at room temperature for 6 h. The mixture was diluted with EtOAc and extracted with water, 5% aq. $KHSO_4$, saturated $NaHCO_3$, and brine, then dried ($Na_2SO_4$), filtered and concentrated. A yellow oil (2.6 g) was obtained. IR(neat): $cm^{-1}$ 1722, 1690. $^1H$ NMR(300 MHz, $CDCl_3$): 7.57–7.09 (m, 4H), 3.89 (s, 3H), 3.58 (t, 2H, J=5 Hz), 3.17 (t, 4H, J=5 Hz), 1.47 (s, 9H). HR-MS: Calc'd. 321.1814, Found 321.1809.

120f) (E)-4-[3-((3-(1—Piperazinyl)phenyl)-3-oxo-1-propenyl]-2-methoxyphenoxyacetic acid.trifluoroacetate Methyl ester 120e was converted to its β-ketophosphonate, coupled with aldehyde 23a, and deprotected as usual to yield a solid. IR(KBr): $cm^{-1}$ 3150–2480, 1754, 1660. $^1H$ NMR(300 MHz, $CDCl_3$): 13.0 (br, 1H), 8.8 (br, 1H), 7.79 (d, 1H, J=15 Hz), 7.71–7.30 (m, 7 H), 6.92 (d, 1H, J=8 Hz), 4.76 (s, 2H), 3.88 (s, 3H), 3.50–3.35 (m, 4H), 3.28–3.22 (m, 4H). HR-MS: Calc'd. 397.1763, Found 397.1773.

Example 121
(E)-4-[[3-[3-((2-(methylamino)ethoxy))-phenyl]-3-oxo-1-propenyl]]-2-methoxyphenoxyacetic acid.trifluoroacetate 121a) N-t-Butyloxycarbonyl-N-methyl-2-aminoethanol A solution of di-t-butyl dicarbonate (10 g, 46 mmol) in EtOH (40 mL) was added dropwise over 50 min to a solution of 2-(methylamino)ethanol (4.0 mL, 50 mmol) in EtOH (40 mL) with stirring in an ice bath. The mixture was stirred for 2 h at 0° C. then 17.5 h at room temperature. After evaporation of solvent, the mixture was extracted with EtOAc and water, then brine. Drying ($MgSO_4$), filtration, and evaporation yeilded a colorless oil (7.4 g). IR(film) $cm^{-1}$ 3448, 1698. $^1H$ NMR(300 MHz, $CDCl_3$): 3.77–3.71 (m, 2H), 3.40–3.37 (m, 2H), 2.91 (s, 3H), 1.45 (s, 9H). Anal. Cald'd for $C_8H_{17}NO_3$: C, 54.84; H, 9.78; N, 7.99; Found: C, 54.58; H, 9.50; N, 7.89. MS($NH_3$): 193 (76%, M+$NH_4$), 176 (base, M+H).

121b) Methyl 3-((2-(N-t-Butyloxycarbonyl-N-methylamino)ethoxy))benzoate

Methyl 3-hydroxybenzoate (6.4 g, 42 mmol), alcohol 121a (7.4 g, 42 mmol), diisopropyl azodicarboxylate (8.3 mL, 42 mmol), and triphenylphosphine (11.1 g, 42 mmol) were stirred in dry THF (120 mL) at 0° C. for 1 h, then for 18 h at room temperature. After evaporation of solvent, the product was isolated by chromatography on silica gel, eluting with 0% to 30% EtOAc in hexane to yield a clear oil (9.4 g). IR(film) $cm^{-1}$ 1726, 1696. $^1H$ NMR(300 MHz, $CDCl_3$): 7.64–7.09 (m, 4H), 4.13 (m, 2H), 3.92 (s, 3H), 3.62 (br, 2H), 2.99 (s, 3H), 1.46 (s, 9H). Anal. Cald'd for $C_{16}H_{23}NO_5$: C, 62.11; H, 7.51; N, 4.53; Found: C, 61.67; H, 7.43; N, 4.47. HR-MS: Calc'd. 310.1654, Found 310. 1650.

121c) (E)-4-[[3-[3-((2-(Methylamino)ethoxy))phenyl]-3-oxo-1-propenyl]]-2-methoxyphenoxyacetic acid.trifluoroacetate Methyl ester 121b was converted to its β-ketophosphonate, coupled with aldehyde 23a and deprotected in the usual way to yield a yellow solid.

IR(KBr) $cm^{-1}$ 3300–2700, 1730, 1658. $^1H$ NMR(300 MHz, $CDCl_3$): 8.63 (br, 2H), 7.87 (d, 1H, J=8 Hz), 7.81 (d, 1H, J=15 Hz), 7.71 (d, 1H, J=15 Hz), 7.62–6.92 (m, 6H), 4.76 (s, 2H), 4.33 (t, 2H, J=5 Hz), 3.88 (s, 3H, 3.56–3.35 (m, 2H), 2.67 (t, 3H, J=5 Hz). HR-MS: Calc'd. 386.1604, Found 386.1603.

Example 126
4-[3-((3-(2-Aminoethoxy)phenyl))-3-oxo-1-propyl]phenoxyacetic acid.hydrochloride 126a) 4-[3-((3-(2-1-Butyloxycarbonylamino)-ethoxyphenyl))-3-oxo-1-propyl]phenoxyacetic acid Enone 1d (0.10 g, 0.23 mmol) and platinum oxide (10 mg) were shaken on a Parr hydrogenation apparatus at 10 psi $H_2$ in a mixture of ethanol (25 mL) and methanol (10 mL) for 18 h. The catalyst was removed by filtration through a Celite pad, and solvent was removed in vacuo to give a gum (0.16 g, incompletely dried). MS(NH$_3$): 461 (base, M+NH$_4$).

126b) 4-[3-((3-(2-Aminoethoxy)phenyl))-3-oxo-1-propyl]-phenoxyacetic acid.hydrochloride Deprotection as described above for 1e gave an orange-tan solid (88 mg) which contained ~20% of an inseparable impurity. IR(nujol): cm$^{-1}$ 3400–2600, 1738, 1678. HR-MS: Calc'd 344.1498, Found 344.1515.

In addition to the synthesis of the compounds specifically described above, additional representative examples of compounds of this invention are provided below. These compounds were synthesized by the use of synthetic routes and procedures as described above, and variations thereof which would be known to those skilled in the art of synthetic organic chemistry.

Ex. 20. (E)-Ethyl 5-[3-((3-(2-aminoethoxy)-5-ethoxyphenyl))-3-oxo-1-propenyl]-2-(carboxymethoxy) benzoate.trifluoroacetate. HR-MS: Calc'd 458.1815, Found 458.1806.

Ex. 21. (E)-4-[3-((3-(2-Aminoethoxy)-5-ethoxyphenyl))-3-oxo-1-propenyl]phenoxyacetic acid.trifluoroacetate. HR-MS(NH$_3$): Calc'd 386.1604, Found 386.1599.

Ex. 22. (E)-4-[3-((3-(2-Aminoethoxy)phenyl))-3-oxo-1-propenyl]-2-ethoxyphenoxyacetic acid.trifluoroacetate. IR (KBr): cm$^{-1}$ 3600–2400, 1738, 1680. MS(NH$_3$): 386 (base, M+H).

Ex. 25. (E)-(Carboxymethyl) 5-[3-((3-(2aminoethoxy)-phenyl))-3-oxo-1-propenyl]-2-(carboxymethoxy) benzoate.trifluoroacetate. $^1$H-NMR (300 MHz, d$_6$-DMSO): 8.35 (br s, 1H), 8.05–8.02 (br d, 1H, J=8 Hz), 7.85–7.78 (m, 3H), 7.75 (d, 1H, J=15 Hz), 7.65 (br s, 1H), 7.56–7.50 (br t, 1H, J=8 Hz), 7.30–7.27 (br d, 1H, J=9 Hz), 7.13–7.10 (br d, 1H, J=9 Hz), 4.84 (s, 2H), 4.71 (s, 2H), 4.39–4.30 (m, 2H), 3.28–3.24 (m, 2H). IR(KBr): cm$^{-1}$ 3600–2400, 1730, 1702, 1658, 1584.

Ex. 26. (E)-4-[3-((3-(2-Aminoethoxy)phenyl))-3-oxo-1-propenyl]-2-nitrophenoxyacetic acid.trifluoroacetate. MS(NH$_3$): 387 (base, M+H). mp. 167°–168° C.

Ex. 27. (E)-(2-Ethoxy-2-oxoethyl) 5-[3-((3-(2-aminoethoxy)phenyl))-3-oxo-1-propenyl]-2-(carboxymethoxy)-benzoate.trifluoroacetate. HR-MS(NH$_3$): Calc'd 472.1608, Found 472.1605.

Ex. 28. (E)-Benzyl 5-[3-((3-(2-aminoethoxy)phenyl))-3-oxo-1-propenyl]-2-(carboxymethoxy) benzoate.trifluoroacetate. HR-MS(NH$_3$): Calc'd 476.1709, Found 476.1711.

Ex. 29. (E)-4-[3-((3-(2-Aminoethoxy)phenyl))-3-oxo-1-propenyl]benzene-1,2-bis(oxyacetic acid).trifluoroacetate. HR-MS(NH$_3$): Calc'd 416.1345, Found 416.1335.

Ex. 30. (E)-Ethyl 5-[3-((3-(2-aminoethoxy)phenyl))-3-oxo-1-propenyl]-2-(carboxymethoxy) benzoate.trifluoroacetate. HR-MS(NH$_3$): Calc'd 400.1396, Found 400.1407.

Ex. (E)-(Carboxymethyl) 5-[3-((2-(benzyloxy)-5-(2-aminoethoxy))phenyl))-3-oxo-1-propenyl]-2-(carboxymethoxy)benzoate.trifluoroacetate. HR-MS(NH$_3$): Calc'd 550.1713, Found 550.1723.

Ex. 44. (E)-(Carboxymethyl) 5-((3-((2-(1-prop-2-enyloxy)-5-(2-aminoethoxy)phenyl))-3-oxo-1-propenyl))-2-(carboxymethoxy)benzoate.trifluoroacetate. HR-MS (NH$_3$): Calc'd 500.1557, Found 500.1557.

Ex. 65. (E)-4-[3-((3-(2-Aminoethoxy)phenyl))-3-oxo-1-propenyl]-3-methoxyphenoxyacetic acid.hydrochloride. HR-MS(NH$_3$): Calc'd 372.1447, Found 372.1431.

Ex. 101. (E)-Ethyl 5-[3-((3-(2-aminopropyl)phenyl))-3-oxo-1-propenyl]-2(carboxymethoxy) benzoate.trifluoroacetate. HR-MS(NH$_3$): Calc'd 412.1760, Found 412.1765.

Ex. 211. (E)-4-[3-((3-(2-aminoethoxy)phenyl))-1-oxo-prop-2-enyl]-2-methoxyphenoxyacetic acid.trifluoroacetate. MS(NH$_3$): 372 (base, M+H).

Example 300

(+/–)-trans-[[2-methoxy-4-[2-((3-(1piperazinyl)benzoyl)) cyclopropyl]phenoxy]]acetic acid.trifluoroacetic acid.

300a) (+/–)-trans-t-Butyl [[2-methoxy-4-[2-((3(4-1-butyloxycarbonyl-1-piperazinyl)benzoyl))cyclopropyl]-phenoxy]]acetate Sodium hydride (24 mg, 0.60 mmol) was added to a solution of trimethylsulfoxonium iodide (0.13 g, 0.60 mmol) in dry DMSO (1 mL), accompanied by gas evolution. After 30 min, the fully protected enone (immediate precursor for 120f, 300 mg, 0.54 mmol) was added. After 2h at room temperature, the reaction was heated to 60° C. for 100 min. After cooling, the reaction was extracted with EtOAc and water, then brine, then dried (Na$_2$SO$_4$), filtered, and concentrated. The product was purified by silica gel chromatography, eluting with 20% to 30% acetone in hexane to provide a yellow glassy solid (109 mg). IR(KBr): cm$^{-1}$ 1752, 1696, 1666. HR-MS: Calc'd 567.3070, Found 567.3075.

300b) (+/–)-trans-[[2-methoxy-4-[2-((3-(1-piperazinyl)benzoyl))cyclopropyl]phenoxy]]acetic acid.trifluoroacetic acid.

Cyclopropyl adduce 300a was deprotected with TFA/CH$_2$Cl$_2$ in the usual way to provide a pale grey solid. IR(KBr): cm$^{-1}$ 3200–2500(br), 1738, 1680. HR-MS: Calc'd 411.1920, Found 411.1925.

Example 330

[6-((3-(2-Aminoethoxy)benzoyl))-2-naphthalenyloxy] acetic acid.trifluoroacetic acid 330a) 6-Bromo-2-(t-butyldimethylsilyloxy)naphthalene 6-Bromo-2-naphthol (10 g, 44 mmol), imidazole (7.4 g, 110 mmol), and t-butyldimethylsilyl chloride (10 g, 66 mmol) were stirred in DMF (50 mL) at room temperature overnight. TLC analysis indicated incomplete reaction, so additional imidazole (0.6 g) and silyl chloride (1.3 g) were added, and stirring continued 1 day. After evaporation of DMF, the mixture was extracted with EtOAc and 5% aqueous KHSO$_4$, dried (Na$_2$SO$_4$), and evaporated. The crude product was purified by silica gel chromatography, eluting with hexane, to yield a colorless solid (11 g). mp 62°–63° C. $^1$H NMR (300 MHz, CDCl$_3$): 7.90 (d, 1H, J=1 Hz), 7.62 (d, 1H, J=9 Hz), 7.55 (d, 1H, J=9 Hz), 7.46 (dd, 1H, J=9, 2 Hz), 7.14 (d, 1H, J=2 Hz), 7.08 (dd, 1H, J=9,2 Hz), 1.00 (s, 9H), 0.23 (s, 6H). MS(CH$_4$): 365 (20%, M+C$_2$H$_5$, 1 Br isotope pattern), 337 (base, M+H, 1 Br isotope pattern).

330b) 3-(2-t-Butyloxycarbonylaminoethoxy) benzaldehyde

Diisopropylazodicarboxylate (2.0 mL, 10 mmol) was added to a solution of 3-hydroxybenzaldehyde (1.23 g, 10 mmol), 2-(t-butyloxycarbonylamino) ethanol (1.6 g, 10 mmol), and triphenylphosphine 2.7 g, 10 mmol) with stirring in dry THF (50 mL) in an ice bath. After allowing the reaction mixture to warm to room temperature overnight, the solvent was evaporated under vacuum. The mixture was diluted with EtOAc (300 mL) and extracted with 1M NaOH (20 mL), water (2×20 mL), and brine (10 mL). After drying (MgSO$_4$), and evaporation, the product was purified by chromatography on silica gel, eluting with 0% to 50%

EtOAc in hexane. Evaporation of solvent yielded a pale yellow viscous oil (1.6 g), which was only about 80% pure. 1H NMR(300 MHz, CDCl₃): major component 9.97 (s, 1H), 7.48–7.13 (m, 4H), 4.97 (br, 1H), 4.09–4.05 (m, 2H), 3.58–3.53 (m, 2H), 1.45 (s, 9H). IR(neat): cm⁻¹ 3353 (s, br), 1694 (s). MS(NH₃): 283 (base, M+NH₄).

330c) 1-[3-((2-(t-Butyloxycarbonylamino)ethoxy) phenyl]-1-((6-(t-butyldimethylsilyloxy)-2-naphthalenyl)) methanol n-Butyllithium (1.6M in hexane, 15 mL, 24 mmol) was added dropwise to a −78° C. solution of naphthyl bromide 330a (8.0 g, 24 mmol) in dry THF (60 mL). After 0.5h, a solution of aldehyde 330b (3.2 g, 12 mmol) in dry THF (40 mL) was added. The reaction mixture was maintained at −78° for 5h, then allowed to warm to room temperature overnight. After evaporation of solvent, the mixture was extracted with EtOAc and 5% aq. KHSO₄, and dried (Na₂SO₄). After concentration, the product was purified by chromatography on silica gel, eluting with 0% to 50% EtOAc in hexane. Solvent removal yielded a yellow oil (2.0 g). IR(thin film): cm⁻¹ 3420, 1696. MS(NH₃): 541 (base, M+NH₄).

330d) 6-[3-((2-(t-Butyloxycarbonylamino)ethoxy)) benzoyl]-2-(t-butyldimethylsilyloxy)naphthalene Alcohol 330c (2.0 g) and MnO₂ were stirred in CH₂Cl₂ (50 mL) under N₂ at room temperature for 3h. More MnO₂ (2×2.0 g) was added in portions over the next 24 h and stirring continued until TLC analysis indicated complete reaction. After solvent removal, the product was purified by chromatography on silica gel, eluting with 0% to 30% EtOAc in hexane. Evaporation of solvents yielded a clear glassy solid (1.07 g). MS(NH₃): 539 (base, M+NH₄). Anal. Calc'd for C₃₀H₃₉NO₅Si: C, 69.06; H, 7.53; N, 2.68; Si, 5.38; Found: C, 68.76; H, 7.45; N, 2.69; Si, 5.31.

330e) 6-[3-((2-(t-Butyloxycarbonylamino)ethoxy))-benzoyl]-2-hydroxy-naphthalene

Silyl ether 330d (1.0 g, 1.9 mmol) and tetrabutylammonium fluoride (1M in THF, 1.9 mL, 1.9 mmol) were stirred in THF (40 mL) at room temperature under N₂ for 2h. After solvent evaporation, the mixture was extracted with EtOAc and 5% aq. KHSO₄, then water, finally brine. Concentration and chromatography on silica gel, eluting with 0% to 40% EtOAc in hexane yielded, after drying, a colorless foam (0.70 g). IR(KBr): cm⁻¹ 3334, 1686. MS(NH₃): 425 (M+NH₄), 402 (M+H).

330f) t-Butyl [[6-[3-((2-(t-Butyloxycarbonylamino)-ethoxy))-benzoyl]-2-naphthalenyloxy]]acetate 2-Hydroxynaphthalene 330e (0.60 g, 1.5 mmol) was alkylated with t-butylbromoacetate (0.24 mL, 1.5 mmol) in the presence of K₂CO₃ (0.20 g, 1.5 mmol) in DMF (7 mL) in the usual way to yield a colorless solid (0.64 g) after silica gel chromatography. IR(KBr): cm⁻¹ 3340, 1746, 1684. ¹H NMR(300 MHz, CDCl₃): 8.21 (s, 1H), 7.94–7.10 (m, 9H), 5.0 (br, 1H), 4.68 (s, 2H), 4.09 (t, 2H, J=7 Hz), 3.56–3.52 m, 2H), 1.52 (s, 9H), 1.44 (2, 9H). MS(NH₃): 539 (base, M+NH₄), 522 (25%, M+H).

330g) [6-((3-(2-Aminoethoxy)benzoyl))-2naphthalenyloxy]acetic acid.trifluoroacetic acid.

N-BOC-t-butyl ester 330f (0.59 g) and trifluoroacetic acid (1 mL) were stirred in CH₂Cl₂ in the usual way to give the fully deprotected salt (0.48 g) as an off-white solid. 1H NMR(300 MHz, d-6 DMSO): 8.27–7.25 (m, 13H), 4.84 (s, 2H), 4.22 (t, 2H, J=7 Hz), 3.24 (br, 2H). MS(NH₃): 383 (M+NH₄), 366 (M+H).

Ex. 315. (+/−)-trans-[[2-methoxy-4-[2-((3-(2-aminoethoxy)benzoyl))cyclopropyl]phenoxy]]acetic acid.trifluoroacetic acid. MS(NH₃): 404 (5%, M+NH₄), 386 (base, M+H).

In the Tables below, HN(CH₂CH₂)₂N represents the group

Utility

The compounds of this invention possess antiplatelet efficacy, as evidenced by their activity in standard platelet aggregation assays or platelet fibrinogen binding assays, as described below. A compound is considered to be active in these assays if it has an IC₅₀ value of less than about 1 mM. Platelet aggregation and fibrinogen binding assays which may be used to demonstrate the antiplatelet activity of the compounds of the invention are described below.

Platelet Aggregation Assay:

Venous blood was obtained from the arm of a healthy human donor who was drug-free and aspirin-free for at least two weeks prior to blood collection. Blood was collected into 10 mL citrated Vacutainer tubes. The blood was centrifuged for 15 minutes at 150×g at room temperature, and platelet-rich plasma (PRP) was removed. The remaining blood was centrifuged for 15 minutes at 1500×g at room temperature, and platelet-poor plasma (PPP) was removed. Samples were assayed on a aggregometer (PAP-4 Platelet Aggregation Profiler), using PPP as the blank (100% transmittance). 200 ul of PRP was added to each micro test tube, and transmittance was set to 0%. 20 ul of various agonists (ADP, collagen, arachidonate, epinephrine, thrombin) were added to each tube, and the aggregation profiles were plotted (% transmittance versus time). The results are expressed as % inhibition of agonist-induced platelet aggregation. For the IC₅₀ evaluation, the test compounds were added at various concentrations prior to the activation of the platelets.

Purified GPIIb/IIIa-Fibrinogen Binding ELISA

The following reagents are used in the GPIIb/IIIa-fibrinogen binding ELISA:

purified GPIIb/IIIa (148.8 µg/mL);

biotinylated fibrinogen (~1 mg/mL or 3000 nM);

anti-biotin alkaline phosphatase conjugate (Sigma no. A7418);

flat-bottom, high binding, 96-well plates (Costar Cat. no. 3590);

phosphatase substrate (Sigma 104) (40 mg capsules);

bovine serum albumin (BSA) (Sigma no. A3294);

Alkaline Phosphatase buffer −0.1M glycine-HCl, 1 mM MgCl₂·6H₂O, 1 mM ZnCl₂, pH 10.4;

Binding buffer −20 mM Tris-HCl, 150 mM NaCl, 1 mM CaCl₂. 2H₂O, 0.02% NAN₃, pH 7.0;

Buffer A−50 mM Tris-HCl, 100 mM NaCl, 2 mM CaCl₂·2H₂O, 0.02% NAN₃, pH 7.4;

Buffer A+3.5% BSA (Blocking buffer);

Buffer A+0.1% BSA (Dilution buffer); 2N NaOH.

The following method steps are used in the GPIIb/IIIa-fibrinogen binding ELISA:

Coat plates with GPIIb/IIIa in Binding buffer (125 ng/100 ul/well) overnight at 4° C. (Leave first column uncoated for non-specific binding). Cover and freeze plates at −70° C. until used. Thaw plate 1 hour at room temperature or overnight at 4° C. Discard coating solution and wash once with 200 ul Binding buffer per well. Block plate 2 hours at room temperature on shaker with 200 μl Buffer A+3.5% BSA (Blocking buffer) per well. Discard Blocking buffer and wash once with 200 ul Buffer A+0.1% BSA (Dilution buffer) per well. Pipet 11 uL of test compound (10×the concentration to be tested in Dilution buffer) into duplicate wells. Pipet 11 ul Dilution buffer into non-specific and total binding wells. Add 100 uL Biotinylated fibrinogen (1/133 in Dilution buffer, final concentration=20 nM) to each well. Incubate plates for 3 hours at room temperature on a plane shaker. Discard assay solution and wash twice with 300 uL Binding buffer per well. Add 100 uL Anti-biotin alkaline phosphatase conjugate (1/1500 in Dilution buffer) to each well. Incubate plates for 1 hour at room temperature on plate shaker. Discard conjugate and wash twice with 300 51 Binding buffer per well. Add 100 uL Phosphatase substrate mg/ml in Alkaline phosphatase buffer) to each well. Incubate plate at room temperature on shaker until color develops. Stop color development by adding 25 uL 2N NaOH per well. Read plate at 405 nm. Blank against non-specific binding (NSB) well. % Inhibition is calculated as 100-(Test Compound Abs/Total Abs)×100.

Platelet-Fibrinogen Binding Assay:

Binding of $^{125}$I-fibrinogen to platelets was performed as described by Bennett et al. (1983) Proc. Natl. Acad. Sci. USA 80: 417–2422, with some modifications as described below. Human PRP (h-PRP) was applied to a Sepharose column for the purification of platelet fractions. Aliquots of platelets ($5\times10^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The $^{125}$I-fibrinogen bound to the activated platelets was separated from the free form by centrifugation and then counted on a gamma counter. For an $IC_{50}$ evaluation, the test compounds were added at various concentrations prior to the activation of the platelets.

The compounds of Formula I of the present invention may also possess thrombolytic efficacy, that is, they are capable of lysing (breaking up) already formed platelet-rich fibrin blood clots, and thus are useful in treating a thrombus formation, as evidenced by their activity in the tests described below. Preferred compounds of the present invention for use in thrombolysis include those compounds having an $IC_{50}$ value (that is, the molar concentration of the compound capable of achieving 50% clot lysis) of less than about 1 mM, more preferably an $IC_{50}$ value of less than about 0.1 mM.

Thrombolytic Assay:

Venous blood was obtained from the arm of a healthy human donor who was drug-free and aspirin free for at least two weeks prior to blood collection, and placed into 10 ml citrated Vacutainer tubes. The blood was centrifuged for 15 minutes at 1500×g at room temperature, and platelet rich plasma (PRP) was removed. To the PRP was then added $1\times10^{-3}$M of the agonist ADP, epinephrine, collagen, arachidonate, serotonin or thrombin, or a mixture thereof, and the PRP incubated for 30 minutes. The PRP was centrifuged for 12 minutes at 2500×g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fla.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the Lest compound. For the $IC_{50}$ evaluation, the test compounds were added at various concentrations, and the percentage of lysis caused by the test compounds was calculated.

The compounds of Formula I of the present invention are also useful for administration in combination with anticoagulant agents such as warfarin or heparin, or antiplatelet agents such as aspirin, piroxicam or ticlopidine, or thrombin inhibitors such as boropeptides, hirudin or argatroban, or thrombolytic agents such as tissue plasminogen activator, anistreplase, urokinase or streptokinase, or combinations thereof.

Table A below sets forth the biological activity of representative compounds of the present invention.

TABLE A

| Example No. | Platelet Aggregation Assay $IC_{50}$ |
|---|---|
| 1 | ++ |
| 2 | ++ |
| 3 | +++ |
| 20 | ++ |
| 21 | ++ |
| 22 | +++ |
| 23 | +++ |
| 24 | ++ |
| 25 | +++ |
| 26 | +++ |
| 27 | + |
| 28 | + |
| 29 | ++ |
| 30 | ++ |
| 43 | +++ |
| 44 | +++ |
| 65 | ++ |
| 75a | + |
| 75b | >100 |
| 75c | + |
| 76 | + |
| 91 | + |
| 93 | >100 (21% inhibition at 100 μM) |
| 101 | ++ |
| 112 | ++ |
| 120 | +++ |
| 121 | ++ |
| 125a | >100 |
| 126 | + |
| 211 | >100 |
| 240 | >100 |
| 241 | >100 |
| 242 | >100 |
| 243 | >100 |
| 244 | >100 |
| 245 | >100 (19% inhibition at 100 μM) |
| 246 | >100 |
| 247 | >100 |
| 248 | >100 (13% inhibition at 100 μM) |
| 249 | >100 (20% inhibition at 100 μM) |
| 250 | >100 |
| 251 | >100 (18% inhibition at 100 μM) |
| 252 | >100 (38% inhibition at 100 μM) |

In Table A the biological activity of the compounds is indicated as the $IC_{50}$ value in the platelet aggregation assay described above. The $IC_{50}$ values are expressed as: +++= $IC_{50}$ of <10 uM; ++=$IC_{50}$ value of 10 uM to 50 uM; +=$IC_{50}$ of 51–100 uM. As used herein "uM" means micromolar.

Dosage and Formulation

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an anti-aggregation agent.

The compounds of this invention can be administered by any means that produces contact of the active agent with the agent's site of action, glycoprotein IIb/IIIa (GPIIb/IIIa), in the body of a mammal. They can be administered by any conventional means available for use in conjunction with pharmaceuticals, either as individual therapeutic agents or in a combination of therapeutic agents, such as a second antiplatelet agent such as aspirin or ticlopidine which are agonist-specific. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 no 100 mg/kg of body weight per day, and most preferably between about 1.0 to 20 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension:

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent selected from: an anti-coagulant agent such as warfarin or heparin; an anti-platelet agent such as aspirin, piroxicam or ticlopidine; a thrombin inhibitor such as a boropeptide thrombin inhibitor, or hirudin; or a thrombolytic agent such as plasminogen activators, such as tissue plasminogen activator, anistreplase, urokinase or streptokinase. The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent (anti-coagulant agent, anti-platelet agent, thrombin inhibitor, and/or thrombolytic agent) may be administered essentially at the same time, or in any order; for example the compound of Formula I may be administered first, followed by administration of the second agent (anti-coagulant agent, anti-platelet agent, thrombin inhibitor, and/or thrombolytic agent). When not administered at the same time, preferably the administration of the compound of Formula and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent (anti-coagulant agent, anti-platelet agent, thrombin inhibitor, and/or thrombolytic agent) are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Although the proper dosage of the compound of Formula I when administered in combination with the second therapeutic agent will be readily ascertainable by a medical practitioner skilled in the art, once armed with the present disclosure, by way of general guidance, where the compounds of this invention are combined with anti-coagulant agents, for example, a daily dosage may be about 0.1 to 100 milligrams of the compound of Formula I and about 1 to 7.5 milligrams of the anti-coagulant, per kilogram of patient body weight. For a tablet dosage form, the novel compounds of this invention generally may be present in an amount of about 5 to 10 milligrams per dosage unit, and the anti-coagulant in an amount of about 1 to 5 milligrams per dosage unit.

Where the compounds of Formula I are administered in combination with a second anti-platelet agent, by way of general guidance, typically a daily dosage may be about 0.01 to 25 milligrams of the compound of Formula I and about 50 to 150 milligrams of the additional anti-platelet agent, preferably about 0.1 to 1 milligrams of the compound of Formula I and about 1 to 3 milligrams of antiplatelet agents, per kilogram of patient body weight.

Further, by way of general guidance, where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, in is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the inhibition of platelet aggregation, the treatment of blood clots, and/or the treatment of thromboembolic disorders, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood than the specified materials and conditions are important in practicing the invention but that unspecified materials and conditions are not excluded so long as they do not prevent the benefits of the invention from being realized.

The Tables below set forth representative compounds of the invention.

TABLE 1

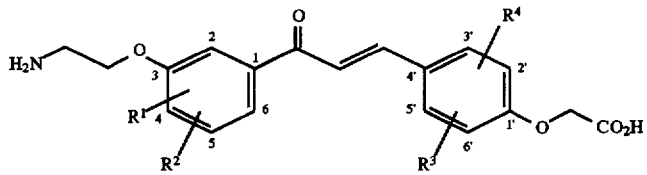

| Ex. No. | $R^1$ | $R^2$ | $R^3$ | $R^4$ |
|---|---|---|---|---|
| 1 | H | H | H | 6'-$CO_2Et$ |
| 2 | H | H | H | 6'-$CO_2Et$ |
| 3 | H | 6-$OCH_2CH=CH_2$ | H | 6'-$CO_2Et$ |
| 4 | H | 6-$OCH_2Ph$ | H | 6'-$CO_2Et$ |
| 5 | H | 6-$OCH_2CH_2$(i-Pr) | H | 6'-$CO_2Et$ |
| 6 | H | 6-$CH_2CH_2CH_3$ | H | 6'-$CO_2Et$ |
| 7 | H | 6-$CO_2Me$ | H | 6'-$CO_2Et$ |
| 8 | H | 6-Br | H | 6'-$CO_2Et$ |
| 9 | H | 6-$OCH_2CH=CH_2$ | 3'OMe | 6'-$CO_2Et$ |
| 10 | H | 6-$OCH_2Ph$ | 3'OMe | 6'-$CO_2Et$ |
| 11 | H | 6-$OCH_2CH_2$(i-Pr) | 3'OMe | 6'-$CO_2Et$ |
| 12 | H | 6-$CH_2CH_3$ | 3'OMe | 6'-$CO_2Et$ |
| 13 | H | 6-$OCH_2CH=CH_2$ | 5'OMe | 6'-$CO_2Et$ |
| 14 | H | 6-$OCH_2Ph$ | 5'OMe | 6'-$CO_2Et$ |
| 15 | H | 6-$OCH_2CH_2$(i-Pr) | 5'OMe | 6'-$CO_2Et$ |
| 16 | 5-$CH_2CH_2CH_3$ | H | H | 6'-$CO_2Et$ |
| 17 | 5-Br | H | H | 6'-$CO_2Et$ |
| 18 | 5-Br | 6-$OCH_2CH=CH_2$ | H | 6'-$CO_2Et$ |
| 19 | 5-$OCH_2CH=CH_2$ | H | H | 6'-$CO_2Et$ |
| 20 | 5-OEt | H | H | 6'-$CO_2Et$ |
| 21 | 5-OEt | H | H | H |
| 22 | H | H | H | 6'-OEt |
| 23 | H | H | H | 6'-OMe |
| 24 | H | H | H | 6'-$CO_2$-n-Bu |
| 25 | H | H | H | 6'-$CO_2CH_2CO_2H$ |
| 26 | H | H | H | 6'-$NO_2$ |
| 27 | H | H | H | 6'-$CO_2CH_2CO_2Et$ |
| 28 | H | H | H | 6'-$CO_2CH_2Ph$ |
| 29 | H | H | H | 6'$OCH_2CO_2H$ |
| 30 | H | H | H | 6'-$CO_2Me$ |

TABLE 1-continued

| Ex. No. | $R^1$ | $R^2$ | $R^3$ | $R^4$ |
|---|---|---|---|---|
| 31 | H | H | H | 6'-F |
| 32 | H | H | H | 6'-Cl |
| 33 | H | H | H | 6'-Br |
| 34 | H | H | H | 6'-I |
| 35 | H | H | H | 6'-CH$_2$CH$_3$ |
| 36 | H | H | 2'-OMe | 6'-CO$_2$Me |
| 37 | H | H | 5'OMe | 6'-CO$_2$Me |
| 38 | H | H | 2'CO$_2$Me | 6'-CO$_2$Me |
| 39 | H | H | 3'-OMe | 6'-CO$_2$Me |
| 40 | H | 6-OCH$_2$CH=CH$_2$ | H | 6'-CO$_2$Me |
| 41 | H | 6-OCH$_2$Ph | H | 6'-CO$_2$Me |
| 42 | 5-OEt | H | H | 6'-CO$_2$Me |
| 43 | H | 6-OCH$_2$Ph | H | 6'-CO$_2$CH$_2$CO$_2$H |
| 44 | H | 6-OCH$_2$CH=CH$_2$ | H | 6'-CO$_2$CH$_2$CO$_2$H |
| 45 | H | H | H | 6'-CO$_2$CH$_2$CO$_2$H |
| 46 | H | 6-OCH$_2$CH=CH$_2$ | H | 6'-OMe |
| 47 | H | 6-OCH$_2$Ph | H | 6'-OMe |
| 48 | H | 6-OCH$_2$CH$_2$(i-Pr) | H | 6'-OMe |
| 49 | 5-OEt | H | H | 6'-OMe |
| 50 | 5-Br | 6-OCH$_2$CH=CH$_2$ | H | 6'-OMe |
| 51 | H | 6-OCH$_2$CH=CH$_2$ | H | 6'-NO$_2$ |
| 52 | H | 6-OCH$_2$Ph | H | 6'-NO$_2$ |
| 53 | H | H | H | 6'-NO$_2$ |
| 54 | 5-OEt | H | H | 6'-NO$_2$ |
| 55 | 5-Br | H | H | 6'-NO$_2$ |
| 56 | 5-OCH$_2$CH=CH$_2$ | H | H | 6'-NO$_2$ |
| 57 | 5-CH$_2$CH$_2$CH$_3$ | H | H | 6'-NO$_2$ |
| 58 | 5-Br | 6-OCH$_2$CH=CH$_2$ | H | 6'-NO$_2$ |
| 59 | H | H | 5'CO$_2$Me | H |
| 60 | H | H | 5'-NO$_2$ | H |
| 61 | H | H | 5'-SO$_2$CH$_3$ | H |
| 62 | H | H | 5'-OCOCH$_3$ | H |
| 63 | H | H | 5'-CH$_3$ | H |
| 64 | H | H | 5'-OEt | H |
| 65 | H | H | 5'-OMe | H |
| 66 | 5-OCH$_2$CH$_2$CH$_2$Ph | H | H | 6'-CO$_2$Me |
| 67 | 5-OCH$_2$CH$_2$CH$_2$Ph | H | H | 6'-NO$_2$ |
| 68 | 5-OCH$_2$CH$_2$CH$_2$Ph | H | H | 6'-OMe |
| 69 | 5-OCH$_2$CH$_2$CH$_2$(i-Pr) | H | H | 6'-CO$_2$Me |
| 70 | 5-OCH$_2$CH$_2$CH$_2$(i-Pr) | H | H | 6'-NO$_2$ |
| 71 | 5-OCH$_2$CH$_2$CH$_2$(i-Pr) | H | H | 6'-OMe |
| 72 | H | H | 2'-F | 6'-F |
| 73 | H | 6-OCH$_2$CH=CH$_2$ | 2'-F | 6'-F |
| 74 | H | 6-OCH$_2$Ph | 2'-F | 6'-F |
| 75 | 5-OCH$_2$CH$_2$CH$_2$Ph | H | 2'-F | 6'-F |
| 75a | H | H | H | H |
| 75b | H | H | 2'-CH$_2$CH=CH$_2$ | 6'-CO$_2$Me |
| 75c | H | H | H | 6'-Ph |

TABLE 2

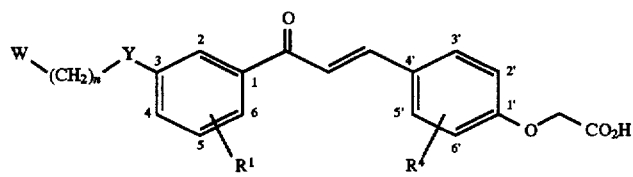

| Ex. No. | W | n | Y | R$^1$ | R$^4$ |
|---|---|---|---|---|---|
| 76 | H$_2$N | 1 | bond | H | 6'-OCH$_2$CO$_2$H |
| 77 | H$_2$N | 1 | bond | H | 6'-CO$_2$Me |
| 78 | H$_2$N | 1 | bond | H | 6'-OMe |
| 79 | H$_2$N | 1 | bond | H | 6'-NO$_2$ |
| 80 | H$_2$N | 1 | bond | H | 6'-OEt |
| 81 | H$_2$N | 1 | bond | H | 5'-OMe |
| 82 | H$_2$N | 1 | bond | 6-OCH$_2$CH=CH$_2$ | 6'-OMe |
| 83 | H$_2$N | 1 | bond | 6-OCH$_2$Ph | 6'-OMe |
| 84 | H$_2$N | 1 | bond | 6-OCH$_2$CH$_2$(i-Pr) | 6'-OMe |
| 85 | CH$_3$NH | 1 | bond | H | 6'-OMe |
| 86 | CH$_3$NH | 1 | bond | H | 6'-OEt |
| 87 | CH$_3$NH | 1 | bond | H | 6'CO$_2$Me |
| 88 | CH$_3$NH | 1 | bond | H | 6'-NO$_2$ |
| 89 | CH$_3$NH | 1 | bond | 6-OCH$_2$CH=CH$_2$ | 6'-OMe |
| 90 | CH$_3$NH | 1 | bond | 6-OCH$_2$Ph | 6'-OMe |
| 91 | H$_2$N | 2 | bond | H | 6'-OEt |
| 92 | H$_2$N | 2 | bond | H | 6'-OMe |
| 93 | H$_2$N | 2 | bond | H | 6'-NO$_2$ |
| 94 | H$_2$N | 2 | bond | H | 6'CO$_2$Me |
| 95 | H$_2$N | 2 | bond | 6-OCH$_2$CH=CH$_2$ | 6'-OMe |
| 96 | CH$_3$NH | 2 | bond | H | 6'-OMe |
| 97 | CH$_3$NH | 2 | bond | H | 6'-NO$_2$ |
| 98 | CH$_3$NH | 2 | bond | H | 6'-CO$_2$Me |
| 99 | CH$_3$NH | 2 | bond | 6-OCH$_2$CH=CH$_2$ | 6'-OMe |
| 100 | CH$_3$NH | 2 | bond | 6-OCH$_2$CH=CH$_2$ | 6'-NO$_2$ |
| 101 | H$_2$N | 3 | bond | H | 6'-CO$_2$Et |
| 102 | H$_2$N | 3 | bond | H | 6'-OMe |
| 103 | H$_2$N | 3 | bond | H | 6'NO$_2$ |
| 104 | H$_2$N | 3 | bond | 6-OCH$_2$CH=CH$_2$ | 6'-OMe |
| 105 | H$_2$N | 3 | bond | 6-OCH$_2$Ph | 6'-OMe |
| 106 | H$_2$N | 3 | bond | 6-OCH$_2$CH=CH$_2$ | 6'-NO$_2$ |
| 107 | CH$_3$NH | 3 | bond | H | 6'-CO$_2$Et |
| 108 | CH$_3$NH | 3 | bond | H | 6'-NO$_2$ |
| 109 | CH$_3$NH | 3 | bond | H | 6'-OMe |
| 110 | CH$_3$NH | 3 | bond | 6-OCH$_2$CH=CH$_2$ | 6'-OMe |
| 111 | CH$_3$NH | 3 | bond | 6-OCH$_2$Ph | 6'-OMe |
| 112 | H$_2$NC(=NH)NH | 1 | bond | H | 6'-OMe |
| 113 | H$_2$NC(=NH)NH | 1 | bond | H | 6'-NO$_2$ |
| 114 | H$_2$NC(=NH)NH | 1 | bond | H | 6'-CO$_2$Me |
| 115 | H$_2$NC(=NH)NH | 1 | bond | 6-OCH$_2$CH=CH$_2$ | 6'-OMe |
| 116 | H$_2$NC(=NH)NH | 1 | bond | 6-OCH$_2$Ph | 6'-OMe |
| 117 | HN(CH$_2$CH$_2$)$_2$N | 0 | bond | H | 6'-CO$_2$Et |
| 118 | HN(CH$_2$CH$_2$)$_2$N | 0 | bond | H | 6'-CO$_2$Me |
| 119 | HN(CH$_2$CH$_2$)$_2$N | 0 | bond | H | 6'NO$_2$ |
| 120 | HN(CH$_2$CH$_2$)$_2$N | 0 | bond | H | 6'-OMe |
| 121 | CH$_3$NH | 2 | O | H | 6'-OMe |
| 122 | HN(CH$_2$CH$_2$)N | 0 | O | 6-OCH$_2$CH=CH$_2$ | 6'-OMe |
| 123 | HN(CH$_2$CH$_2$)N | 0 | O | 6-OCH$_2$Ph | 6'-OMe |
| 124 | HN(CH$_2$CH$_2$)N | 0 | O | 5-OCH$_2$CH$_2$CHMe$_2$ | 6'-OMe |
| 125 | HN(CH$_2$CH$_2$)N | 0 | O | 5-OCH$_2$CH$_2$CH$_2$Ph | 6'-OMe |
| 125a | NH$_2$ | 1 | bond | H | H |

TABLE 3

| Ex. No. | W | n | Y | R¹ | R⁴ |
|---|---|---|---|---|---|
| 126 | H$_2$N | 2 | O | H | H |
| 127 | H$_2$N | 2 | O | H | 6'-NO$_2$ |
| 128 | H$_2$N | 2 | O | H | 6'-OMe |
| 129 | H$_2$N | 2 | O | H | 6'-CO$_2$Me |
| 130 | CH$_3$NH | 2 | O | H | 6'-OMe |
| 131 | CH$_3$NH | 2 | O | H | 6'-NO$_2$ |
| 132 | CH$_3$NH | 2 | O | H | 6'-CO$_2$Me |
| 133 | H$_2$N | 2 | O | 6-OCH$_2$CH=CH$_2$ | 6'-OMe |
| 134 | CH$_3$NH | 2 | O | 6-OCH$_2$CH=CH$_2$ | 6'-OMe |
| 135 | H$_2$NC(=NH)NH | 1 | bond | H | 6'-OMe |
| 136 | H$_2$NC(=NH)NH | 1 | bond | 6-OCH$_2$CH=CH$_2$ | 6'-OMe |
| 137 | HN(CH$_2$CH$_2$)$_2$N | 0 | bond | H | 6'-OMe |
| 138 | HN(CH$_2$CH$_2$)$_2$N | 0 | bond | 6-OCH$_2$CH=CH$_2$ | 6'-OMe |
| 139 | HN(CH$_2$CH$_2$)$_2$N | 0 | bond | H | 6'-OMe |
| 140 | HN(CH$_2$CH$_2$)$_2$N | 0 | bond | 6-OCH$_2$CH=CH$_2$ | 6'-OMe |
| 141 | H$_2$NC(=NH)NH | 0 | bond | H | 6'-OMe |
| 142 | H$_2$NC(=NH)NH | 0 | bond | H | 6'-CO$_2$Me |
| 143 | H$_2$NC(=NH)NH | 0 | bond | H | 6'-NO$_2$ |
| 144 | H$_2$NC(=NH)NH | 0 | bond | 6-OCH$_2$CH=CH$_2$ | 6'-NO$_2$ |
| 145 | H$_2$NC(=NH)NH | 0 | bond | 6-OCH$_2$Ph | 6'-OMe |

TABLE 4

| Ex. No. | W | n | Y | P | R⁴ |
|---|---|---|---|---|---|
| 146 | H$_2$N | 2 | O | 0 | 6'-OMe |
| 147 | H$_2$N | 2 | O | 1 | 6'-OMe |
| 148 | H$_2$N | 2 | O | 2 | 6'-OMe |
| 149 | H$_2$N | 2 | O | 0 | 6'-NO$_2$ |
| 150 | H$_2$N | 2 | O | 1 | 6'-NO$_2$ |
| 151 | H$_2$N | 2 | O | 2 | 6'-NO$_2$ |
| 152 | H$_2$N | 2 | O | 0 | 6'-CO$_2$Me |
| 153 | H$_2$N | 2 | O | 1 | 6'-CO$_2$Me |
| 154 | H$_2$N | 2 | O | 2 | 6'-CO$_2$Ne |
| 155 | CH$_3$NH | 2 | O | 2 | 6'-OMe |
| 156 | CH$_3$NH | 2 | O | 1 | 6'-OMe |
| 157 | CH$_3$NH | 2 | O | 0 | 6'-OMe |
| 158 | CH$_3$NH | 2 | O | 2 | 6'-NO$_2$ |
| 159 | CH$_3$NH | 2 | O | 1 | 6'-NO$_2$ |
| 160 | CH$_3$NH | 2 | O | 0 | 6'-NO$_2$ |
| 161 | CH$_3$NH | 2 | O | 2 | 6'-CO$_2$Me |
| 162 | CH$_3$NH | 2 | O | 1 | 6'-CO$_2$Me |
| 163 | CH$_3$NH | 2 | O | 0 | 6'-CO$_2$Me |
| 164 | H$_2$NC(=NH)NH | 1 | bond | 2 | 6'-OMe |
| 165 | H$_2$NC(=NH)NH | 1 | bond | 1 | 6'-OMe |
| 166 | H$_2$NC(=NH)NH | 1 | bond | 0 | 6'-OMe |
| 167 | HN(CH$_2$CH$_2$)$_2$N | 0 | bond | 2 | 6'-OMe |
| 168 | HN(CH$_2$CH$_2$)$_2$N | 0 | bond | 1 | 6'-OMe |
| 169 | HN(CH$_2$CH$_2$)$_2$N | 0 | bond | 0 | 6'-OMe |
| 170 | H$_2$N(CH$_2$CH$_2$)CH | 0 | bond | 2 | 6'-OMe |
| 171 | H$_2$N(CH$_2$CH$_2$)CH | 0 | bond | 1 | 6'-OMe |
| 172 | H$_2$N(CH$_2$CH$_2$)CH | 0 | bond | 0 | 6'-OMe |
| 173 | HN(CH$_2$CH$_2$)$_2$N | 0 | bond | 2 | 6'-NO$_2$ |

TABLE 4-continued

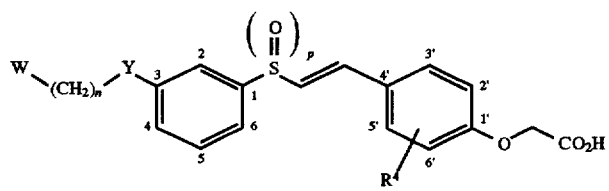

| Ex. No. | W | n | Y | P | R⁴ |
|---|---|---|---|---|---|
| 174 | HN(CH₂CH₂)₂N | 0 | bond | 1 | 6'-NO₂ |
| 175 | HN(CH₂CH₂)₂N | 0 | bond | 0 | 6'-NO₂ |

TABLE 5

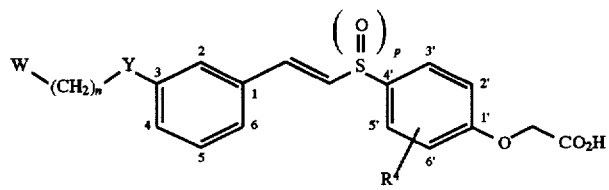

| Ex. No. | W | n | Y | p | R⁴ |
|---|---|---|---|---|---|
| 176 | H₂N | 2 | O | 0 | 6'-OMe |
| 177 | H₂N | 2 | O | 1 | 6'-OMe |
| 178 | H₂N | 2 | O | 2 | 6'-OMe |
| 179 | H₂N | 2 | O | 0 | 6'-NO₂ |
| 180 | H₂N | 2 | O | 1 | 6'-NO₂ |
| 181 | H₂N | 2 | O | 2 | 6'-NO₂ |
| 182 | H₂N | 2 | O | 0 | 6'-CO₂Me |
| 183 | H₂N | 2 | O | 1 | 6'-CO₂Me |
| 184 | H₂N | 2 | O | 2 | 6'-CO₂Me |
| 185 | CH₃NH | 2 | O | 2 | 6'-OMe |
| 186 | CH₃NH | 2 | O | 1 | 6'-CMe |
| 187 | CH₃NH | 2 | O | 0 | 6'-OMe |
| 188 | CH₃NH | 2 | O | 2 | 6'-NO₂ |
| 189 | CH₃NH | 2 | O | 1 | 6'-NO₂ |
| 190 | CH₃NH | 2 | O | 0 | 6'-NO₂ |
| 191 | CH₃NH | 2 | O | 2 | 6'-CO₂Me |
| 192 | CH₃NH | 2 | O | 1 | 6'-CO₂Me |
| 193 | CH₃NH | 2 | O | 0 | 6'-CO₂Me |
| 194 | H₂NC(=NH)NH | 1 | bond | 2 | 6'-OMe |
| 195 | H₂NC(=NH)NH | 1 | bond | 1 | 6'-OMe |
| 196 | H₂NC(=NH)NH | 1 | bond | 0 | 6'-OMe |
| 197 | HN(CH₂CH₂)₂N | 0 | bond | 2 | 6'-OMe |
| 198 | HN(CH₂CH₂)₂N | 0 | bond | 1 | 6'-OMe |
| 199 | HN(CH₂CH₂)₂N | 0 | bond | 0 | 6'-OMe |
| 200 | H₂N(CH₂CH₂)CH | 0 | bond | 2 | 6'-OMe |
| 201 | H₂N(CH₂CH₂)CH | 0 | bond | 1 | 6'-OMe |
| 202 | H₂N(CH₂CH₂)CH | 0 | bond | 0 | 6'-OMe |
| 203 | H₂NC(=NH)NH | 1 | bond | 2 | 6'-NO₂ |
| 204 | H₂NC(=NH)NH | 1 | bond | 1 | 6'-NO₂ |
| 205 | H₂NC(=NH)NH | 1 | bond | 0 | 6'-NO₂ |
| 206 | HN(CH₂CH₂)₂N | 0 | bond | 2 | 6'-NO₂ |
| 207 | HN(CH₂CH₂)₂N | 0 | bond | 1 | 6'-NO₂ |
| 208 | HN(CH₂CH₂)₂N | 0 | bond | 0 | 6'-NO₂ |

TABLE 6

| Ex. No. | W | n | Y | $R^1$ | $R^4$ |
|---|---|---|---|---|---|
| 211 | $H_2N$ | 2 | O | H | 6'-OMe |
| 212 | $H_2N$ | 2 | O | 6-$OCH_2CH=CH_2$ | 6'-OMe |
| 213 | $H_2N$ | 2 | O | 6-$OCH_2Ph$ | 6'-OMe |
| 214 | $H_2N$ | 2 | O | H | 6'-$NO_2$ |
| 215 | $H_2N$ | 2 | O | 6-$OCH_2CH=CH_6$ | 6'-$NO_2$ |
| 216 | $H_2N$ | 2 | O | 6-$OCH_2Ph$ | 6'-$NO_2$ |
| 217 | $H_2N$ | 2 | O | H | 6'-$CO_2Me$ |
| 218 | $H_2N$ | 2 | O | 6-$OCH_2CH=CH_2$ | 6'-$CO_2Me$ |
| 219 | $H_2N$ | 2 | O | 6-$OCH_2Ph$ | 6'-$CO_2Me$ |
| 220 | $CH_3NH$ | 2 | O | H | 6'-OMe |
| 221 | $CH_3NH$ | 2 | O | 6-$OCH_2CH=CH_2$ | 6'-OMe |
| 222 | $CH_3NH$ | 2 | O | 6-$OCH_2Ph$ | 6'-OMe |
| 223 | $H_2NC(=NH)NH$ | 1 | bond | H | 6'-OMe |
| 224 | $H_2NC(=NH)NH$ | 1 | bond | 6-$OCH_2CH=CH_2$ | 6'-OMe |
| 225 | $H_2NC(=NH)NH$ | 1 | bond | 6-$OCH_2Ph$ | 6'-OMe |
| 226 | $HN(CH_2CH_2)_2N$ | 0 | bond | H | 6'-OMe |
| 227 | $HN(CH_2CH_2)_2N$ | 0 | bond | 6-$OCH_2CH=CH_2$ | 6'-OMe |
| 228 | $HN(CH_2CH_2)_2N$ | 0 | bond | 6-$OCH_2Ph$ | 6'-OMe |
| 229 | $HN(CH_2CH_2)_2N$ | 0 | bond | H | 6'-OMe |
| 230 | $HN(CH_2CH_2)_2N$ | 0 | bond | 6-$OCH_2CH=CH_2$ | 6'-OMe |
| 231 | $HN(CH_2CH_2)_2N$ | 0 | bond | 6-$OCH_2Ph$ | 6'-OMe |
| 232 | $HN(CH_2CH_2)_2N$ | 0 | bond | H | 6'-$NO_2$ |
| 233 | $HN(CH_2CH_2)_2N$ | 0 | bond | 6-$OCH_2CH=CH_2$ | 6'-$NO_2$ |
| 234 | $HN(CH_2CH_2)_2N$ | 0 | bond | 6-$OCH_2Ph$ | 6'-$NO_2$ |
| 235 | $HN(CH_2CH_2)_2N$ | 0 | bohd | 5-$OCH_2CH_2CH_2Ph$ | 6'-OMe |

TABLE 7

| Ex. No. | W | n | Y | $R^4$ | X | m | $R^1$ |
|---|---|---|---|---|---|---|---|
| 240 | $NH_2$ | 2 | 3-bond | 1'-$NO_2$ | 2'-O | 1 | H |
| 241 | $NH_2$ | 4 | 4-bond | H | 1'-O | 1 | H |
| 242 | $NH_2$ | 2 | 3-O | H | 1'-O | 2 | H |
| 243 | $NH_2$ | 4 | 4-bond | H | 1'-bond | 2 | H |
| 244 | $NH_2$ | 1 | 3-bond | H | 2'-O | 1 | H |
| 245 | $NH_2$ | 1 | 4-bond | H | 1'-bond | 2 | H |
| 246 | $NH_2$ | 1 | 3-bond | H | 1'-O | 1 | H |
| 247 | $NH_2$ | 1 | 3-C≡C— | 6'-$CO_2Et$ | 1'-O | 1 | H |
| 248 | $NMe_2$ | 2 | 3-O | H | 2'-bond | 0 | H |
| 249 | $NH_2$ | 2 | 3-O | 6'-OEt | 1'-O | 1 | n-hexyl |
| 250 | $NH_2$ | 1 | 4-bond | 6'$NO_2$ | 1'-O | 1 | H |
| 251 | $NH_2$ | 3 | 2-O | 6'-$CO_2Et$ | 1'-O | 1 | H |
| 252 | $NH_2$ | 2 | 3-O | 1'-OMe | 2'-bond | 1 | H |

TABLE 8

| Ex. No. | W | n | Y | R¹ | R³ |
|---|---|---|---|---|---|
| 300 | HN(CH$_2$CH$_2$)$_2$N | 0 | bond | H | 6'-OMe |
| 301 | HN(CH$_2$CH$_2$)$_2$N | 0 | bond | 6-OCH$_2$Ph | 6'-OMe |
| 302 | HN(CH$_2$CH$_2$)$_2$N | 0 | bond | 6-OCH$_2$CH=CH$_2$ | 6'-OMe |
| 303 | HN(CH$_2$CH$_2$)$_2$N | 0 | bond | 5-OCH$_2$CH$_2$Ph | 6'-OMe |
| 304 | HN(CH$_2$CH$_2$)$_2$N | 0 | bond | 5-OCH$_2$CH$_2$CH$_2$(i-Pr) | 6'-OMe |
| 305 | HN(CH$_2$CH$_2$)$_2$N | 0 | bond | H | 6'-ON$_2$ |
| 306 | HN(CH$_2$CH$_2$)$_2$N | 0 | bond | 6-OCH$_2$Ph | 6'-ON$_2$ |
| 307 | HN(CH$_2$CH$_2$)$_2$N | 0 | bond | 6-OCH$_2$CH=CH$_2$ | 6'-ON$_2$ |
| 308 | HN(CH$_2$CH$_2$)$_2$N | 0 | bond | 5-OCH$_2$CH$_2$Ph | 6'-ON$_2$ |
| 309 | HN(CH$_2$CH$_2$)$_2$N | 0 | bond | 5-OCH$_2$CH$_2$CH$_2$(i-Pr) | 6'ON$_2$ |
| 310 | HN(CH$_2$CH$_2$)$_2$N | 0 | bond | H | 6'-CO$_2$Me |
| 311 | HN(CH$_2$CH$_2$)$_2$N | 0 | bond | 6-OCH$_2$Pb | 6'-CO$_2$Me |
| 312 | HN(CH$_2$CH$_2$)$_2$N | 0 | bond | 6-OCH$_2$CH=CH$_2$ | 6'-CO$_2$Me |
| 313 | HN(CH$_2$CH$_2$)$_2$N | 0 | bond | 5-OCH$_2$CH$_2$Ph | 6'-CO$_2$Me |
| 314 | HN(CH$_2$CH$_2$)$_2$N | 0 | bond | 5-OCH$_2$CH$_2$CH$_2$(i-Pr) | 6'-CO$_2$Me |
| 315 | H$_2$N | 2 | O | H | 6'-OMe |
| 316 | H$_2$N | 2 | O | H | 6'-NO$_2$ |
| 317 | H$_2$N | 2 | O | H | 6'-CO$_2$Me |
| 318 | H$_2$N | 2 | O | 6-OCH$_2$Ph | 6'-OMe |
| 319 | H$_2$N | 2 | O | 5-OCH$_2$CH$_2$CH$_2$Ph | 6'-OMe |
| 320 | H$_2$N | 2 | O | 6-OCH$_2$Ph | 6'-NO$_2$ |
| 321 | H$_2$N | 2 | O | 6-OCH$_2$Ph | 6'-CO$_2$Me |
| 322 | H$_2$N | 2 | bond | H | 6'-NO$_2$ |

TABLE 9

| Ex. No. | W | n | Y | R¹ | R³ |
|---|---|---|---|---|---|
| 330 | H$_2$N | 2 | O | H | H |
| 331 | H$_2$N | 2 | O | H | 1'-OMe |
| 332 | H$_2$N | 2 | O | H | 1'-NO$_2$ |
| 333 | H$_2$N | 2 | O | H | 1'-CO$_2$Me |
| 334 | H$_2$N | 2 | O | H | 1'-COPh |
| 335 | H$_2$N | 2 | O | H | 1'-SO$_2$Ph |
| 336 | HN(CH$_2$CH$_2$)$_2$N | 0 | bond | H | H |
| 337 | HN(CH$_2$CH$_2$)$_2$N | 0 | bond | H | 1'-OMe |
| 338 | HN(CH$_2$CH$_2$)$_2$N | 0 | bond | H | 1'-NO$_2$ |
| 339 | HN(CH$_2$CH$_2$)$_2$N | 0 | bond | H | 1'-CO$_2$Me |
| 340 | HN(CH$_2$CH$_2$)$_2$N | 0 | bond | H | 1'-COPh |
| 341 | HN(CH$_2$CH$_2$)$_2$N | 0 | bond | H | 1'-SO$_2$Ph |
| 342 | HN(CH$_2$CH$_2$)$_2$N | 0 | bond | 6-OCH$_2$Ph | 1'-OMe |
| 343 | HN(CH$_2$CH$_2$)$_2$N | 0 | bond | 6-OCH$_2$CH=CH$_2$ | 1'-OMe |
| 344 | HN(CH$_2$CH$_2$)$_2$N | 0 | bond | 5-OCH$_2$CH$_2$Ph | 1'-OMe |
| 345 | HN(CH$_2$CH$_2$)$_2$N | 0 | bond | 5-OCH$_2$CH$_2$CH$_2$(i-Pr) | 1'-OMe |
| 346 | HN(CH$_2$CH$_2$)$_2$N | 0 | bond | 6-OCH$_2$Ph | 1'-SO$_2$Ph |
| 347 | HN(CH$_2$CH$_2$)$_2$N | 0 | bond | 6-OCH$_2$CH=CH$_2$ | 1'-SO$_2$Ph |
| 348 | HN(CH$_2$CH$_2$)$_2$N | 0 | bond | 5-OCH$_2$CH$_2$Ph | 1'-SO$_2$Ph |
| 349 | HN(CH$_2$CH$_2$)$_2$N | 0 | bond | 5-OCH$_2$CH$_2$CH$_2$(i-Pr) | 1'-SO$_2$Ph |

What is claimed is:
1. A compound of Formula I:

$$W\text{-}(C(R^7)_2)_n\text{-}Y\text{-}[\text{aryl}(R^1,R^2)]\text{-}L^1\text{-}Z\text{-}L^2\text{-}[\text{aryl}(R^3,R^4)]\text{-}X\text{-}(C(R^7)_2)_m\text{-}A \quad (I)$$

or a pharmaceutically acceptable salt form thereof wherein:

W is —$NR^6R^{6a}$;

Y is selected from —$C(R^7)_2$—, —$C(=O)$—, —$S(O)_p$—, —O—, —$N(R^6)$—, —$NR^6C(=O)$—, —$C(=O)N(R^6)$— or a single bond;
with the proviso that when n=0, then the bond between W and Y is not a heteroatom to heteroatom bond;
with the proviso that when n=0 and W is $NH_2$, then Y is not —$C(=O)$— or —$C(=O)N(R^6)$—;
with the proviso that when n=1 and W is —$NR^6R^{6a}$, then Y is not —$S(O)_p$—, —O—, —$N(R^6)$—, or —$NR^6C(=O)$—;

$L^1$ is a bond;

$L^2$ is selected from:
—($C_1$ to $C_4$ alkyl)—, substituted with 0–8 $R^{5b}$,
—($C_2$ to $C_4$ alkenyl)—, substituted with 0–6 $R^{5b}$,
—($C_2$ to $C_4$ alkynyl)—, substituted with 0–4 $R^{5b}$,
—(cyclopropyl)—, substituted with 0–1 $R^{5b}$,
alternatively, $L^2$ is taken together with $R^3$ to form a benzo-fused ring, said benzo-fused ring being substituted with 0–1 $R^5$;

Z is selected from —$C(=O)$— or —$S(O)_p$—;

X is selected from —$C(=O)$—, —$S(O)_p$—, O, —$N(R^6)$—, —$NR^6C(=O)$—, —$C(=O)N(R^6)$—, or a single bond;

A is selected from $CO_2R^9$, $SO_3H$, tetrazolyl, or $PO_3H$;

$R^1$, $R^2$, $R^3$, $R^4$, and $R^7$ are independently selected from:
H,
$C_1$ to $C_8$ alkyl substituted with 0–5 $R^5$,
$C_2$ to $C_8$ alkenyl substituted with 0–5 $R^5$,
$C_3$ to $C_8$ alkynyl substituted with 0–5 $R^5$,
$C_3$ to $C_8$ cycloalkyl substituted with 0–5 $R^5$,
$C_4$ to $C_8$ cycloalkylalkyl substituted with 0–5 $R^5$,
$C_7$ to $C_{11}$ arylalkyl substituted with 0–5 $R^5$,
C to $C_4$ alkoxy substituted with 0–5 $R^5$,
aryl substituted with 0–5 $R^5$;
a 5–10-membered heterocyclic ring system containing 1–4 heteroatoms independently selected from N, S, and O, said heterocyclic ring being substituted with 0–4 $R^5$;
F, Cl, Br, I, $CF_3$, $CO_2R^{5a}$, $C(=O)R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2co_2R^{5a}$, $CO_2CH_2CO_2R^{5a}$, $N(R^{5a})_2$, $NO_2$, $NR^{5a}C(=O)R^{5a}$, $NR^{5a}C(=O)OR^{5a}$, $NR^{5a}C(=O)N(R^{5a})_2$, $NR^{5a}SO_2N(R^{5a})_2$, $NR^{5a}SO_2R^{5a}$, $S(O)_pR^{5a}$, or $SO_2N(R^{5a})_2$;
alternatively, when m or n are 2–6, $R^7$ can be taken together with $R^7$ bonded to an adjacent carbon atom to form a direct bond, thereby to form a double or triple bond between the adjacent carbon atoms;

$R^5$ is selected independently from H, F, Cl, Br, I, $CF_3$, CN, CHO, $CO_2R^{5a}$, $C(=O)R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O)R^{5a}$, $NR^{5a}C(=O)OR^{5a}$, $NR^{5a}C(=O)N(R^{5a})_2$, $NR^{5a}SO_2N(R^{5a})_2$, $NR^{5a}SO_2R^{5a}$, $S(O)_pR^{5a}$, or $SO_2N(R^{5a})_2$, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$arylalkyl, $R^{5b}$ is selected independently from H, F, Cl, Br, I, $CF_3$, CN, CHO, $CO_2R^{5a}$, $C(=O)R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})2$, $NO_2$, $NR^{5a}C(O=O)R^{5a}$, $NR^{5a}C(=O)OR^{5a}$, $NR^{5a}C(=O)N(R^{5a})_2$, $C_1$ to $C_8$ alkyl, $C_2$ to $C_{C6}$ alkenyl, $C_3$ to $C_{11}$ cycloalkyl, $C_4$ $C_{11}$ cycloalkylmethyl, $C_6$ to $C_{10}$ aryl, or $C_7$ to $C_{11}$ arylalkyl; $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O) R^{5a}$, $NR^{5a}C(=O) OR^{5a}$, $NR^{5a}C(=O)N(R^{5a})_2$, $NR^{5a}SO_2N(R^{5a})_2$, $NR^{5a}SO_2R^{5a}$, $S(O)_pR^{5a}$, or $SO_2N(R^{5a})_2$, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_6$ to $C_{11}$ aryl, or $C_7$ to $C_{11}$ arylalkyl;
alternatively, two $R^{5b}$ groups when attached to adjacent carbon atoms may be taken together to form —$CH_2$—, thereby to form a cyclopropylene group;

$R^{5a}$ is selected from: H, $C_1$ to $C_8$ alkyl, $C_2$ to $C_6$ alkenyl. $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl; p1 $R^6$, $R^{6a}$, and $R^8$ are independently selected from: H, $C_1$ to $C_4$ alkyl, $C_3$ to $C_{11}$ cycloalkyl, $C_6$ to $C_{10}$ aryl, $C_7$ to $C_{11}$ arylalkyl, $C_2$ to $C_7$ alkylcarbonyl, $C_7$ to $C_{11}$ arylcarbonyl, $C_2$ to $C_{11}$ alkoxycarbonyl, $C_4$ to $C_{11}$ cycloalkoxycarbonyl, $C_7$ to $C_{11}$ bicycloalkoxycarbonyl, or $C_7$ to $C_{11}$ aryloxycarbonyl;

$R^9$ is selected from H, $C_1$ to $C_8$ alkyl, $C_3$ to $C_{11}$ cycloalkyl, $C_6$ to $C_{10}$ aryl, $C_7$ to $C_{11}$ aralkyl, $C_3$ to $C_{10}$ alkylcarbonyloxyalkyl, $C_3$ to $C_{10}$ alkoxycarbonyloxyalkyl, $C_2$ to $C_{10}$ alkoxycarbonyl, $C_5$ to $C_{10}$ cycloalkylcarbonyloxyalkyl, $C_5$ to $C_{10}$ cycloalkoxycarbonyloxyalkyl, $C_5$ to $C_{10}$ cycloalkoxycarbonyl, $C_7$ to $C_{11}$ aryloxycarbonyl, $C_8$ to $C_{12}$ aryloxycarbonyloxyalkyl, $C_8$ to $C_{12}$ arylcarbonyloxyalkyl, $C_5$ to $C_{10}$ alkoxyalkylcarbonyloxyalkyl, $C_5$ to $C_{10}$ (5-alkyl-1,3-dioxa-cyclopenten-2-one-yl)methyl, or $C_{10}$ to $C_{14}$ (5-aryl-1,3-dioxa-cyclopenten-2-one-yl)methyl;

m is an integer from 1–6, with the proviso that m plus n cannot be greater than 6;

n is an integer from an integer from 0 to 6;

p is an integer from 0 to 2.

2. A compound of claim 1 wherein $L^2$ is taken together with $R^3$ to form a benzo-fused ring, said benzo-fused ring being substituted with 0–1 $R^5$.

3. A compound of claim 1 wherein $L^2$ is -(cyclopropyl)-, substituted with 0–1 $R^{5b}$.

4. A compound of claim 1 of Formula Ia:

$$W\text{-}(CH_2)_n\text{-}Y\text{-}[\text{aryl}(R^1,R^2)]\text{-}L^1\text{-}Z\text{-}L^2\text{-}[\text{aryl}(R^3,R^4)]\text{-}O\text{-}(CHR^7)_m\text{-}A \quad (Ia)$$

or a pharmaceutically acceptable salt form thereof wherein:

W is —$NR^6R^{6a}$;

Y is selected from —$CH_2$—, —$C(=O)$—, —$S(O)_p$—, —O—, —$N(R^6)$—, —$NR^6C(=O)$—, —$C(=O)N(R^6)$— or a single bond;

with the proviso that when n=0, then the bond between W and Y is not a heteroatom to heteroatom bond;

with the proviso that when n=0 and W is $NH_2$, then Y is not —C(=O)— or —C(=O)N($R^6$)—;

with the proviso that when n=1 and W is —$NR^6R^{6a}$, then Y is not —S(O)$_p$—, —O—, —N($R^6$)—, or —$NR^6$C(=O)—;

$L^1$ is a bond;

$L^2$ is selected from:
-($C_1$ to $C_4$ alkyl)-substituted with 0–4 $R^{5b}$,
-($C_2$ to $C_4$ alkenyl)-substituted with 0–4 $R^{5b}$,
-($C_2$ to $C_4$ alkynyl)-substituted with 0–3 $R^{5b}$,
-(cyclopropyl)-, substituted with 0–1 $R^{5b}$,
alternatively, $L^2$ is taken together with $R^3$ to form a benzo-fused ring, said benzo-fused ring being substituted with 0–1 $R^5$;

Z is selected from —C(=O)— or —S(O)$_p$—;

X is selected from —C(=O)—, —S(O)$_p$—, O, —N($R^6$)—, —$NR^6$C(=O)—, —C(=O)N($R^6$)—, or a single bond;

A is selected from $CO_2R^9$, $SO_3H$, tetrazolyl, or $PO_3H$;

$R^1$, $R^2$, $R^3$, $R^4$, and $R^7$ are independently selected from: H,
$C_1$ to $C_8$ alkyl substituted with 0–4 $R^5$,
$C_2$ to $C_8$ alkenyl substituted with 0–4 $R^5$
$C_3$ to $C_8$ alkynyl substituted with 0–4 $R^5$,
$C_3$ to $C_8$ cycloalkyl substituted with 0–4 $R^5$,
$C_4$ to $C_8$ cycloalkylalkyl substituted with 0–4 $R^5$,
$C_6$ to $C_{11}$ aryl substituted with 0–2 $R^5$,
$C_7$ to $C_{11}$ arylalkyl substituted with 0–2 $R^5$,
$C_1$ to $C_4$ haloalkoxy, F, Cl, Br, I, $CF_3$, CN, CHO, $CO_2R^{5a}$, C(=O)$R^{5a}$, CONH$R^{5a}$, CON($R^{5a}$)$_2$, OC(=O)$R^{5a}$, OC(=O)O$R^{5a}$, O$R^{5a}$, OC(=O)N($R^{5a}$)$_2$, OCH$_2$CO$_2R^{5a}$, CO$_2$CH$_2$CO$_2R^{5a}$, N($R^{5a}$)$_2$, $NO_2$, $NR^{5a}$C(=O)$R^{5a}$, $NR^{5a}$C(=O)O$R^{5a}$, $NR^{5a}$C(=O)N($R^{5a}$)$_2$, $NR^{5a}$SO$_2$N($R^{5a}$)$_2$, $NR^{5a}$SO$_2R^{5a}$, S(O)$_pR^{5a}$, or SO$_2$N($R^{5a}$)$_2$;

$R^5$ is selected independently from H, F, Cl, Br, I, $CF_3$, CN, CHO, $CO_2R^{5a}$, C(=O)$R^{5a}$, CONH$R^{5a}$, CON($R^{5a}$)$_2$, OC(=O)$R^{5a}$, OC(=O)O$R^{5a}$, O$R^{5a}$, OC(=O)N($R^{5a}$)$_2$, OCH$_2$CO$_2R^{5a}$, CO$_2$CH$_2$CO$_2R^{5a}$, N($R^{5a}$)$_2$, $NO_2$, $NR^{5a}$C(=O)$R^{5a}$, $NR^{5a}$C(=O)O$R^{5a}$, $NR^{5a}$C(=O)N($R^{5a}$)$_2$, $NR^{5a}$SO$_2$N($R^{5a}$)$_2$, $NR^{5a}$SO$_2R^{5a}$, S(O)$_pR^{5a}$, or SO$_2$N($R^{5a}$)$_2$, $C_1$ to $C_8$ alkyl, $C_2$ to $C_6$ alkenyl, $C_3$ to $C_8$ cycloalkyl, $C_4$ to $C_8$ cycloalkylmethyl, $C_6$ to $C_{10}$ aryl, or $C_7$ to $C_{11}$ arylalkyl;

$R^{5b}$ is selected independently from H, F, Cl, Br, I, $CF_3$, CN, CHO, $CO_2R^{5a}$, C(=O)$R^{5a}$, CONH$R^{5a}$, CON($R^{5a}$)$_2$, OC(=O)$R^{5a}$, OC(=O)O$R^{5a}$, O$R^{5a}$, OC(=O)N($R^{5a}$)$_2$, OCH$_2$CO$_2R^{5a}$, CO$_2$CH$_2$CO$_2R^{5a}$, N($R^{5a}$)$_2$, $NO_2$, $NR^{5a}$C(=O)$R^{5a}$, $NR^{5a}$C(=O)O$R^{5a}$, $NR^{5a}$C(=O)N($R^{5a}$)$_2$, $NR^{5a}$SO$_2$N($R^{5a}$)$_2$, $NR^{5a}$SO$_2R^{5a}$, S(O)$_pR^{5a}$, or SO$_2$N($R^{5a}$)$_2$, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl;

alternatively, two $R^{5b}$ groups when attached to adjacent carbon atoms may be taken together to form —$CH_2$—, thereby to form a cyclopropylene group;

$R^{5a}$ is selected from: H, $C_1$ to $C_8$ alkyl, $C_2$ to $C_6$ alkenyl, $C_3$ to $C_8$ cycloalkyl, $C_4$ to $C_8$ cycloalkylmethyl, $C_6$ to $C_{10}$ aryl, or $C_7$ to $C_{11}$ arylalkyl;

$R^6$, $R^{6a}$, and $R^8$ are independently selected from: H, $C_1$ to $C_4$ alkyl, $C_3$ to $C_{10}$ cycloalkyl, $C_6$ to $C_{10}$ bicycloalkyl, $C_6$ to $C_{10}$ aryl, $C_7$ to $C_{11}$ arylalkyl, $C_2$ to $C_7$ alkylcarbonyl, $C_7$ to $C_{11}$ arylcarbonyl, $C_2$ to $C_{10}$ alkoxycarbonyl, $C_4$ to $C_{11}$ cycloalkoxycarbonyl, $C_7$ to $C_{11}$ bicycloalkoxycarbonyl, or $C_7$ to $C_{11}$ aryloxycarbonyl;

$R^9$ is selected from H, $C_1$ to $C_8$ alkyl, $C_3$ to $C_{10}$ cycloalkyl, $C_6$ to $C_{10}$ aryl, $C_7$ to $C_{11}$ aralkyl, $C_3$ to $C_{10}$ alkylcarbonyloxyalkyl, $C_3$ to $C_{10}$ alkoxycarbonyloxyalkyl, $C_2$ to $C_{10}$ alkoxycarbonyl, $C_5$ to $C_{10}$ cycloalkylcarbonyloxyalkyl, $C_5$ to $C_{10}$ cycloalkoxycarbonyloxyalkyl, $C_5$ to $C_{10}$ cycloalkoxycarbonyl, $C_7$ to $C_{11}$ aryloxycarbonyl, $C_8$ to $C_{12}$ aryloxycarbonyloxyalkyl, $C_8$ to $C_{12}$ arylcarbonyloxyalkyl, $C_5$ to $C_{10}$ alkoxyalkylcarbonyloxyalkyl, $C_5$ to $C_{10}$ (5-alkyl-1,3-dioxa-cyclopenten-2-one-yl)methyl, or $C_{10}$ to $C_{14}$ (5-aryl-1,3-dioxa-cyclopenten-2-one-yl) methyl;

m is an integer from 1–6, with the proviso that m plus n cannot be greater than 6;

n is an integer from an integer from 0 to 6;

p is an integer from 0 to 2.

5. A compound of claim 1 of Formula Ib:

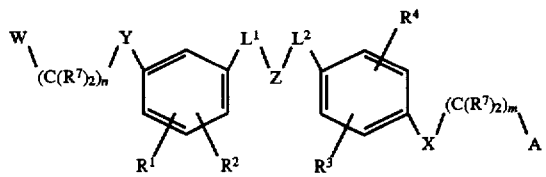

(Ib)

or a pharmaceutically acceptable salt form thereof wherein:

W is —$NR^6R^{6a}$;

Y is selected from —$CH_2$—, —C(=O)—, —S(O)$_p$—, —O—, —N($R^6$)—, —$NR^6$C(=O)—, —C(=O)N($R^6$)— or a single bond;

with the proviso that when n=0, then the bond between W and Y is not a heteroatom to heteroatom bond;

with the proviso that when n=0 and W is $NH_2$, then Y is not —C(=O)— or —C(=O)N($R^6$)—;

with the proviso that when n=1 and W is —$NR^6R^{6a}$, then Y is not —S(O)$_p$—, —O—, —N($R^6$)—, or —$NR^6$C(=O)—;

$L^1$ is a bond;

$L^2$ is selected from:
-($C_1$ to $C_4$ alkyl)-substituted with 0–4 $R^{5b}$,
-($C_2$ to $C_4$ alkenyl)-substituted with 0–4 $R^{5b}$,
-($C_2$ to $C_4$ alkynyl)-substituted with 0–3 $R^{5b}$,
-(cyclopropyl)-, substituted with 0–1 $R^{5b}$,
alternatively, $L^2$ is taken together with $R^3$ to form a benzo-fused ring, said benzo-fused ring being substituted with 0–1 $R^5$;

Z is selected from —C(=O)— or —S(O)$_p$—;

X is selected from —C(=O)—, —S(O)$_p$—, O, —N($R^6$)—, —$NR^6$C(=O)—, —C(=O)N($R^6$)—, or a single bond;

A is selected from $CO_2R^9$, $SO_3H$, tetrazolyl, or $PO_3H$;

$R^1$, $R^2$, $R^3$, $R^4$, and $R^7$ are independently selected from:
H,
$C_1$ to $C_8$ alkyl substituted with 0–4 $R^5$,
$C_2$ to $C_8$ alkenyl substituted with 0–4 $R^5$
$C_3$ to $C_8$ alkynyl substituted with 0–4 $R^5$,
$C_3$ to $C_8$ cycloalkyl substituted with 0–4 $R^5$,
$C_4$ to $C_8$ cycloalkylalkyl substituted with 0–4 $R^5$,
$C_6$ to $C_{10}$ aryl substituted with 0–2 $R^5$,
$C_7$ to $C_{11}$ arylalkyl substituted with 0–2 $R^5$,
$C_1$ to $C_4$ haloalkoxy, F, Cl, Br, I, $CF_3$, CN, CHO, $CO_2R^{5a}$, $C(=O)R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O)R^{5a}$, $NR^{5a}C(=O)OR^{5a}$, $NR^{5a}C(=O)N(R^{5a})_2$, $NR^{5a}SO_2N(R^{5a})_2$, $NR^{5a}SO_2R^{5a}$, $S(O)_pR^{5a}$, or $SO_2N(R^{5a})_2$;

$R^5$ is selected independently from H, F, Cl, Br, I, $CF_3$, CN, CHO, $CO_2R^{5a}$, $C(=O)R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O)R^{5a}$, $NR^{5a}C(=O)OR^{5a}$, $NR^{5a}C(=O)N(R^{5a})_2$, $NR^{5a}SO_2N(R^{5a})_2$, $NR^{5a}SO_2R^{5a}$, $S(O)_pR^{5a}$, or $SO_2N(R^{5a})_2$, $C_1$ to $C_8$ alkyl, $C_2$ to $C_6$ alkenyl, $C_3$ to $C_8$ cycloalkyl, $C_4$ to $C_8$ cycloalkylmethyl, $C_6$ to $C_{10}$ aryl, or $C_7$ to $C_{11}$ arylalkyl;

$R^{5b}$ is selected independently from H, F, Cl, Br, I, $CF_3$, CN, CHO, $CO_2R^{5a}$, $C(=O)R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O)R^{5a}$, $NR^{5a}C(=O)OR^{5a}$, $NR^{5a}C(=O)N(R^{5a})_2$, $NR^{5a}SO_2N(R^{5a})_2$, $NR^{5a}SO_2R^{5a}$, $S(O)_p R^{5a}$, or $SO_2N(R^{5a})_2$, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_6$ to $C_{10}$ aryl, or $C_7$ to $C_{11}$ arylalkyl;
alternatively, two $R^{5b}$ groups when attached to adjacent carbon atoms may be taken together to form —$CH_2$—, thereby to form a cyclopropylene group;

$R^{5a}$ is selected from: H, $C_1$ to $C_8$ alkyl, $C_2$ to $C_6$ alkenyl, $C_3$ to $C_8$ cycloalkyl, $C_4$ to $C_8$ cycloalkylmethyl, $C_6$ to $C_{10}$ aryl, or $C_7$ to $C_{11}$ arylalkyl;

$R^6$, $R^{6a}$, and $R^8$ are independently selected from: H, $C_1$ to $C_4$ alkyl, $C_3$ to $C_{10}$ cycloalkyl, $C_6$ to $C_{10}$ bicycloalkyl, $C_6$ to $C_{10}$ aryl, $C_7$ to $C_{11}$ arylalkyl, $C_2$ to $C_7$ alkylcarbonyl, $C_7$ to $C_{11}$ arylcarbonyl, $C_2$ to $C_{10}$ alkoxycarbonyl, $C_4$ to $C_{11}$ cycloalkoxycarbonyl, $C_7$ to $C_{11}$ bicycloalkoxycarbonyl, or $C_7$ to $C_{11}$ aryloxycarbonyl;

$R^9$ is selected from H, $C_1$ to $C_8$ alkyl, $C_3$ to $C_{10}$ cycloalkyl, $C_6$ to $C_{10}$ aryl, $C_7$ to $C_{11}$ aralkyl, $C_3$ to $C_{10}$ alkylcarbonyloxyalkyl, $C_3$ to $C_{10}$ alkoxycarbonyloxyalkyl, $C_2$ to $C_{10}$ alkoxycarbonyl, $C_5$ to $C_{10}$ cycloalkylcarbonyloxyalkyl, $C_5$ to $C_{10}$ cycloalkoxycarbonyloxyalkyl, $C_5$ to $C_{10}$ cycloalkoxycarbonyl, $C_7$ to $C_{11}$ aryloxycarbonyl, $C_8$ to $C_{12}$ aryloxycarbonyloxyalkyl, $C_8$ to $C_{12}$ arylcarbonyloxyalkyl, $C_5$ to $C_{10}$ alkoxyalkylcarbonyloxyalkyl, $C_5$ to $C_{10}$ (5-alkyl-1,3-dioxa-cyclopenten-2-one-yl)methyl, or $C_{10}$ to $C_{14}$ (5-aryl-1,3-dioxa-cyclopenten-2-one-yl)methyl;

m is an integer from 1–6, with the proviso that m plus n cannot be greater than 6;

n is an integer from an integer from 0 to 6;

p is an integer from 0 to 2.

6. A compound of claims 1, 4, or 5, and pharmaceutically acceptable salt forms thereof, wherein:
W is —$NR^6R^{6a}$;

Y is selected from O, $CH_2$, S or a single bond;
$L^1$ is a bond;
$L^2$ is selected from:
—$CH_2CH_2$— substituted with 0–2 $R^{5b}$, or
—CH=CH— substituted with 0–2 $R^{5b}$;
-(cyclopropyl)-substituted with 0–1 $R^{5b}$;
alternatively, $L^2$ is taken together with $R^3$ to form a benzo-fused ring, said benzo-fused ring being substituted with 0–1 $R^5$;
Z is selected from —C(=O)— or —$S(O)_p$—;
X is selected from —O— or a single bond;
A is selected from $CO_2R^9$, $SO_3H$, tetrazolyl, or $PO_3H$;
$R^1$ and $R^2$ are independently selected from:
H,
$C_1$ to $C_8$ alkyl substituted with 0–2 $R^5$,
$C_2$ to $C_8$ alkenyl substituted with 0–2 $R^5$,
$C_3$ to $C_8$ cycloalkyl substituted with 0–2 $R^5$,
$C_4$ to $C_8$ cycloalkylmethyl substituted with 0–2 $R^5$,
$OR^{5a}$;

$R^3$, $R^4$, and $R^7$ are independently selected from:
H,
$C_1$ to $C_8$ alkyl substituted with 0–2 $R^5$,
$C_2$ to $C_8$ alkenyl substituted with 0–2 $R^5$,
$C_3$ to $C_8$ cycloalkyl substituted with 0–2 $R^5$,
$C_4$ to $C_8$ cycloalkylmethyl substituted with 0–2 $R^5$,
$C_7$ to $C_{11}$ arylalkyl substituted with 0–2 $R^5$,
aryl substituted with 0–2 $R^5$,
F, Cl, Br, I, $CO_2R^{5a}$, $OR^{5a}$, $OCH_2CO_2R^{5a}$, $CO_2CH_2CO_2R^{5a}$, or $NO_2$;

$R^5$ is selected independently from H, F, Cl, Br, I, $CF_3$, CN, CHO, $CO_2R^{5a}$, $C(=O)R^{5a}$, $CONHR^{5a}$, $CON(R^{5a})_2$, $OC(=O)R^{5a}$, $OC(=O)OR^{5a}$, $OR^{5a}$, $OC(=O)N(R^{5a})_2$, $OCH_2CO_2R^{5a}$, $CO_2CH_2CO_2R^{5a}$, $N(R^{5a})_2$, $NO_2$, $NR^{5a}C(=O)R^{5a}$, $NR^{5a}C(=O)OR^{5a}$, $NR^{5a}C(=O)N(R^{5a})_2$, $NR^{5a}SO_2N(R^{5a})_2$, $NR^{5a}SO_2R^{5a}$, $S(O)_pR^{5a}$, $SO_2N(R^{5a})_2$, $C_1$ to $C_8$ alkyl, $C_2$ to $C_6$ alkenyl, $C_3$ to $C_8$ cycloalkyl, $C_4$ to $C_8$ cycloalkylmethyl, $C_6$ to $C_{10}$ aryl, or $C_7$ to $C_{11}$ arylalkyl;

$R^{5b}$ is selected independently from H, $CF_3$, CN, CHO, $CO_2R^{5a}$, $CONHR^{5a}$, $CON(R^{5a})_2$, $OR^{5a}$, $N(R^{5a})_2$, $C_1$ to $C_6$ alkyl, $C_2$ to $C_6$ alkenyl, $C_3$ to $C_{11}$ cycloalkyl, $C_4$ to $C_7$ cycloalkylmethyl, $C_6$ to $C_{10}$ aryl, or $C_7$ to $C_{11}$ arylalkyl;
alternatively, two $R^{5b}$ groups when attached to adjacent carbon atoms may be taken together to form —$CH_2$—, thereby to form a cyclopropylene group;

$R^{5a}$ are selected independently from: H, $C_1$ to $C_6$ alkyl, $C_2$ to $C_6$ alkenyl, $C_4$ to $C_8$ cycloalkylmethyl, $C_6$ to $C_{10}$ aryl, or $C_7$ to $C_{11}$ arylalkyl;

$R^6$, $R^{6a}$, and $R^8$ are independently selected from H, $C_1$ to $C_4$ alkyl, $C_2$ to $C_7$ alkylcarbonyl, $C_7$ to $C_{11}$ arylcarbonyl, $C_2$ to $C_{10}$ alkoxycarbonyl, $C_4$ to $C_{11}$ cycloalkoxycarbonyl, $C_7$ to $C_{11}$ bicycloalkoxycarbonyl, or $C_7$ to $C_{11}$ aryloxycarbonyl;

$R^9$ is selected from H, $C_1$ to $C_4$ alkyl, $C_3$ to $C_{10}$ alkylcarbonyloxyalkyl, $C_3$ to $C_{10}$ alkoxycarbonyloxyalkyl, $C_2$ to $C_{10}$ alkoxycarbonyl, $C_5$ to $C_{10}$ cycloalkylcarbonyloxyalkyl, $C_5$ to $C_{10}$ cycloalkoxycarbonyloxyalkyl, $C_5$ to $C_{10}$ cycloalkoxycarbonyl, $C_7$ to $C_{11}$ aryloxycarbonyl, $C_8$ to $C_{12}$ aryloxycarbonyloxyalkyl, $C_8$ to $C_{12}$ arylcarbonyloxyalkyl, $C_5$ to $C_{10}$ alkoxyalkylcarbonyloxyalkyl, $C_5$ to $C_{10}$ (5-alkyl-1,3-dioxa-cyclopenten-2-one-yl)methyl, or $C_{10}$ to $C_{14}$ (5-aryl-1,3-dioxa-cyclopenten-2-one-yl)methyl;

m is an integer from 1 or 2;

n is an integer from 1 to 3;

p is an integer from 0 to 2.

7. A compound of claim 6, or a pharmaceutically acceptable salt form thereof, wherein:

W is —$NR^6R^{6a}$;

Y is selected from O, S, or a single bond;

$L^1$ is a bond;

$L^2$ is selected from:
—CH=CH— substituted with 0–2 $R^{5b}$; or

-(cyclopropyl)-substituted with 0–1 $R^{5b}$;

alternatively, $L^2$ is taken together with $R^3$ to form a benzo-fused ring, said benzo-fused ring being substituted with 0–1 $R^5$;

Z is selected from —C(=O)— or $S(O)_p$;

X is selected from 0 or a single bond;

A is selected from $CO_2R^9$;

$R^1$ and $R^2$ are independently selected from:
H,
$C_1$ to $C_8$ alkyl substituted with 0–2 $R^5$,
$C_2$ to $C_8$ alkenyl substituted with 0–2 $R^5$,
$C_4$ to $C_8$ cycloalkylmethyl,
$OR^{5a}$;

$R^3$ and $R^4$ are independently selected from:
H,
$C_1$ to $C_6$ alkyl substituted with 0–2 $R^5$,
I, F, Br, Cl, $CO_2R^{5a}$, $OR^{5a}$, $OCH_2CO_2R^{5a}$, $CO_2CH_2CO_2R^{5a}$, or $NO_2$;

$R^5$, $R^7$, $R^{5a}$, and $R^{5b}$ are independently selected from H, $C_1$ to $C_6$ straight or branched alkyl, $C_2$ to $C_6$ alkenyl, $C_4$ to $C_7$ cycloalkylmethyl, or $C_7$ to $C_{11}$ arylalkyl;

$R^6$, $R^{6a}$, and $R^8$ are independently selected from H, $C_1$ to $C_2$ alkyl, $C_2$ to $C_7$ alkylcarbonyl, $C_7$ to $C_{11}$ arylcarbonyl, $C_2$ to $C_{10}$ alkoxycarbonyl, $C_4$ to $C_{11}$ cycloalkoxycarbonyl, $C_7$ to $C_{11}$ bicycloalkoxycarbonyl, or $C_7$ to $C_{11}$ aryloxycarbonyl;

$R^9$ is selected from H, $C_1$ to $C_4$ alkyl, $C_3$ to $C_{10}$ alkylcarbonyloxyalkyl, $C_3$ to $C_{10}$ alkoxycarbonyloxyalkyl, $C_2$ to $C_{10}$ alkoxycarbonyl, $C_5$ to $C_{10}$ cycloalkylcarbonyloxyalkyl, $C_5$ to $C_{10}$ cycloalkoxycarbonyloxyalkyl, $C_5$ to $C_{10}$ cycloalkoxycarbonyl, $C_7$ to $C_{11}$ aryloxycarbonyl, $C_8$ to $C_{12}$ aryloxycarbonyloxyalkyl, $C_8$ to $C_{12}$ arylcarbonyloxyalkyl, $C_5$ to $C_{10}$ alkoxyalkylcarbonyloxyalkyl, $C_5$ to $C_{10}$ (5-alkyl-1,3-dioxa-cyclopenten-2-one-yl)methyl, or $C_{10}$ to $C_{14}$ (5-aryl-1,3-dioxa-cyclopenten-2-one-yl)methyl;

m is selected from 1 or 2;

n is an integer from 1 to 3;

p is selected from 0, 1, or 2.

8. A compound of claim 7, or a pharmaceutically acceptable salt form thereof, wherein $L^1$ is a bond and $L^2$ is —$CH_2$=$CH_2$—.

9. A compound of claim 1, or a pharmaceutically acceptable salt form thereof, selected from:

(a) (E)-ethyl 5-[3-((3-(2-aminoethoxy)phenyl))-3-oxo-1-propenyl]-2-(carboxymethoxy)benzoate;

(b) (E)-(carboxymethyl) 5-[3-((3-(2-aminoethoxy)phenyl))-3-oxo-1-propenyl]-2-(carboxymethoxy)benzoate;

(c) (E)-ethyl 5-[3-((3-(2-aminoethoxy)-5-ethoxyphenyl))-3-oxo-1-propenyl]-2-(carboxymethoxy)benzoate;

(d) (E)-4-[3-((3-(2-aminoethoxy)-5-ethoxyphenyl))-3-oxo-1-propenyl]phenoxyacetic acid;

(e) (E)-ethyl 5-[3-((3-(2-aminopropyl)phenyl))-3-oxo-1-propenyl]-2-(carboxymethoxy)benzoate;

(f) (E)-benzyl 5-[3-((3-(2-aminoethoxy)phenyl))-3-oxo-1-propenyl]-2-(carboxymethoxy)benzoate;

(g) (E)-methyl 5-[3-((3-(2-aminoethoxy)phenyl))-3-oxo-1-propenyl]-2-(carboxymethoxy)benzoate;

(h) (E)-4-[3-((3-(2-aminoethoxy)phenyl))-3-oxo-1-propenyl]-2-nitrophenoxyacetic acid;

(i) (E)-ethyl 5-[3-((2-(1-prop-2-enyloxy)-5-(2-aminoethoxy)phenyl))-3-oxo-1-propenyl]-2-(carboxymethoxy)benzoate;

(j) (E)-n-butyl 5-[3-((3-(2-aminoethoxy)phenyl))-3-oxo-1-propenyl]-2-(carboxymethoxy)benzoate;

(k) (E)-4-[3-((3-(2-aminoethoxy)phenyl))-3-oxo-1-propenyl]-2ethoxyphenoxyacetic acid;

(l) (E)-(carboxymethyl) 5-[3-((2-(benzyloxy)-5-(2-aminoethoxy)phenyl))-3-oxo-1-propenyl]-2-(carboxymethoxy)benzoate;

(m) (E)-(carboxymethyl) 5-((3-((2-(1-prop-2-enyloxy)-5-(2-aminoethoxy)phenyl))-3-oxo-1-propenyl))-2-(carboxymethoxy)benzoate;

(n) (E)-4-[3-((3-(2-aminoethoxy)phenyl))-3-oxo-1-propenyl]-3-methoxyphenoxyacetic acid;

(o) (E)-(2-ethoxy-2-oxoethyl) 5-[3-((3-(2-aminoethoxy)phenyl))-3-oxo-1-propenyl]-2-(carboxymethoxy)benzoate;

(p) (E)-4-[3-((3-(aminomethyl)phenyl))-3-oxo-1-propenyl]benzene-1,2-bis(oxyacetic acid);

(q) (E)-4-[3-((3-(2-aminoethoxy)phenyl))-3-oxo-1-propenyl]benzene-1,2-bis(oxyacetic acid);

(r) (E)-4-[3-((3-(2-aminoethoxy)phenyl))-3-oxo-1-propenyl]-2-methoxyphenoxyacetic acid;

(s) (E)-4-[3-((3-(2-aminoethyl)phenyl))-3-oxo-1-propenyl]-2-ethoxyphenoxyacetic acid;

(t) (E)-4-[3-((3-(2-aminoethoxy)phenyl))-3-oxo-1-propenyl]-phenoxyacetic acid;

(u) (E)-4-[3-((3-(2-(methylamino)ethoxy)phenyl))-3-oxo-1-propenyl]-2-methoxyphenoxyacetic acid;

(v) (E)-ethyl 5-[3-((2-(3-methyl-1-butoxy)-5-(2-aminoethoxy)phenyl))-3-oxo-1-propenyl]-2-(carboxymethoxy)benzoate;

(w) (E)-Methyl 5-[[3-[3-((2-(methylamino)ethoxy))-phenyl]-3-oxo-1-propenyl]]-2-(carboxymethoxy)-benzoate;

(x) (E)-4-[3-((5-(2-aminoethoxy)-2-benzyloxy-phenyl))-1-oxo-1-prop-2-enyl]-2-ethoxyphenoxy-acetic acid;

(y) (E)-4-[2-((3-(2-aminoethoxy)phenylsulfonyl))-ethenyl]-2-nitrophenoxyacetic acid;

(z) (E)-4-[2-((3-(2-aminoethoxy)phenylthio))-ethenyl]-2-nitrophenoxyacetic acid;

(aa) (E)-4-[2-((3-(2-aminoethoxy)phenylsulfoxo))-ethenyl]-2-nitrophenoxyacetic acid;

(bb) (E)-4-[[1-[2-((3-(2-aminoethoxy)phenyl))-ethenyl] sulfonyl-2-methoxyphenoxyacetic acid;

(cc) (E)-4-[[1-[2-((3-(2-aminoethoxy)phenyl))-ethenyl] sulfoxo-2-methoxyphenoxyacetic acid;

(dd) (E)-4-[[1-[2-((3-(2-aminoethoxy)phenyl))-ethenyl] thio-2-methoxyphenoxyacetic acid.

10. A pharmaceutical composition comprising therapeutically effective amount of a compound of claim 1 and a pharmaceutically effective carrier.

11. A pharmaceutical composition comprising therapeutically effective amount of a compound of claim 4 and a pharmaceutically effective carrier.

12. A pharmaceutical composition comprising therapeutically effective amount of a compound of claim 5 and a pharmaceutically effective carrier.

13. A pharmaceutical composition comprising therapeutically effective amount of a compound of claim 6 and a pharmaceutically effective carrier.

14. A pharmaceutical composition comprising therapeutically effective amount of a compound of claim 7 and a pharmaceutically effective carrier.

15. A pharmaceutical composition comprising therapeutically effective amount of a compound of claim 8 and a pharmaceutically effective carrier.

16. A method of treating thrombus or embolus formation in a mammal which comprises administering to a mammal in need of such treatment a therapeutically effective amount of a compound of claim 1.

17. A method of preventing thrombus or embolus formation in a mammal which comprises administering to a mammal in need of such prevention a therapeutically effective amount of a compound of claim 1.

* * * * *